US008937089B2

(12) United States Patent
Annan et al.

(10) Patent No.: US 8,937,089 B2
(45) Date of Patent: Jan. 20, 2015

(54) SYNERGISTIC MIXTURES OF ANTHRANILAMIDE INVERTEBRATE PEST CONTROL AGENTS

(75) Inventors: Isaac Billy Annan, Newark, DE (US); John Lindsey Flexner, Landenberg, PA (US); Hector Eduardo Portillo, Newark, DE (US); George Philip Lahm, Wilmington, DE (US); Thomas Paul Selby, Hockessin, DE (US); Thomas Martin Stevenson, Newark, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 194 days.

(21) Appl. No.: 13/207,669

(22) Filed: Aug. 11, 2011

(65) Prior Publication Data
US 2011/0293533 A1 Dec. 1, 2011

Related U.S. Application Data

(62) Division of application No. 11/630,312, filed as application No. PCT/US2005/023813 on Jun. 30, 2005, now Pat. No. 8,022,067.

(60) Provisional application No. 60/584,601, filed on Jul. 1, 2004, provisional application No. 60/666,073, filed on Mar. 29, 2005.

(51) Int. Cl.
    A01N 43/50    (2006.01)
    A01N 43/40    (2006.01)
    A01N 51/00    (2006.01)
    A01N 43/56    (2006.01)

(52) U.S. Cl.
    CPC .................................... A01N 43/56 (2013.01)
    USPC ........................................ 514/341; 514/406

(58) Field of Classification Search
    USPC .................................. 514/341, 406
    See application file for complete search history.

(56) References Cited

U.S. PATENT DOCUMENTS

| 4,845,106 | A | * | 7/1989 | Shiokawa et al. ............. 514/342 |
| 5,998,424 | A | | 12/1999 | Galemmo et al. |
| 6,020,357 | A | | 2/2000 | Pinto et al. |
| 6,403,620 | B1 | | 6/2002 | Galemmo et al. |
| 6,602,895 | B2 | | 8/2003 | Pinto et al. |
| 6,747,047 | B2 | | 6/2004 | Lahm et al. |
| 7,199,138 | B2 | | 4/2007 | Finkelstein et al. |
| 7,232,836 | B2 | | 6/2007 | Lahm et al. |
| 7,541,377 | B2 | | 6/2009 | Finkelstein et al. |
| 7,696,233 | B2 | | 4/2010 | Lahm et al. |
| 7,902,231 | B2 | | 3/2011 | Lahm et al. |
| 8,268,750 | B2 | | 9/2012 | Funke et al. |
| 8,268,751 | B2 | | 9/2012 | Funke et al. |
| 8,299,036 | B2 | | 10/2012 | Funke et al. |
| 8,329,310 | B2 | * | 12/2012 | Hayward et al. ............. 428/532 |
| 8,546,305 | B2 | * | 10/2013 | Assmann et al. ............. 504/130 |
| 8,637,552 | B2 | | 1/2014 | Berger et al. |

(Continued)

FOREIGN PATENT DOCUMENTS

| AU | 2004290500 | 8/2011 |
| EP | 0946508 | 10/1999 |
| EP | 0991625 | 6/2005 |
| EP | 1686857 | 12/2008 |
| WO | 98/28269 | 7/1998 |
| WO | 98/57937 | 12/1998 |
| WO | 01/70671 | 9/2001 |
| WO | 03/015518 | 2/2003 |
| WO | 03/015519 | 2/2003 |
| WO | 2005/048711 | 6/2005 |

(Continued)

OTHER PUBLICATIONS

Mullins, J.W., "Imidacloprid," in: Duke, S. et al., Pest Control with Enhanced Environmental Safety, ACS Symposium Series, American Chemical Society, Washington, DC, 1993.*

(Continued)

*Primary Examiner* — John Pak

(57) ABSTRACT

Disclosed are mixtures and compositions for controlling invertebrate pests relating to combinations comprising (a) 3-bromo-N-[4-chloro-2-methyl-6-[(methylamino)carbonyl]phenyl]-1-(3-chloro-2-pyridinyl)-1H-pyrazole-5-carboxamide, and its N-oxides, and suitable salts thereof

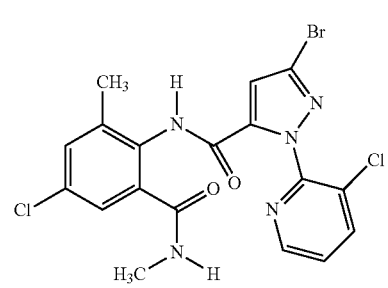

and
a component (b) wherein the component (b) is at least one compound or agent selected from neonicotinoids, cholinesterase inhibitors, sodium channel modulators, chitin synthesis inhibitors, ecdysone agonists, lipid biosynthesis inhibitors, macrocyclic lactones, GABA-regulated chloride channel blockers, juvenile hormone mimics, ryanodine receptor ligands, octopamine receptor ligands, mitochondrial electron transport inhibitors, nereistoxin analogs, pyridalyl, flonicamid, pymetrozine, dieldrin, metaflumizone, biological agents, and suitable salts of the foregoing.
Also disclosed are methods for controlling an invertebrate pest comprising contacting the invertebrate pest or its environment with a biologically effective amount of a mixture or composition of the invention.

5 Claims, No Drawings

(56) References Cited

U.S. PATENT DOCUMENTS

| | | |
|---|---|---|
| 8,697,734 B2 | 4/2014 | Lahm et al. |
| 2004/0171649 A1 | 9/2004 | Annis et al. |
| 2004/0192731 A1 | 9/2004 | Finkelstein et al. |
| 2004/0198984 A1 | 10/2004 | Lahm et al. |
| 2004/0198987 A1 | 10/2004 | Freudenberger et al. |
| 2004/0209923 A1 | 10/2004 | Berger et al. |
| 2005/0075372 A1 | 4/2005 | Lahm et al. |
| 2005/0124600 A1 | 6/2005 | Clark et al. |
| 2005/0274059 A1 | 12/2005 | Angst et al. |
| 2005/0282868 A1 | 12/2005 | Finkelstein et al. |
| 2006/0111403 A1 | 5/2006 | Hughes et al. |
| 2006/0167060 A1 | 7/2006 | Lahm et al. |
| 2007/0270416 A1 | 11/2007 | Funke et al. |
| 2010/0168042 A1 | 7/2010 | Funke et al. |
| 2010/0249070 A1 | 9/2010 | Funke et al. |
| 2010/0292226 A1 | 11/2010 | Funke et al. |
| 2012/0083491 A1 | 4/2012 | Funke et al. |
| 2013/0123247 A1 | 5/2013 | Lahm et al. |
| 2013/0190259 A1 | 7/2013 | Lahm et al. |
| 2013/0190313 A1 | 7/2013 | Lahm et al. |
| 2013/0190362 A1 | 7/2013 | Lahm et al. |
| 2014/0030243 A1 | 1/2014 | Lahm et al. |

FOREIGN PATENT DOCUMENTS

| | | |
|---|---|---|
| WO | 2005/048712 | 6/2005 |
| WO | 2005/048713 | 6/2005 |
| WO | 2005/053393 | 6/2005 |
| WO | 2005/053405 | 6/2005 |
| WO | 2005/053406 | 6/2005 |
| WO | 2005/079575 | 9/2005 |
| WO | 2005/107468 | 11/2005 |
| WO | 2006/008108 | 1/2006 |
| WO | 2006/068669 | 6/2006 |

OTHER PUBLICATIONS

HCAPLUS Abstract 1999:517189 (1999).
Revocation Decision dated Jan. 17, 2012 of European Patent Office in Opposition of EP1686857B1.
Statement of Grounds and Particulars in opposition of AU2004290500B2 by E. I. du Pont de Nemours and Company dated Feb. 3, 2012.
Statement of Grounds and Particulars in opposition of AU2004290500B2 by Syngenta Crop Protection AG dated Feb. 6, 2012.

* cited by examiner

SYNERGISTIC MIXTURES OF ANTHRANILAMIDE INVERTEBRATE PEST CONTROL AGENTS

This application is a division of application Ser. No. 11/630,312, filed Dec. 20, 2006, now U.S. Pat. No. 8,022,067 which is a national stage entry of PCT/US05/23813, filed Jun. 30, 2005. PCT/US05/23813 claims priority benefit from Provisional Application 60/584,601, filed Jul. 1, 2004; PCT/US05/23813 claims priority benefit from Provisional Application 60/666,073, filed on Mar. 29, 2005.

FIELD OF THE INVENTION

This invention relates to invertebrate pest control mixtures comprising a biologically effective amount of an anthranilamide, an N-oxide or a salt thereof and at least one other invertebrate pest control agent, and methods of their use for control of invertebrate pests such as arthropods in both agronomic and non-agronomic environments.

BACKGROUND OF THE INVENTION

The control of invertebrate pests is extremely important in achieving high crop efficiency. Damage by invertebrate pests to growing and stored agronomic crops can cause significant reduction in productivity and thereby result in increased costs to the consumer. The control of invertebrate pests in forestry, greenhouse crops, ornamentals, nursery crops, stored food and fiber products, livestock, household, turf, wood products, and public and animal health is also important. Many products are commercially available for these purposes and in practice have been used as a single or a mixed agent. However, more economically efficient and ecologically safe pest control compositions and methods are still being sought.

Being able to reduce the quantity of chemical agents released in the environment while ensuring effective pest control is always desirable. Although combinations of pest control agents have been studied, a high synergistic action is generally not found. Synergism has been described as "the cooperative action of two components of a mixture, such that the total effect is greater or more prolonged than the sum of the effects of the two (or more) taken independently" (see P. M. L. Yames, Neth. J. Plant Pathology 1964, 70, 73-80). Therefore, obtaining an arthropodicidal composition that demonstrates a high controlling effect with concomitant reduced crop production cost and reduced environmental load is highly desirable.

WO 03/015519 discloses N-acyl anthranilic acid derivatives of Formula i as arthropodicides

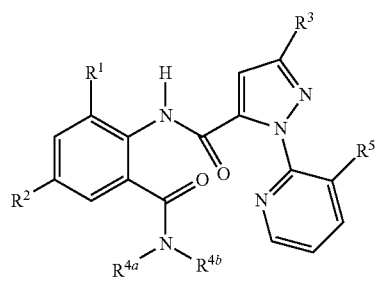

wherein, inter alia, $R^1$ is $CH_3$, F, Cl or Br; $R^2$ is F, Cl, Br, I or $CF_3$; $R^3$ is $CF_3$, Cl, Br or $OCH_2CF_3$; $R^{4a}$ is $C_1$-$C_4$ alkyl; $R^{4b}$ is H or $CH_3$; and $R^5$ is Cl or Br.

SUMMARY OF THE INVENTION

This invention is directed to a mixture comprising (a) a compound of Formula 1, 3-bromo-N-[4-chloro-2-methyl-6-[(methylamino)carbonyl]phenyl]-1-(3-chloro-2-pyridinyl)-1H-pyrazole-5-carboxamide, an N-oxide, or a salt thereof,

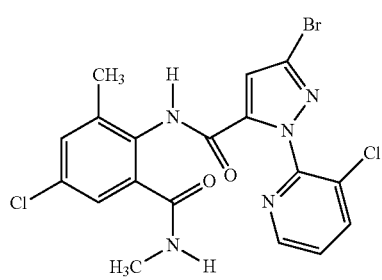

and
a component (b) wherein the component (b) is at least one invertebrate pest control agent selected from the group consisting of
 (b1) neonicotinoids;
 (b2) cholinesterase inhibitors;
 (b3) sodium channel modulators;
 (b4) chitin synthesis inhibitors;
 (b5) ecdysone agonists;
 (b6) lipid biosynthesis inhibitors;
 (b7) macrocyclic lactones;
 (b8) GABA-regulated chloride channel blockers;
 (b9) juvenile hormone mimics;
 (b10) ryanodine receptor ligands;
 (b11) octopamine receptor ligands;
 (b12) mitochondrial electron transport inhibitors;
 (b13) nereistoxin analogs;
 (b14) pyridalyl;
 (b15) flonicamid;
 (b16) pymetrozine;
 (b17) dieldrin;
 (b18) metaflumizone;
 (b19) biological agents; and
 salts of compounds of (b1) through (b18).

This invention also provides a composition for controlling an invertebrate pest comprising a biologically effective amount of a mixture of the invention and at least one additional component selected from the group consisting of a surfactant, a solid diluent and a liquid diluent, said composition optionally further comprising an effective amount of at least one additional biologically active compound or agent.

This invention also provides a method for controlling an invertebrate pest comprising contacting the invertebrate pest or its environment with a biologically effective amount of a mixture or composition of the invention, as described herein.

This invention further provides a spray composition comprising a mixture of the invention and a propellant. This invention also provides a bait composition comprising a mixture of the invention; one or more food materials; optionally an attractant; and optionally a humectant.

This invention further provides a trap device for controlling an invertebrate pest comprising said bait composition and a housing adapted to receive said bait composition, wherein the housing has at least one opening sized to permit the invertebrate pest to pass through the opening so the invertebrate pest can gain access to said bait composition from a location outside the housing, and wherein the housing is further adapted to be placed in or near a locus of potential or known activity for the invertebrate pest.

DETAILS OF THE INVENTION

As used herein, the terms "comprises," "comprising," "includes," "including," "has," "having" or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components of the invention. This is done merely for convenience and to give a general sense of the invention. This description should be read to include one or at least one and the singular also includes the plural unless it is obvious that it is meant otherwise.

Compounds in the mixtures and compositions of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises a mixture comprising a compound of Formula 1, an N-oxide, or a salt thereof, said compound of Formula 1, an N-oxide, or a salt thereof also referred to herein as "component (a)"; and at least one invertebrate pest control agent which can be a compound (or a salt thereof) selected from (b1) through (b18) or a biological agent selected from (b19) and is also referred to herein as "component (b)". Compositions of the present invention can optionally include at least one additional biologically active compound or agent, which if present in a composition will differ from the compound of Formula 1 and the component (b). These additional biologically active compounds or agents including insecticides, fungicides, nematicides, bactericides, acaricides, growth regulators such as rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agricultural or nonagronomic utility. These additional biologically active compounds or agents can be present as a mixture of stereoisomers, individual stereoisomers, or as an optically active form.

Salts of compounds in the mixtures and compositions of the present invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. Salts of the compounds of the invention also include those formed with organic bases (e.g., pyridine or triethylamine) or inorganic bases (e.g., hydrides, hydroxides, or carbonates of sodium, potassium, lithium, calcium, magnesium or barium) when the compound contains an acidic group such as a carboxylic acid or phenol.

Embodiments of the present invention include:

Embodiment 1

A mixture comprising a component (a) and a component (b) wherein the component (a) is a compound of Formula 1, an N-oxide, or a salt thereof.

Embodiment 2

The mixture of Embodiment 1 wherein the component (b) is at least one pest control agent selected from the group consisting of (b1) neonicotinoids, (b2) cholinesterase inhibitors and (b3) sodium channel modulators.

Embodiment 3

The mixture of Embodiment 1 wherein the component (b) is a compound selected from (b1) neonicotinoids.

Embodiment 4

The mixture of Embodiment 3 wherein the component (b) is selected from the group consisting of pyridylmethylamines such as acetamiprid and thiacloprid; nitromethylenes such as nitenpyram and nithiazine; and nitroguanidines such as clothianidin, dinotefuran, imidacloprid and thiamethoxam.

Embodiment 5

The mixture of Embodiment 4 wherein the component (b) is dinotefuran, imidacloprid, nitenpyram, thiacloprid or thiamethoxam.

Embodiment 5a

The mixture of Embodiment 4 wherein the component (b) is dinotefuran.

Embodiment 5b

The mixture of Embodiment 5 wherein the component (b) is imidacloprid.

Embodiment 5c

The mixture of Embodiment 5 wherein the component (b) is nitenpyram.

Embodiment 5d

The mixture of Embodiment 5 wherein the component (b) is thiacloprid.

Embodiment 5e

The mixture of Embodiment 5 wherein the component (b) is thiamethoxam.

Embodiment 6

The mixture of Embodiment 1 wherein the component (b) is a compound selected from (b2) cholinesterase inhibitors.

Embodiment 7

The mixture of Embodiment 6 wherein the component (b) is selected from the group consisting of organophosphates such as acephate, azinphos-methyl, chlorethoxyfos, chlorprazophos, chlorpyrifos, chlorpyrifos-methyl, coumaphos, cyanofenphos, demeton-S-methyl, diazinon, dichlorvos, dimethoate, dioxabenzofos, disulfoton, dithicrofos, fenamiphos, fenitrothion, fonofos, isofenphos, isoxathion, malathion, methamidophos, methidathion, mipafox, monocrotophos, oxydemeton-methyl, parathion, parathion-methyl, phorate, phosalone, phosmet, phosphamidon, phoxim, pirimiphos-methyl, profenofos, pyraclofos, quinalphos-methyl, sulprofos, temephos, terbufos, tetrachlorvinphos, thicrofos, triazophos, and trichlofon; and carbamates such as aldicarb, aldoxycarb, bendiocarb, benfuracarb, butocarboxim, carbaryl, carbofuran, carbosulfan, ethiofencarb, furathiocarb, methiocarb, methomyl (Lannate®), oxamyl (Vydate®), pirimicarb, propoxur, thiodicarb, triazarnate and xylylcarb.

Embodiment 8

The mixture of Embodiment 7 wherein the component (b) is methomyl or oxamyl.

Embodiment 8a

The mixture of Embodiment 8 wherein the component (b) is methomyl.

Embodiment 8b

The mixture of Embodiment 8 wherein the component (b) is oxamyl.

Embodiment 9

The mixture of Embodiment 1 wherein the component (b) is a compound selected from (b3) sodium channel modulators.

Embodiment 10

The mixture of Embodiment 9 wherein the component (b) is selected from the group consisting of pyrethroids such as allethrin, alpha-cypermethrin, beta-cyfluthrin, beta-cypermethrin, bifenthrin, cyfluthrin, cyhalothrin, cypermethrin, deltamethrin, esfenvalerate, fenfluthrin, fenpropathrin, fenvalerate, flucythrinate, gamma-cyhalothrin, lambda-cyhalothrin, metofluthrin, permethrin, profluthrin, resmethrin, tau-fluvalinate, tefluthrin, tetramethrin, tralomethrin, transfluthrin and zeta-cypermethrin; non-ester pyrethroids such as etofenprox, flufenprox, halfenprox, protrifenbute and silafluofen; oxadiazines such as indoxacarb; and natural pyrethrins such as cinerin-I, cinerin-II, jasmolin-I, jasmolin-II, pyrethrin-I and pyrethrin-II.

Embodiment 11

The mixture of Embodiment 10 wherein the component (b) is deltamethrin, indoxacarb or lambda-cyhalothrin.

Embodiment 11a

The mixture of Embodiment 11 wherein the component (b) is deltamethrin.

Embodiment 11b

The mixture of Embodiment 11 wherein the component (b) is indoxacarb.

Embodiment 11c

The mixture of Embodiment 11 wherein the component (b) is lambda-cyhalothrin.

Embodiment 12

The mixture of Embodiment 1 wherein the component (b) is a compound selected from (b4) chitin synthesis inhibitors.

Embodiment 13

The mixture of Embodiment 12 wherein the component (b) is selected from the group consisting of bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron and triflumuron.

Embodiment 14

The mixture of Embodiment 13 wherein the component (b) is hexaflumuron or novaluron.

Embodiment 14a

The mixture of Embodiment 14 wherein the component (b) is hexaflumuron.

Embodiment 14b

The mixture of Embodiment 14 wherein the component (b) is novaluron.

Embodiment 15

The mixture of Embodiment 1 wherein the component (b) is a compound selected from (b5) ecdysone agonists;

Embodiment 16

The mixture of Embodiment 15 wherein the component (b) is selected from the group consisting of azadirachtin, chromafenozide, halofenozide, methoxyfenozide and tebufenozide.

Embodiment 17

The mixture of Embodiment 1 wherein the component (b) is a compound selected from (b6) lipid biosynthesis inhibitors.

Embodiment 18

The mixture of Embodiment 17 wherein the component (b) is spiromesifen or spiridiclofen.

Embodiment 19

The mixture of Embodiment 1 wherein the component (b) is a compound selected from (b7) macrocyclic lactones.

Embodiment 20

The mixture of Embodiment 19 wherein the component (b) is selected from the group consisting of spinosad, abamectin, ivermectin, doramectin, emamectin, eprinomectin, ivermectin, milbemectin, milbemycin oxime, moxidectin, nemadectin and selamectin.

Embodiment 21

The mixture of Embodiment 20 wherein the component (b) is spinosad or abamectin.

Embodiment 21a

The mixture of Embodiment 21 wherein the component (b) is spinosad.

Embodiment 21b

The mixture of Embodiment 21 wherein the component (b) is abamectin.

Embodiment 22

The mixture of Embodiment 1 wherein the component (b) is a compound selected from (b8) GABA-regulated chloride channel blockers.

Embodiment 23

The mixture of Embodiment 22 wherein the component (b) is selected from the group consisting of acetoprole, endosulfan, ethiprole, fipronil and vaniliprole.

Embodiment 24

The mixture of Embodiment 23 wherein the component (b) is fipronil.

Embodiment 25

The mixture of Embodiment 1 wherein the component (b) is a compound selected from (b9) juvenile hormone mimics.

Embodiment 26

The mixture of Embodiment 25 wherein the component (b) is selected from the group consisting of epofenonane, fenoxycarb, hydroprene, kinoprene, methoprene, pyriproxyfen and triprene.

Embodiment 27

The mixture of Embodiment 26 wherein the component (b) is fenoxycarb or methoprene.

Embodiment 27a

The mixture of Embodiment 27 wherein the component (b) is fenoxycarb.

Embodiment 27b

The mixture of Embodiment 27 wherein the component (b) is methoprene.

Embodiment 28

The mixture of Embodiment 1 wherein the component (b) is a compound selected from (b10) ryanodine receptor ligands.

Embodiment 29

The mixture of Embodiment 28 wherein the component (b) is selected from the group consisting of ryanodine and other products of *Ryania speciosa* Vahl. (Flacourtiaceae) which are ryanodine receptor ligands, anthranliamides and phthalic diamides such as flubendiamide.

Embodiment 30

The mixture of Embodiment 1 wherein the component (b) is a compound selected from (b11) octopamine receptor ligands.

Embodiment 31

The mixture of Embodiment 30 wherein the component (b) is amitraz or chlordimeform.

Embodiment 31a

The mixture of Embodiment 31 wherein the component (b) is amitraz.

Embodiment 32

The mixture of Embodiment 1 wherein the component (b) is a compound selected from (b12) mitochondrial electron transport inhibitors.

Embodiment 33

The mixture of Embodiment 32 wherein the component (b) is selected from the group consisting of acequinocyl, chlofenapyr, diafenthiuron, dicofol, fenazaquin, fenpyroximate, hydramethylnon, pyridaben, rotenone, tebufenpyrad and tolfenpyrad.

Embodiment 34

The mixture of Embodiment 34 wherein the component (b) is chlofenapyr, hydramethylnon or pyridaben.

Embodiment 34a

The mixture of Embodiment 34 wherein the component (b) is chlofenapyr.

Embodiment 34b

The mixture of Embodiment 34 wherein component (b) is hydramethylnon.

Embodiment 34c

The mixture of Embodiment 34 wherein component (b) is pyridaben.

Embodiment 35

The mixture of Embodiment 1 wherein the component (b) is a compound selected from (b13) nereistoxin analogs.

Embodiment 36

The mixture of Embodiment 35 wherein the component (b) is selected from the group consisting of bensultap, cartap, thiocyclam and thiosultap.

Embodiment 37

The mixture of Embodiment 36 wherein the component (b) is cartap.

Embodiment 38

The mixture of Embodiment 1 wherein the component (b) is pyridalyl.

Embodiment 39

The mixture of Embodiment 1 wherein the component (b) is flonicamid.

Embodiment 40

The mixture of Embodiment 1 wherein the component (b) is pymetrozine.

Embodiment 41

The mixture of Embodiment 1 wherein the component (b) is dieldrin.

Embodiment 42

The mixture of Embodiment 1 wherein the component (b) is metaflumizone.

Embodiment 43

The mixture of Embodiment 1 wherein the component (b) is an agent selected from (b19) biological agents.

Embodiment 44

The mixture of Embodiment 43 wherein the component (b) is selected from the group consisting of *Bacillus thuringiensis* ssp. *aizawai*, *Bacillus thuringiensis* ssp. *kurstaki*, *Bacillus thuringiensis* encapsulated delta-endotoxins, *Beauvaria bassiana*, granulosis virus (CpGV and CmGV) and nuclear polyhedrosis virus (NPV, e.g., "Gemstar").

Embodiment 45

The mixture of Embodiment 1 wherein the component (b) is a compound selected from dinotefuran, imidacloprid, nitenpyram, thiacloprid, thiamethoxam, methomyl, oxamyl, deltamethrin, indoxacarb, lambda-cyhalothrin, hexaflumuron, novaluron, abamectin, spinosad, fipronil, fenoxycarb, methoprene, amitraz, chlofenapyr, hydramethylnon, pyridaben, cartap, flonicamid, pymetrozine and dieldrin.

Embodiment 46

The mixture of Embodiment 1 wherein the component (b) comprises at least one invertebrate pest control agent from each of two different groups selected from (b1), (b2), (b3), (b4), (b5), (b6), (b7), (b8), (b9), (b10), (b11), (b12), (b13), (b14), (b15), (b16), (b17), (b18) and (b19) and wherein any compound selected from any of groups (b1) through (b18) may be in a salt form.

Also noteworthy as embodiments are arthropodicidal compositions of the present invention comprising a biologically effective amount of a mixture of Embodiments 1 to 46 and at least one additional component selected from the group consisting of a surfactant, a solid diluent, a liquid diluent, and optionally at least one additional biologically active compound or agent. Embodiments of the invention further include methods for controlling an invertebrate pest comprising contacting the invertebrate pest or its environment with a biologically effective amount of a mixture of any of Embodiments 1 to 46 (e.g., as a composition described herein). Of note is a method comprising contacting the invertebrate pest or its environment with a biologically effective amount of the mixture of Embodiment 1-4, 6, 7, 9, 10, 15-20, 22, 23, 25, 26, 28-33, 35, 36, 38-45 or 46.

Embodiments of the invention also include a spray composition comprising a mixture of any of Embodiments 1 to 46 and a propellant. Of note is a spray composition comprising the mixture of Embodiment 1-4, 6, 7, 9, 10, 15-20, 22, 23, 25, 26, 28-33, 35, 36, 38-45 or 46. Embodiments of the invention further include a bait composition comprising a mixture of any of Embodiments 1 to 46; one or more food materials; optionally an attractant and optionally a humectant. Of note is a bait composition comprising the mixture of Embodiment 1-4, 6, 7, 9, 10, 15-20, 22, 23, 25, 26, 28-33, 35, 36, 38-45 or 46.

Embodiments of the invention also include a device for controlling an invertebrate pest comprising said bait composition and a housing adapted to receive said bait composition, wherein the housing has at least one opening sized to permit the invertebrate pest to pass through the opening so the invertebrate pest can gain access to said bait composition from a location outside the housing, and wherein the housing is further adapted to be placed in or near a locus of potential or known activity for the invertebrate pest. Of note is a device wherein the bait composition comprises the mixture of Embodiment 1-4, 6, 7, 9, 10, 15-20, 22, 23, 25, 26, 28-33, 35, 36, 38-45 or 46.

The compound of Formula 1 can be prepared by one or more of the methods and variations thereof as described in World Patent Application Publication WO 03/015519. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydroxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

The invertebrate pest control agent of groups (b1), (b2), (b3), (b4), (b5), (b6), (b7), (b8), (b9), (b10), (b11), (b12), (b13), (b14), (b15), (b16), (b17) and (b18) have been described in published patents and scientific journal papers. Most of the compounds of groups (b1) through (b18) and the biological agents of group (b19) are commercially available as active ingredients in invertebrate pest control products. These compounds and biological agents are described in compendia such as *The Pesticide Manual, 13th edition*, C. D. S. Thomlin (Ed.), British Crop Protection Council, Surrey, UK, 2003. Certain of these groups are further described below.

Neonicotinoids (Group (b1))

All neonicotinoids act as agonists at the nicotinic acetylcholine receptor in the central nervous system of insects. This causes excitation of the nerves and eventual paralysis, which leads to death. Due to the mode of action of neonicotinoids, there is no cross-resistance to conventional insecticide classes such as carbamates, organophosphates, and pyrethroids. A review of the neonicotinoids is described in *Pestology* 2003, 27, pp 60-63; *Annual Review of Entomology* 2003, 48, pp 339-364; and references cited therein.

Neonicotinoids act as acute contact and stomach poisons, combine systemic properties with relatively low application rates, and are relatively nontoxic to vertebrates. There are many compounds in this group including the pyridylmethylamines such as acetamiprid and thiacloprid; nitromethylenes such as nitenpyram and nithiazine; nitroguanidines such as clothianidin, dinotefuran, imidacloprid and thiamethoxam.

Cholinesterase Inhibitors (Group (b2))

Two chemical classes of compounds are known to inhibit the cholinesterase; one is the organophosphates and the other is the carbamates. Organophosphates involve phosphorylation of the enzyme, while carbamates involve a reversible carbamylation of the enzyme. The organophosphates include acephate, azinphos-methyl, chlorethoxyfos, chlorprazophos, chlorpyrifos, chlorpyrifos-methyl, coumaphos, cyanofenphos, demeton-S-methyl, diazinon, dichlorvos, dimethoate, dioxabenzofos, disulfoton, dithicrofos, fenamiphos, fenitrothion, fonofos, isofenphos, isoxathion, malathion, methamidophos, methidathion, mipafox, monocrotophos, oxydemeton-methyl, parathion, parathion-methyl, phorate, phosalone, phosmet, phosphamidon, phoxim, pirimiphos-methyl, profenofos, pyraclofos, quinalphos-methyl, sulprofos, temephos, terbufos, tetrachlorvinphos, thicrofos, triazophos, and trichlofon. The carbamates include aldicarb, aldoxycarb, bendiocarb, benfuracarb, butocarboxim, carbaryl, carbofuran, carbosulfan, ethiofencarb, furathiocarb, methiocarb, methomyl (Lannate®), oxamyl (Vydate®), pirimicarb, propoxur, thiodicarb, triazamate and xylylcarb. A general review of the mode of action of insecticides is presented in *Insecticides with Novel Modes of Action: Mechanism and Application*, I. Ishaaya, et al (Ed.), Springer:Berlin, 1998.

Sodium Channel Modulators (Group (b3))

Insecticidal compounds acting as sodium channel modulators disrupt the normal functioning of voltage-dependent sodium channels in insects, which causes rapid paralysis or knock-down following application of these insecticides. Reviews of insecticides targeting nerve membrane sodium channels are presented in, for example, *Toxicology* 2002, 171, pp 3-59; *Pest Management Sci.* 2001, 57, pp 153-164; and references cited therein. The sodium channel modulators have been grouped together based on their chemical structural similarity into four classes, including pyrethroids, non-ester pyrethroids, oxidiazines and natural pyrethrins. The pyrethroids include allethrin, alpha-cypermethrin, beta-cyfluthrin, beta-cypermethrin, bifenthrin, cyfluthrin, cyhalothrin, cypermethrin, deltamethrin, esfenvalerate, fenfluthrin, fenpropathrin, fenvalerate, flucythrinate, gamma-cyhalothrin, lambda-cyhalothrin, metofluthrin, permethrin, profluthrin, resmethrin, tau-fluvalinate, tefluthrin, tetramethrin, tralomethrin, transfluthrin and zeta-cypermethrin. The non-ester pyrethroids include etofenprox, flufenprox, halfenprox, protrifenbute and silafluofen. The oxadiazines include indoxacarb. The natural pyrethrins include cinerin-I, cinerin-II, jasmolin-I, jasmolin-II, pyrethrin-I and pyrethrin-II.

Other Insecticide Groups

Chitin synthesis inhibitors (b4) include bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron and triflumuron.

Ecdysone agonists (b5) include azadirachtin, chromafenozide, halofenozide, methoxyfenozide and tebufenozide.

Lipid biosynthesis inhibitors (b6) include spiromesifen and spiridiclofen.

Macrocyclic lactones (b7) include spinosad, abamectin, avermectin, doramectin, emamectin, eprinomectin, ivermectin, milbemectin, milbemycin oxime, moxidectin, nemadectin and selamectin.

GABA-regulated chloride channel blockers (b8) include acetoprole, endosulfan, ethiprole, fipronil and vaniliprole.

Juvenile hormone mimics (b9) include epofenonane, fenoxycarb, hydroprene, methoprene, pyriproxyfen and triprene.

Ryanodine receptor ligands (b10) include ryanodine and other related products of *Ryania speciosa* Vahl. (Flacourtiaceae), anthranilamides other than the compound of Formula 1 and phthalic diamides (disclosed in JP-A-11-240857 and JP-A-2001-131141) such as flubendiamide.

Octopamine receptor ligands (b11) include amitraz and chlordimeform.

Mitochondrial electron transport inhibitors (b12) include ligands which bind to complex I, II, or III sites to inhibit cellular respiration. Such mitochondrial electron transport inhibitors include acequinocyl, chlorfenapyr, diafenthiuron, dicofol, fenazaquin, fenpyroximate, hydramethylnon, pyridaben, rotenone, tebufenpyrad and tolfenpyrad.

Nereistoxin analogs (b13) include bensultap, cartap, thiocyclam and thiosultap.

Biological agents (b19) include entomopathogenic bacteria such as *Bacillus thuringiensis* ssp. *aizawai*, *Bacillus thuringiensis* ssp. *kurstaki*, *Bacillus thuringiensis* encapsulated delta-endotoxins, entomopathogenic fungi such as *Beauvaria bassiana*, and entomopathogenic viruses such as granulosis virus (CpGV and CmGV) and nuclear polyhedrosis virus (NPV, e.g., "Gemstar").

Other Insecticides, Acaricides, Nematicides

There are many known insecticides, acaricides and nematicides as disclosed in *The Pesticide Manual* $13^{th}$ Ed. 2003 including those whose mode of action is not yet clearly defined and those which are a single compound class including amidoflumet (S-1955), bifenazate, chlorofenmidine, dieldrin, diofenolan, fenothiocarb, flufenerim (UR-50701), metaldehyde, metaflumizone (BASF-320), methoxychlor, bactericides such as streptomycin; acaricides such as chinomethionat, chlorobenzilate, cyhexatin, dienochlor, etoxazole, fenbutatin oxide, hexythiazox and propargite.

The weight ratios of component (b) to the compound of Formula 1, an N-oxide, or a salt thereof in the mixtures, compositions and methods of the present invention are typically from 150:1 to 1:200, preferably from 150:1 to 1:50, more preferably from 50:1 to 1:10 and most preferably from 5:1 to 1:5. Of note are mixtures, compositions and methods wherein component (b) is a compound selected from (b1) neonicotinoids and the weight ratio of component (b) to the compound of Formula 1, an N-oxide, or a salt thereof is from 150:1 to 1:200. Also of note are mixtures, compositions and methods wherein component (b) is a compound selected from (b2) cholinesterase inhibitors and the weight ratio of component (b) to the compound of Formula 1, an N-oxide, or a salt thereof is from 200:1 to 1:100. Also of note are mixtures, compositions and methods wherein component (b) is a compound selected from (b3) sodium channel modulators and the weight ratio of component (b) to the compound of Formula 1, an N-oxide, or a salt thereof is from 100:1 to 1:10.

Of further note are mixtures, compositions and methods of the present invention wherein component (b) is a compound selected from (b1) neonicotinoids and the weight ratio of component (b) to the compound of Formula 1, an N-oxide, or a salt thereof is from 10:1 to 1:50. Also of note are mixtures, compositions and methods of the present invention wherein component (b) is a compound of (b2) cholinesterase inhibitors and the weight ratio of component (b) to the compound of Formula 1, an N-oxide, or a salt thereof, is from 150:1 to 1:25. Of further note are mixtures, composition and methods of the present invention wherein component (b) is a compound of (b3) sodium channel modulators and the weight ratio of component (b) to the compound of Formula 1, an N-oxide, or a salt thereof, is from 50:1 to 1:5.

Of note are mixtures, compositions and methods wherein component (b) comprises at least one compound (or a salt thereof) or biological agent from each of two different groups selected from (b1), (b2), (b3), (b4), (b5), (b6), (b7), (b8), (b9), (b10), (b11), (b12), (b13), (b14), (b15), (b16), (b17), (b18) and (b19).

Table 1 lists specific combinations of the compound of Formula 1 with other invertebrate pest control agents illustrative of the mixtures, compositions and methods of the present invention. The first column of Table 1 lists the group to which the component (b) belongs (e.g., "b1" in the first line). The second column of Table 1 lists specific invertebrate pest control agents (e.g., "Acetimiprid" in the first line). The third column of Table 1 lists atypical range of weight ratios of rates at which component (b) is applied relative to the compound of Formula 1 (e.g., "150:1 to 1:200" of acetamiprid relative to the compound of Formula 1 by weight). The fourth and fifth columns respectively list one embodiment of a weight ratio range and another embodiment of a weight ratio range for applications rates. Thus, for example, the first line of Table 1 specifically discloses the combination of the compound of Formula 1 with acetamiprid, identifies that acetamiprid is a member of component (b) group (b1), and indicates that acetamiprid and the compound of Formula 1 are typically applied in a weight ratio between 150:1 to 1:200, with one embodiment being 10:1 to 1:100 and another embodiment being 5:1 to 1:25. The remaining lines of Table 1 are to be construed similarly.

TABLE 1

| Component (b) | Invertebrate Pest Control Agent | Typical Weight Ratio | Preferred Weight Ratio | More Preferred Weight Ratio |
| --- | --- | --- | --- | --- |
| b1 | Acetamiprid | 150:1 to 1:200 | 10:1 to 1:100 | 5:1 to 1:25 |
| b1 | Clothianidin | 100:1 to 1:400 | 10:1 to 1:25 | 5:1 to 1:5 |
| b1 | Dinotefuran | 150:1 to 1:500 | 10:1 to 1:100 | 5:1 to 1:25 |
| b1 | Imidacloprid | 100:1 to 1:400 | 10:1 to 1:25 | 5:1 to 1:10 |
| b1 | Nitenpyram | 150:1 to 1:200 | 10:1 to 1:50 | 5:1 to 1:25 |
| b1 | Nithiazine | 150:1 to 1:200 | 10:1 to 1:50 | 5:1 to 1:25 |
| b1 | Thiacloprid | 100:1 to 1:250 | 15:1 to 1:30 | 5:1 to 1:5 |
| b1 | Thiamethoxam | 150:1 to 1:500 | 20:1 to 1:50 | 5:1 to 1:10 |
| b2 | Methomyl | 100:1 to 1:50 | 50:1 to 1:25 | 5:1 to 1:10 |
| b2 | Oxamyl | 100:1 to 1:50 | 50:1 to 1:10 | 5:1 to 1:1 |
| b2 | Thiodicarb | 200:1 to 1:100 | 150:1 to 1:25 | 50:1 to 1:5 |
| b2 | Triazamate | 200:1 to 1:100 | 150:1 to 1:25 | 50:1 to 1:5 |
| b3 | Bifenthrin | 100:1 to 1:10 | 50:1 to 1:5 | 10:1 to 1:1 |
| b3 | Deltamethrin | 50:1 to 1:500 | 25:1 to 1:50 | 10:1 to 1:10 |
| b3 | Esfenvalerate | 100:1 to 1:10 | 50:1 to 1:5 | 5:1 to 1:1 |
| b3 | Indoxacarb | 100:1 to 1:100 | 25:1 to 1:25 | 10:1 to 1:10 |
| b3 | Lambda-cyhalothrin | 50:1 to 1:10 | 25:1 to 1:5 | 5:1 to 1:1 |
| b3 | Pyrethrin | 100:1 to 1:10 | 50:1 to 1:5 | 5:1 to 1:1 |
| b4 | Buprofezin | 200:1 to 1:150 | 100:1 to 1:50 | 50:1 to 1:5 |
| b4 | Cyromazine | 200:1 to 1:150 | 100:1 to 1:50 | 50:1 to 1:5 |
| b4 | Hexaflumuron | 200:1 to 1:150 | 100:1 to 1:10 | 50:1 to 1:1 |
| b4 | Lufenuron | 200:1 to 1:150 | 100:1 to 1:50 | 50:1 to 1:5 |
| b4 | Novaluron | 250:1 to 1:150 | 100:1 to 1:10 | 50:1 to 1:1 |
| b5 | Azadirachtin | 100:1 to 1:120 | 20:1 to 1:10 | 1:1 to 1:5 |
| b5 | Methoxyfenozide | 50:1 to 1:750 | 25:1 to 1:250 | 1:1 to 1:100 |
| b5 | Tebufenozide | 50:1 to 1:250 | 25:1 to 1:150 | 1:1 to 1:25 |
| b6 | Spiridiclofen | 200:1 to 1:200 | 20:1 to 1:20 | 10:1 to 1:10 |
| b6 | Spiromesifen | 200:1 to 1:200 | 20:1 to 1:20 | 10:1 to 1:10 |
| b7 | Abamectin | 50:1 to 1:500 | 25:1 to 1:250 | 5:1 to 1:100 |
| b7 | Emamectin Benzoate | 50:1 to 1:10 | 25:1 to 1:5 | 5:1 to 1:1 |
| b7 | Spinosad | 50:1 to 1:10 | 25:1 to 1:5 | 5:1 to 1:1 |
| b8 | Fipronil | 50:1 to 1:100 | 25:1 to 1:50 | 5:1 to 1:25 |
| b9 | Fenoxycarb | 250:1 to 1:100 | 150:1 to 1:50 | 50:1 to 1:10 |
| b9 | Methoprene | 500:1 to 1:100 | 250:1 to 1:50 | 50:1 to 1:10 |
| b9 | Pyriproxyfen | 200:1 to 1:100 | 100:1 to 1:50 | 50:1 to 1:10 |
| b10 | Anthranilamide | 100:1 to 1:200 | 20:1 to 1:100 | 1:1 to 1:50 |
| b10 | Flubendiamide | 100:1 to 1:200 | 20:1 to 1:100 | 1:1 to 1:50 |
| b10 | Ryanodine | 100:1 to 1:120 | 20:1 to 1:10 | 1:1 to 1:5 |
| b11 | Amitraz | 250:1 to 1:100 | 100:1 to 1:50 | 25:1 to 1:10 |
| b12 | Chlorfenapyr | 1200:1 to 1:200 | 400:1 to 1:100 | 200:1 to 1:50 |
| b12 | Hydramethylnon | 100:1 to 1:500 | 20:1 to 1:100 | 1:1 to 1:10 |

TABLE 1-continued

| Component (b) | Invertebrate Pest Control Agent | Typical Weight Ratio | Preferred Weight Ratio | More Preferred Weight Ratio |
|---|---|---|---|---|
| b12 | Pyridaben | 200:1 to 1:100 | 100:1 to 1:50 | 50:1 to 1:10 |
| b13 | Cartap | 100:1 to 1:1000 | 50:1 to 1:500 | 5:1 to 1:100 |
| b14 | Pyridalyl | 200:1 to 1:100 | 100:1 to 1:50 | 50:1 to 1:10 |
| b15 | Flonicamid | 20:1 to 1:500 | 15:1 to 1:250 | 5:1 to 1:50 |
| b16 | Pymetrozine | 200:1 to 1:500 | 150:1 to 1:250 | 50:1 to 1:50 |
| b17 | Dieldrin | 200:1 to 1:500 | 100:1 to 1:100 | 25:1 to 1:50 |
| b18 | Metaflumizone | 200:1 to 1:200 | 100:1 to 1:100 | 20:1 to 1:20 |
| b19 | *Bacillus thuringiensis* | 50:1 to 1:10 | 25:1 to 1:5 | 5:1 to 1:1 |
| b19 | Beauvaria bassiana | 50:1 to 1:10 | 25:1 to 1:5 | 5:1 to 1:1 |
| b19 | NPV (e.g., Gemstar) | 50:1 to 1:10 | 25:1 to 1:5 | 5:1 to 1:1 |

Of note are mixtures and compositions of this invention that can also be mixed with one or more other biologically active compounds or agents including insecticides, fungicides, nematicides, bactericides, acaricides, growth regulators such as rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agricultural or nonagronomic utility. Thus the present invention also pertains to a mixture or a composition comprising a biologically effective amount of a compound of Formula 1, an N-oxide thereof, or an agronomic or nonagronomic suitable salt thereof (component (a)); an effective amount of at least one additional biologically active compound (or salt thereof) or agent selected from the group consisting of (b1), (b2), (b3), (b4), (b5), (b6), (b7), (b8), (b9), (b10), (b11), (b12), (b13), (b14), (b15), (b16), (b17), (b18), (b19) (component (b)); and can further comprise at least one of a surfactant, a solid diluent or a liquid diluent and optionally further comprise an effective amount of at least one additional biologically active compound or agent. Such optionally biologically active compound(s) or agent(s) if present with the mixtures and compositions of this invention will differ from the components (a) and (b), said additional biologically active compound(s) or agent(s) can be an insecticide, an acaricide, a nematicide or a fungicide. Examples of an insecticide include a compound (or salt thereof) selected from the group consisting of amidoflumet (S-1955), bifenazate, chlorofenmidine, diofenolan, fenothiocarb, flufenerim (UR-50701), metaldehyde, methoxychlor; and examples of fungicides including acibenzolar-S-methyl, azoxystrobin, benalazy-M, benthiavalicarb, benomyl, blasticidin-S, Bordeaux mixture (tribasic copper sulfate), boscalid, bromuconazole, buthiobate, carpropamid, captafol, captan, carbendazim, chloroneb, chlorothalonil, clotrimazole, copper oxychloride, copper salts, cymoxanil, cyazofamid, cyflufenamid, cyproconazole, cyprodinil, diclocymet, diclomezine, dicloran, difenoconazole, dimethomorph, dimoxystrobin, diniconazole, diniconazole-M, dodine, edifenphos, epoxiconazole, ethaboxam, famoxadone, fenarimol, fenbuconazole, fenhexamid, fenoxanil, fenpiclonil, fenpropidin, fenpropimorph, fentin acetate, fentin hydroxide, fluazinam, fludioxonil, flumorph, fluoxastrobin, fluquinconazole, flusilazole, flutolanil, flutriafol, folpet, fosetyl-aluminum, furalaxyl, furametapyr, guazatine, hexaconazole, hymexazol, imazalil, imibenconazole, iminoctadine, ipconazole, iprobenfos, iprodione, iprovalicarb, isoconazole, isoprothiolane, kasugamycin, kresoxim-methyl, mancozeb, maneb, mefenoxam, mepanapyrim, mepronil, metalaxyl, metconazole, metominostrobin/fenominostrobin, metrafenone, miconazole, myclobutanil, neo-asozin (ferric methanearsonate), nuarimol, oryzastrobin, oxadixyl, oxpoconazole, penconazole, pencycuron, picobenzamid, picoxystrobin, probenazole, prochloraz, propamocarb, propiconazole, proquinazid, prothioconazole, pyraclostrobin, pyrimethanil, pyrifenox, pyroquilon, quinoxyfen, silthiofam, simeconazole, sipconazole, spiroxamine, sulfur, tebuconazole, tetraconazole, tiadinil, thiabendazole, thifluzamide, thiophanate-methyl, thiram, tolylfluanid, triadimefon, triadimenol, triarimol, tricyclazole, trifloxystrobin, triflumizole, triforine, triticonazole, uniconazole, validamycin, vinclozolin and zoxamide. Compositions of this invention can be applied to plants genetically transformed to express proteins toxic to invertebrate pests (such as *Bacillus thuringiensis* toxin). The effect of the exogenously applied invertebrate pest control compounds of this invention may be synergistic with the expressed toxin proteins.

The weight ratios of these various mixing partners to the compound of Formula 1, an N-oxide or a salt thereof of this invention typically are between 200:1 and 1:150, with one embodiment being between 150:1 and 1:50, another embodiment being between 50:1 and 1:10 and another embodiment being between 5:1 and 1:5.

The mixtures and compositions of this invention are useful to control invertebrate pests. In certain instances, combinations with other invertebrate pest control active ingredients having a similar spectrum of control but a different mode of action will be particularly advantageous for resistance management Formulation/Utility Mixtures of this invention can generally be used as a formulation or composition with a carrier suitable for agronomic and nonagronomic uses comprising at least one of a liquid diluent, a solid diluent or a surfactant. The formulation, mixture or composition ingredients can be selected to be consistent with the physical properties of the active ingredients, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films (including seed treatment), and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Compositions of the invention can also optionally comprise plant nutrients, e.g. a fertilizer composition comprising at least one plant nutrient selected from nitrogen, phosphorus, potassium, sulfur, calcium, magnesium, iron, copper, boron, manganese, zinc, and molybdenum. Of note are compositions comprising at least one fertilizer composition comprising at least one plant nutrient selected from nitrogen, phosphorus, potassium, sulfur, calcium and magnesium. Compositions of the present invention which further comprise at least one plant nutrient can be in the form of liquids or solids. Of note are solid formulations in the form of granules, small sticks or tablets. Solid formulations comprising a fertilizer composition can be prepared by mixing the mixture or composition of the present invention with the fertilizer composition together with formulating ingredients and then preparing the formulation by methods such as granulation or extrusion. Alternatively solid formulations can be prepared by spraying a solution or suspension of a mixture or composition of the present invention in a volatile solvent onto a previous prepared fertilizer composition in the form of dimensionally stable mixtures, e.g., granules, small sticks or tablets, and then evaporating the solvent. Sprayable formulations can be extended in suitable media and used at spray volumes from about one to several hundred liters per hectare. High-strength compositions can be primarily used as intermediates for further formulation.

The formulations will typically contain effective amounts of active ingredient, diluent and surfactant within the following approximate ranges which add up to 100 percent by weight.

|  | Weight Percent | | |
| --- | --- | --- | --- |
|  | Active Ingredients | Diluent | Surfactant |
| Water-Dispersible and Water-soluble Granules, Tablets and Powders. | 0.001-90 | 0-99.999 | 0-15 |
| Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, glycerol esters, poly-oxyethylene/polyoxypropylene block copolymers, and alkylpolyglycosides where the number of glucose units, referred to as degree of polymerization (D.P.), can range from 1 to 3 and the alkyl units can range from $C_6$-$C_{14}$ (see *Pure and Applied Chemistry* 72, 1255-1264). Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, glycerine, triacetine, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, acetates and alcohols such as methanol, cyclohexanol, decanol and tetrahydrofurfuryl alcohol.

Useful formulations of this invention can also contain materials known as formulation aids including antifoams, film formers and dyes and are well known to those skilled in the art.

Antifoams can include water dispersible liquids comprising polyorganosiloxanes such as Rhodorsil® 416. The film formers can include polyvinyl acetates, polyvinyl acetate copolymers, polyvinylpyrrolidone-vinyl acetate copolymer, polyvinyl alcohols, polyvinyl alcohol copolymers and waxes. Dyes can include water dispersible liquid colorant compositions such as Pro-lzed® Colorant Red. One skilled in the art will appreciate that this is a non-exhaustive list of formulation aids. Suitable examples of formulation aids include those listed herein and those listed in McCutcheon's 2001, Volume 2: Functional Materials, published by MC Publishing Company and PCT Publication WO 03/024222.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; and Hance et al., *Weed Control Handbook*, 8th Ed., Blackwell Scientific Publications, Oxford, 1989; *Developments in formulation technology*, PJB Publications, Richmond, UK, 2000.

In the following Examples, all percentages are by weight and all formulations are prepared in conventional ways. "Active ingredients" refers to the aggregate of invertebrate pest control agents consisting of component (b) in combination with the compound of Formula 1, an N-oxide or salt thereof. Without further elaboration, it is believed that one skilled in the art using the preceding description can utilize the present invention to its fullest extent. The following Examples are, therefore, to be constructed as merely illustrative, and not limiting of the disclosure in any way whatsoever. Percentages are by weight except where otherwise indicated.

Example A

| Wettable Powder | |
|---|---|
| active ingredients | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example B

| Granule | |
|---|---|
| active ingredients | 10.0% |
| attapulgite granules (low volatile matter, 0.71/0.30 mm; U.S.S. No. 25-50 sieves) | 90.0% |

Example C

| Extruded Pellet | |
|---|---|
| active ingredients | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 50.0% |

Example D

| Emulsifiable Concentrate | |
|---|---|
| active ingredients | 20.0% |
| blend of oil soluble sulfonates and polyoxyethylene ethers | 10.0% |
| isophorone | 70.0% |

Example E

| Microemulsion | |
|---|---|
| active ingredients | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example F

| Seed Treatment | |
|---|---|
| active ingredients | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 2.00% |

| Seed Treatment | |
|---|---|
| stearyl alcohol (POE 20) | 0.20% |
| polyorganosilane | 0.05% |
| colorant red dye | 65.75% |
| water | |

Example G

| Fertilizer Stick | |
|---|---|
| active ingredients | 2.50% |
| pyrrolidone-styrene copolymer | 4.80% |
| tristyrylphenyl 16-ethoxylate | 2.30% |
| talc | 0.80% |
| corn starch | 5.00% |
| Nitrophoska ® Permanent 15-9-15 slow-release fertilizer (BASF) | 36.00% |
| kaolin | 38.00% |
| water | 10.60% |

Compositions and mixtures of this invention are characterized by favorable metabolic and/or soil residual patterns and exhibit activity controlling a spectrum of agronomic and nonagronomic invertebrate pests. (In the context of this disclosure "invertebrate pest control" means inhibition of invertebrate pest development (including mortality) that causes significant reduction in feeding or other injury or damage caused by the pest; related expressions are defined analogously.) As referred to in this disclosure, the term "invertebrate pest" includes arthropods, gastropods and nematodes of economic importance as pests. The term "arthropod" includes insects, mites, spiders, scorpions, centipedes, millipedes, pill bugs and symphylans. The term "gastropod" includes snails, slugs and other Stylommatophora. The term "nematode" includes all of the helminths, such as: roundworms, heartworms, and phytophagous nematodes (Nematoda), flukes (Tematoda), Acanthocephala, and tapeworms (Cestoda). Those skilled in the art will recognize that not all compositions or mixtures are equally effective against all pests. Compositions and mixtures of this invention display activity against economically important agronomic and nonagronomic pests. The term "agronomic" refers to the production of field crops such as for food and fiber and includes the growth of corn, soybeans and other legumes, rice, cereal (e.g., wheat, oats, barley, rye, rice, maize), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (berries, cherries) and other specialty crops (e.g., canola, sunflower, olives). The term "nonagronomic" refers to other horticultural crops (e.g., greenhouse, nursery or ornamental plants not grown in a field), residential and commercial structures in urban and industrial settings, turf (commercial, golf, residential, recreational, etc.), wood products, stored product agro-forestry and vegetation management, public health (human) and animal health (pets, livestock, poultry, non-domesticated animals such as nature animals) applications. For reasons of invertebrate pest control spectrum and economic importance, protection of agronomic crops from damage or injury caused by invertebrate pests by controlling invertebrate pests are embodiments of the invention.

Agronomic or nonagronomic pests include larvae of the order Lepidoptera, such as armyworms, cutworms; loopers, and heliothines in the family Noctuidae (e.g., fall armyworm (*Spodoptera fugiperda* J. E. Smith), beet armyworm (*Spodoptera exigua* Hübner), black cutworm (*Agrotis ipsilon* Hufnagel), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworms (Pyralidae: Crambinae) such as sod webworm (*Herpetogramma licarsisalis* Walker)); leafrollers, budworms, seed worms, and fruit worms in the family Tortricidae (e.g., codling moth (*Cydia pomonella* Linnaeus), grape berry moth (*Endopiza viteana* Clemens), oriental fruit moth (*Grapholita molesta* Busck)); and many other economically important lepidoptera (e.g., diamondback moth (*Plutella xylostella* Linnaeus), pink bollworm (*Pectinophord gossypiella* Saunders), gypsy moth (*Lymantria dispar* Linnaeus)); nymphs and adults of the order Blattodea including cockroaches from the families Blattellidae and Blattidae (e.g., oriental cockroach (*Blatta orientalis* Linnaeus), Asian cockroach (*Blatella asahinai* Mizukubo), German cockroach (*Blattella gerrnanica* Linnaeus), brown-banded cockroach (*Supella longipalpa* Fabricius), American cockroach (*Periplaneta americana* Linnaeus), brown cockroach (*Periplaneta brunnea* Burmeister), Madeira cockroach (*Leucophaea maderae* Fabricius), smoky brown cockroach (*Periplaneta fuliginosa* Service), Australian Cockroach (*Periplaneta australasiae* Fabr.), lobster cockroach (*Nauphoeta cinerea* Olivier) and smooth cockroach (*Symploce pallens* Stephens)); foliar feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), granary weevil (*Sitophilus granarius* Linnaeus), rice weevil (*Sitophilus oryzae* Linnaeus), annual bluegrass weevil (*Listronotus maculicollis* Dietz), bluegrass billbug (*Sphenophorus parvulus* Gyllenhal), hunting billbug (*Sphenophorus vencaus* vestitus), Denver billbug (*Sphenophorus cicatristriatus* Fahraeus)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera virgifera* LeConte)); chafers and other beetles from the family Scaribaeidae (e.g., Japanese beetle (*Popillia japonica* Newman), oriental beetle (*Anomala orientalis* Waterhouse), northern masked chafer (*Cyclocephala borealis* Arrow), southern masked chafer (*Cyclocephala immaculate* Olivier), black turfgrass ataenius (*Ataenius spretulus* Haldeman), green June beetle (*Cotinis nitida* Linnaeus), Asiatic garden beetle (*Maladera castanea* Arrow), May/June beetles (*Phyllophaga* spp.) and European chafer (*Rhizotrogus majalis* Razoumowsky)); carpet beetles from the family Dermestidae; wireworms from the family Elateridae; bark beetles from the family Scolytidae and flour beetles from the family Tenebrionidae. In addition, agronomic and nonagronomic pests include: adults and larvae of the order Dermaptera including earwigs from the family Forficulidae (e.g., European earwig (*Forficula auricularia* Linnaeus), black earwig (*Chelisoches mono* Fabricius)); adults and nymphs of the orders Hemiptera and Homoptera such as, plant bugs from the family Miridae, cicadas from the family Cicadidae, leafhoppers (e.g. *Empoasca* spp.) from the family Cicadellidae, planthoppers from the families Fulgoroidea and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, chinch bugs (e.g., hairy chinch bug (*Blissus leucopterus hirtus* Montandon) and southern chinch bug (*Blissus insularis* Barber)) and other seed bugs from the family Lygaeidae, spittlebugs from the family Cercopidae, squash bugs from the family Coreidae, and red bugs and cotton stainers from the family Pyrrhocoridae. Also included are adults and larvae of the order Acari (mites) such as spider mites and red mites in the family Tetranychidae (e.g., European red mite (*Panonychus ulmi* Koch), two spotted spider mite (*Tetranychus urticae* Koch), McDaniel mite (*Tetranychus mcdanieli* McGregor)); flat mites in the family Tenuipalpidae (e.g., citrus flat mite (*Brevipalpus lewisi* McGregor)); rust and bud mites in the family Eriophyidae and other foliar feeding mites and mites important in human and animal health, i.e. dust mites in the family Epidermoptidae, follicle mites in the family Demodicidae, grain mites in the family Glycyphagidae, ticks in the order Ixodidae (e.g., deer tick (*Ixodes scapularis* Say), Australian paralysis tick (*Ixodes holocyclus* Neumann), American dog tick (*Dermacentor variabilis* Say), lone star tick (*Amblyomma americanum* Linnaeus)) and scab and itch mites in the families Psoroptidae, Pyemotidae, and Sarcoptidae; adults and immatures of the order Orthoptera including grasshoppers, locusts and crickets (e.g., migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forskal), migratory locust (*Locusta migrcrtoria* Linnaeus), bush locust (*Zonocerus* spp.), house cricket (*Acheta domesticus* Linnaeus), mole crickets (e.g., tawny mole cricket (*Scapteriscus vicinus* Scudder) and southern mole cricket (*Scapteriscus borellii* Giglio-Tos)); adults and immatures of the order Diptera including leafminers, midges, fruit flies (Tephritidae), frit flies (e.g., *Oscinella frit* Linnaeus), soil maggots, house flies (e.g., *Musca domestica* Linnaeus), lesser house flies (e.g., *Fannia canicularis* Linnaeus, *F. femoralis* Stein), stable flies (e.g., *Stomoxys calcitrans* Linnaeus), face flies, horn flies, blow flies (e.g., *Chrysomya* spp., *Phormia* spp.), and other muscoid fly pests, horse flies (e.g., *Tabanus* spp.), bot flies (e.g., *Gastrophilus* spp., *Oestrus* spp.), cattle grubs (e.g., *Hypoderma* spp.), deer flies (e.g., *Chrysops* spp.), keds (e.g., *Melophagus ovinus* Linnaeus) and other Brachycera, mosquitoes (e.g., *Aedes* spp., *Anopheles* spp., *Culex* spp.), black flies (e.g., *Prosimulium* spp., *Simulium* spp.), biting midges, sand flies, sciarids, and other Nematocera; adults and immatures of the order Thysanoptera including onion thrips (*Thrips tabaci* Lindeman), flower thrips (*Frankliniella* spp.), and other foliar feeding thrips; insect pests of the order Hymenoptera including ants (e.g., red carpenter ant (*Camponotus ferrugineus* Fabricius), black carpenter ant (*Camponotus pennsylvanicus* De Geer), Pharaoh ant (*Monomorium pharaonic* Linnaeus), little fire ant (*Wasmannia auropunctata* Roger), fire ant (*Solenopsis geminata* Fabricius), red imported fire ant (*Solenopsis invicta* Buren), Argentine ant (*Iridomyrmex humilis* Mayr), crazy ant (*Paratrechina longicornis* Latreille), pavement ant (*Tetramorium caespitum* Linnaeus), cornfield ant (*Lasius alienus* Förster), odorous house ant (*Tapinoma sessile* Say), bees (including carpenter bees), hornets, yellow jackets, wasps, and sawflies (*Neodiprion* spp.; *Cephus* spp.); insect pests of the Family Formicidae including the Florida carpenter ant (*Camponotus floridanus* Buckley), white-footed ant (*Technomyrmex albipes* fr. Smith), big headed ants (*Pheidole* sp.) and ghost ant (*Tapinoma melanocephalum* Fabricius); insect pests of the order Isoptera including termites in the Termitidae (ex. *Macrotermes* sp.), Kalotermitidae (ex. *Cryptotermes* sp.), and Rhinotermitidae (ex. *Reticulitermes* sp., *Coptotermes* sp.) families the eastern subterranean termite (*Reticulitermes flavipes* Kollar), western subterranean termite (*Reticulitermes hesperus* Banks), Formosan subterranean termite (*Coptotermes formosanus* Shiraki), West Indian drywood termite (*Incisitermes immigrans* Snyder), powder post termite (*Cryptotermes brevis* Walker), drywood termite (*Incisitermes snyderi* Light), southeastern subterranean termite (*Reticulitermes virginicus* Banks), western drywood termite (*Incisitermes minor* Hagen), arboreal termites such as *Nasutitermes* sp. and other termites of economic importance; insect pests of the order Thysanura such as silverfish (*Lepisma saccharina* Linnaeus) and firebrat (*Thermobia domestica* Packard); insect pests of the order Mallophaga and including the head louse (*Pediculus humanus capitis* De Geer), body louse (*Pediculus humanus humanus* Linnaeus), chicken body louse (*Menacanthus stramineus* Nitzsch), dog biting louse (*Trichodectes canis* De Geer), fluff louse (*Goniocotes gallinae* De Geer), sheep body louse (*Bovicola ovis* Schrank), short-nosed cattle louse (*Haematopinus eurysternus* Nitzsch), long-nosed cattle louse (*Linognathus vituli* Linnaeus) and other sucking and chewing parasitic lice that attack man and animals; insect pests of the order Siphonoptera including the oriental rat flea (*Xenopsylla cheopis* Rothschild), cat flea (*Ctenocephalides felis* Bouche), dog flea (*Ctenocephalides canis* Curtis), hen flea (*Ceratophyllus gallinae* Schrank), sticktight flea (*Echidnophaga gallinacea* Westwood), human flea (*Pulex irritans* Linnaeus) and other fleas afflicting mammals and birds. Additional arthropod pests covered include: spiders in the order Araneae such as the brown recluse spider (*Loxosceles reclusa* Gertsch & Mulaik) and the black widow spider (*Latrodectus mactans* Fabricius), and centipedes in the order Scutigeromorpha such as the house centipede (*Scutigera coleoptrata* Linnaeus). Mixtures and compositions of the present invention also have activity on members of the Classes Nematoda, Cestoda, Trematoda, and Acanthocephala including economically important members of the orders Strongylida, Ascaridida, Oxyurida, Rhabditida, Spirurida, and Enoplida such as but not limited to economically important agricultural pests (i.e. root knot nematodes in the genus *Meloidogyne*, lesion nematodes in the genus *Pratylenchus*, stubby root nematodes in the genus *Trichodorus*, etc.) and animal and human health pests (i.e. all economically important flukes, tapeworms, and roundworms, such as *Strongylus vulgaris* in horses, *Toxocara canis* in dogs, *Haemonchus contortus* in sheep, *Dirofilaria immitis* Leidy in dogs, *Anoplocephala perfoliata* in horses, *Fasciola hepatica* Linnaeus in ruminants, etc.).

Of note is use of a mixture of this invention for controlling silverleaf whitefly (*Bemisia argentifolii*), wherein one embodiment comprises using a mixture wherein the component (b) is a (b1) compound, e.g., imidacloprid, thiacloprid or thiamethoxam; a (b2) compound, e.g., thiodicarb; a (b3) compound, e.g., deltamethrin; a (b4) compound, e.g., buprofezin, cyromazine, hexaflumuron or novaluron; a (b7) compound, e.g., spinosad; a (b8) compound, e.g., fipronil; a (b9) compound, e.g., methoprene; a. (b12) compound, e.g., pyridaben; or a (b13) compound, e.g., cartap. Of further note is use of a mixture of this invention for controlling silverleaf whitefly (*Bemisia argentifolii*), wherein another embodiment comprises using a mixture wherein the component (b) is at least one invertebrate pest control agent (or salt thereof) from each of two different groups selected from (b1), (b2), (b3), (b4), (b5), (b6), (b7), (b8), (b9), (b10), (b11), (b12), (b13), (b14), (b15), (b16), (b17), (b18) and (b19).

Of note is use of a mixture of this invention for controlling western flower thrip (*Frankliniella occidentalis*), wherein one embodiment comprises using a mixture wherein the component (b) is a (b1) compound, e.g., imidacloprid; a (b4) compound, e.g., hexaflumuron; or a (b13) compound, e.g., cartap. Of further note is use of a mixture of this invention for controlling western flower thrip (*Frankliniella occidentalis*), wherein another embodiment comprises using a mixture wherein the component (b) is at least one invertebrate pest control agent (or salt thereof) from each of two different groups selected from (b1), (b2), (b3), (b4), (b5), (b6), (b7), (b8), (b9), (b10), (b11), (b12), (b13), (b14), (b15), (b16), (b17), (b18) and (b19).

Of note is use of a mixture of this invention for controlling potato leafhopper (*Empoasca fabae*), wherein one embodiment comprises using a mixture wherein the component (b) is a (b1) compound, e.g., dinotefuran, imidacloprid or nitenpyram; a (b2) compound, e.g., methomyl or oxamyl; a (b3) compound, e.g., deltamethrin, esfenvalerate or lambda-cyhalothrin; a (b4) compound, e.g., hexaflumuron, lufenuron or novaluron; a (b5) compound, e.g., methoxyfenozide; a (b7) compound, e.g., abamectin or spinosad; a (b9) compound, e.g., methoprene; a (b11) compound, e.g., amitraz; a (b12) compound, e.g., hydramethylnon or chlorfenapyr; a (b15) compound, flonicamid; or a (b16) compound, pymetrozine. Of further note is use of a mixture of this invention for controlling potato leafhopper (*Empoasca fabae*), wherein another embodiment comprises using a mixture wherein component (b) is at least one invertebrate pest control agent (or salt thereof) from each of two different groups selected from (b1), (b2), (b3), (b4), (b5), (b6), (b7), (b8), (b9), (b10), (b11), (b12), (b13), (b14), (b15), (b16), (b17), (b18) and (b19).

Of note is use of a mixture of this invention for controlling corn plant hopper (*Peregrinus maidis*), wherein one embodiment comprises using a mixture wherein the component (b) is a (b1) compound, e.g., dinotefuran or thiacloprid; a (b2) compound, e.g., triazamate; a (b3) compound, e.g., indoxacarb; a (b9) compound, e.g., fenoxycarb; a (b14) compound pyridalyl; a (b15) compound, flonicamid; a (b16) compound, pymetrozine; or a (b17) compound, dieldrin. Of further note is use of a mixture of this invention for controlling corn plant hopper (*Peregrinus maidis*), wherein another embodiment comprises using a mixture wherein the component (b) is at least one invertebrate pest control agent (or salt thereof) from each of two different groups selected from (b1), (b2), (b3), (b4), (b5), (b6), (b7), (b8), (b9), (b10), (b11), (b12), (b13), (b14), (b15), (b16), (b17), (b18) and (b19).

Of note is use of a mixture of this invention for controlling cotton melon aphid (*Aphis gossypii*), wherein one embodiment comprises using a mixture wherein the component (b) is a (b1) compound, e.g., imidacloprid, nitenpyram, thiacloprid or thiamethoxam; a (b2) compound, e.g., oxamyl; a (b3) compound, e.g., lambda-cyhalothrin; a (b4) compound, e.g., novaluron; a (b7) compound, e.g., abamectin; a (b8) compound, e.g., fipronil; a (b9) compound, e.g., fenoxycarb, methoprene or pyriproxyfen; a (b11) compound, e.g., amitraz; a (b12) compound, e.g., chlorfenapyr or pyridaben; a (b13) compound, e.g., cartap; a (b15) compound, flonicamid; a (b16) compound, pymetrozine; or a (b17) compound, dieldrin. Of further note is use of a mixture of this invention for controlling cotton melon aphid (*Aphis gossypii*), wherein another embodiment comprises using a mixture wherein the component (b) is at least one invertebrate pest control agent (or salt thereof) from each of two different groups selected from (b1), (b2), (b3), (b4), (b5), (b6), (b7), (b8), (b9), (b10), (b11), (b12), (b13), (b14), (b15), (b16), (b17), (b18) and (b19).

Of note is use of a mixture of this invention for controlling green peach aphid (*Myzus persicae*), wherein one embodiment comprises using a mixture wherein the component (b) is a (b1) compound, e.g., acetamiprid, dinotefuran or imidacloprid; a (b2) compound, e.g., oxamyl; a (b7) compound, e.g., spinosad; a (b9) compound, e.g., methoprene; a (b15) compound, flonicamid; a (b16) compound, pymetrozine; or a (b17) compound, dieldrin. Of further note is use of a mixture of this invention for controlling green peach aphid (*Myzus persicae*), wherein another embodiment comprises using a mixture wherein the component (b) is at least one invertebrate pest control agent (or salt thereof) from each of two different groups selected from (b1), (b2), (b3), (b4), (b5), (b6), (b7), (b8), (b9), (b10), (b11), (b12), (b13), (b14), (b15), (b16), (b17), (b18) and (b19).

Of note is use of a mixture of this invention for controlling beet armyworm (*Spodoptera exigua*), wherein one embodiment comprises using a mixture wherein the component (b) is a (b1) compound, e.g., imidacloprid; a (b2) compound, e.g., methomyl or oxamyl; or a (b3) compound, e.g., indoxacarb. Of further note is use of a mixture of this invention for controlling beet armyworm (*Spodoptera exigua*), wherein another embodiment comprises using a mixture wherein the component (b) is at least one invertebrate pest control agent (or salt thereof) from each of two different groups selected from (b1), (b2), (b3), (b4), (b5), (b6), (b7), (b8), (b9), (b10), (b11), (b12), (b13), (b14), (b15), (b16), (b17), (b18) and (b19).

Of note is use of a mixture of this invention for controlling cabbage looper (*Trichoplusia ni*), wherein one embodiment comprises using a mixture wherein the component (b) is a (b1) compound, e.g., imidacloprid; a (b2) compound, e.g., methomyl or oxamyl; or a (b3) compound, e.g., indoxacarb. Of further note is use of a mixture of this invention for controlling cabbage looper (*Trichoplusia ni*), wherein another embodiment comprises using a mixture wherein the component (b) is at least one invertebrate pest control agent (or salt thereof) from each of two different groups selected from (b1), (b2), (b3), (b4), (b5), (b6), (b7), (b8), (b9), (b10), (b11), (b12), (b13), (b14), (b15), (b16), (b17), (b18) and (b19).

Of note is use of a mixture of this invention for controlling diamondback moth (*Plutella xylostella*), wherein one embodiment comprises using a mixture wherein the component (b) is a (b1) compound, e.g., imidacloprid; a (b2) compound, e.g., methomyl or oxamyl; a (b3) compound, e.g., indoxacarb; or a (b15) compound, flonicamid. Of further note is use of a mixture of this invention for controlling diamondback moth (*Plutella xylostella*), wherein another embodiment comprises using a mixture wherein the component (b) is at least one invertebrate pest control agent (or salt thereof) from each of two different groups selected from (b1), (b2), (b3), (b4), (b5), (b6), (b7), (b8), (b9), (b10), (b11), (b12), (b13), (b14), (b15), (b16), (b17), (b18) and (b19).

Invertebrate pests are controlled in agronomic and nonagronomic applications by applying a composition or mixture of this invention, in an effective amount, to the environment of the pests, including the agronomic and/or nonagronomic locus of infestation, to the area to be protected, or directly on the pests to be controlled. Agronomic applications include protecting a field crop from invertebrate pests typically by applying a composition or a mixture of the invention to the seed of the crop before the planting, to the foliage, stems, flowers and/or fruit of crop plants, or to the soil or other growth medium before or after the crop is planted. Nonagronomic applications refer to invertebrate pest control in the areas other than fields of crop plants. Nonagronomic applications include control of invertebrate pests in stored grains, beans and other foodstuffs, and in textiles such as clothing and carpets. Nonagronomic applications also include invertebrate pest control in ornamental plants, forests, in yards, along road sides and railroad rights of way, and on turf such as lawns, golf courses and pastures. Nonagronomic applications also include invertebrate pest control in houses and other buildings which may be occupied by humans and/or companion, farm, ranch, zoo or other animals Nonagronomic applications also include the control of pests such as termites that can damage wood or other structural materials used in buildings. Nonagronomic applications also include protecting human and animal health by controlling invertebrate pests that are parasitic or transmit infectious diseases. Such pests include, for example, chiggers, ticks, lice, mosquitoes, flies and fleas.

Therefore, the present invention further comprises a method for controlling an invertebrate pest in agronomic and/or nonagronomic applications, comprising contacting the invertebrate pest or its environment with a biologically effective amount of a mixture comprising the compound of Formula 1, an N-oxide or salt thereof; and at least one invertebrate pest control agent (or salt thereof) selected from the group consisting of (b1), (b2), (b3), (b4), (b5), (b6), (b7), (b8), (b9), (b10), (b11), (b12), (b13), (b14), (b15), (b16), (b17), (b18) and (b19). Examples of suitable compositions comprising an effective amount of the compound of Formula 1 and an effective amount of a component (b) include granular compositions wherein the component (b) is present on the same granule as the compound of Formula 1, an N-oxide or a salt thereof or on granules separate from those of the compound of Formula 1, an N-oxide or a salt thereof. Of note is an embodiment wherein component (b) is a (b1) compound, e.g. imidacloprid, a (b2) compound, e.g., methomyl or oxamyl, or a (b3) compound, e.g., indoxacarb or component (b) comprises at least one invertebrate pest control agent (or salt thereof) from each of two different groups selected from (b1), (b2), (b3), (b4), (b5), (b6), (b7), (b8), (b9), (b10), (b11), (b12), (b13), (b14), (b15), (b16), (b17), (b18) and (b19).

One embodiment of a method of contact is by spraying. Alternatively, a granular composition comprising a mixture or composition of the invention can be applied to the plant foliage or the soil. Mixtures and compositions of this invention are also effectively delivered through plant uptake by contacting the plant with a mixture or composition of this invention comprising the compound of Formula 1, an N-oxide or a salt thereof and an invertebrate pest control agent of component (b) applied as a soil drench of a liquid formulation, a granular formulation to the soil, a nursery box treatment or a dip of transplants. Of note is a composition of the present invention in the form of a soil drench liquid formulation. Also of note is a method for controlling an invertebrate pest comprising contacting the soil environment of the invertebrate pest with a biologically effective amount of the mixture of the present invention. Of further note are such methods wherein the mixture is of Embodiment 1-4, 6, 7, 9, 10, 15-20, 22, 23, 25, 26, 28-33, 35, 36, 38-45 or 46.

Mixtures and compositions of this invention are also effective by topical application to the locus of infestation. Other methods of contact include application of a mixture or composition of the invention by direct and residual sprays, aerial sprays, gels, seed coatings, microencapsulations, systemic uptake, baits, eartags, boluses, foggers, fumigants, aerosols, dusts and many others. One embodiment of a method of contact is a dimensionally stable fertilizer granule, stick or tablet comprising a mixture or composition of the invention. The compositions and mixtures of this invention can also be impregnated into materials for fabricating invertebrate control devices (e.g., insect netting). Seed coatings can be applied to all types of seeds, including those from which plants genetically transformed to express specialized traits will germinate. Representative examples include those expressing proteins toxic to invertebrate pests, such as *Bacillus thuringiensis* toxin or those expressing herbicide resistance, such as "Roundup Ready" seed. A mixture or composition of this invention can be incorporated into a bait composition that is consumed by an invertebrate pest or used within a device such as a trap, bait station, and the like. Such a bait composition can be in the form of granules which comprise (a) active ingredients, namely the compound of Formula 1, an N-oxide, or salt thereof; (b) an invertebrate pest control agent or salt thereof selected from the group consisting of (b1), (b2), (b3), (b4), (b5), (b6), (b7), (b8), (b9), (b10), (b11), (b12), (b13), (b14), (b15), (b16), (b17), (b18) and (b19); (c) one or more food materials; optionally (d) an attractant, and optionally (e) one or more humectants. Of note are granules or bait compositions which comprise between about 0.001-5% active ingredients, about 40-99% food material and/or attractant; and optionally about 0.05-10% humectants, which are effective in controlling soil invertebrate pests at very low application rates, particularly at doses of active ingredient that are lethal by ingestion rather than by direct contact. Some food materials can function both as a food source and an attractant. Food materials include carbohydrates, proteins and lipids. Examples of food materials are vegetable flour, sugar, starches, animal fat, vegetable oil, yeast extracts and milk solids. Examples of attractants are odorants and flavorants, such as fruit or plant extracts, perfume, or other animal or plant component, pheromones or other agents known to attract a target invertebrate pest. Examples of humectants, i.e. moisture retaining agents, are glycols and other polyols, glycerine and sorbitol. Of note is a bait composition (and a method utilizing such a bait composition) used to control at least one invertebrate pest selected from the group consisting of ants, termites and cockroaches, including individually or in combinations. A device for controlling an invertebrate pest can comprise the present bait composition and a housing adapted to receive the bait composition, wherein the housing has at least one opening sized to permit the invertebrate pest to pass through the opening so the invertebrate pest can gain access to the bait composition from a location outside the housing, and wherein the housing is further adapted to be placed in or near a locus of potential or known activity for the invertebrate pest.

The mixtures and compositions of this invention can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of the mixture or composition of the present invention. Combinations with spray oils, spray oil concentrates, spreader stickers, adjuvants, other solvents, and synergists such as piperonyl butoxide often enhance compound efficacy. For nonagronomic uses such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a mixture or composition of the present invention and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one invertebrate pest selected from the group consisting of mosquitoes, black flies, stable flies, deer flies, horse flies, wasps, yellow jackets, hornets, ticks, spiders, ants, gnats, and the like, including individually or in combinations.

The rate of application required for effective control (i.e. "biologically effective amount") will depend on such factors as the species of invertebrate to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredients per hectare are sufficient to control pests in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of invertebrate pest control.

Synergism has been described as "the cooperative action of two components (e.g., component (a) and component (b)) in a mixture, such that the total effect is greater or more prolonged than the sum of the effects of the two (or more) taken independently" (see P. M. L. Tames, *Neth. J. Plant Pathology* 1964, 70, 73-80). Mixtures containing the compound of Formula 1 together with other invertebrate pest control agents are found to exhibit synergistic effects against certain important invertebrate pests.

The presence of a synergistic effect between two active ingredients is established with the aid of the Colby equation (see S. R. Colby, "Calculating Synergistic and Antagonistic Responses of Herbicide Combinations", *Weeds*, 1967, 15, 20-22):

$$p = A + B - \left[\frac{A \times B}{100}\right]$$

Using the method of Colby, the presence of a synergistic interaction between two active ingredients is established by first calculating the predicted activity, p, of the mixture based on activities of the two components applied alone. If p is lower than the experimentally established effect, synergism has occurred. If p is equal or higher than the experimentally established effect, the interaction between the two components is characterized to be only additive or antagonism. In the equation above, A is the observed result of one component applied alone at rate x. The B term is the observed result of the second component applied at rate y. The equation estimates p, the observed result of the mixture of A at rate x with B at rate y if their effects are strictly additive and no interaction has occurred. To use the Colby equation the active ingredients of the mixture are applied in the test separately as well as in combination.

Biological Examples of the Invention

The following tests demonstrate the control efficacy of mixtures or compositions of this invention on specific pests.

The pest control protection afforded by the mixtures or compositions is not limited, however, to these species. The analysis of synergism or antagonism between the mixtures or compositions was determined using Colby's equation. The average % mortality data for the test compounds alone were inserted into the Colby's equation. If the observed (obs) average % mortality was higher than "p", the expected % mortality, the mixture or composition had synergistic effects. If the observed average % mortality was equal to or lower than the expected mortality, the mixture or composition either had no synergistic effect or an antagonistic effect. In these tests, Compound 1 (Cpd 1) is the compound of Formula 1.

Test A

For evaluating control of silverleaf whitefly (*Bemisia argentifolii* Bellows and Perring) through contact and/or systemic means, each test unit consisted of a small open container with a 12- to 14-day-old cotton plant inside. This was pre-infested by placing test units into cages infested with adult whiteflies so that oviposition on the cotton leaves could occur. The adults were removed from the plants with an air-blast nozzle, and the test units were capped. The test units were then stored 2 to 3 days before spraying.

Test compounds were formulated using a solution containing 10% acetone, 90% water and 300 ppm X-77® Spreader Lo-Foam Formula non-ionic surfactant containing alkylarylpolyoxyethylene, free fatty acids, glycols and 2-propanol (Loveland Industries, Inc.) to provide the desired concentration in ppm. Formulated test solutions were then applied in 1 mL volumes through a SUJ2 atomizer nozzle with 1/8 JJ custom body (Spraying Systems Co.) positioned 1.27 cm (0.5 inches) above the top of each test unit.

The results for all experimental compositions in this test were replicated three times. After spraying of the formulated test composition, each test unit was allowed to dry for 1 hour and the cap removed. The test units were held for 13 days in a growth chamber at 28° C. and 50-70% relative humidity. Each test unit was then assessed for insect mortality using a binocular microscope; the results are listed in Tables 2A and 2B.

TABLE 2A

Silverleaf Whitefly

| Compound 1 (ppm) | Imidacloprid (ppm) | Ratio | % Mortality (observed) | % Mortality (calculated) |
|---|---|---|---|---|
| 6 | 0 | — | 0 | — |
| 8 | 0 | — | 4 | — |
| 10 | 0 | — | 1 | — |
| 0 | 10 | — | 1 | — |
| 0 | 22 | — | 2 | — |
| 0 | 48 | — | 25 | — |
| 6 | 10 | 1:1.7 | 24 | 1 |
| 6 | 22 | 1:3.7 | 46 | 2 |
| 6 | 48 | 1:8.0 | 83 | 25 |
| 8 | 10 | 1:1.3 | 49 | 5 |
| 8 | 22 | 1:2.8 | 59 | 6 |
| 8 | 48 | 1:6 | 87 | 28 |
| 10 | 10 | 1:1 | 21 | 2 |
| 10 | 22 | 1:2.2 | 68 | 3 |
| 10 | 48 | 1:4.8 | 59 | 26 |

TABLE 2B

| Silverleaf Whitefly | rate (ppm) | % mortality (obs) | rate (ppm) | % mortality (obs) | rate (ppm) | % mortality (obs) |
|---|---|---|---|---|---|---|
| Compound 1 | 6 | 3 | 8 | 3 | 10 | 5 |
| Methomyl | 10 | 4 | 100 | 3 | 1000 | 6 |
| Cpd 1 + Methomyl | 6 + 10 | 8 | 8 + 10 | 0 | 10 + 10 | 0 |
| Cpd 1 + Methomyl | 6 + 100 | 4 | 8 + 100 | 0 | 10 + 100 | 0 |
| Cpd 1 + Methomyl | 6 + 1000 | 5 | 8 + 1000 | 9 | 10 + 1000 | 6 |
| Amitraz | 500 | 5 | 1000 | 0 | 2000 | 0 |
| Cpd 1 + Amitraz | 6 + 500 | 0 | 8 + 500 | 0 | 10 + 500 | 1 |
| Cpd 1 + Amitraz | 6 + 1000 | 0 | 8 + 1000 | 0 | 10 + 1000 | 0 |
| Cpd 1 + Amitraz | 6 + 2000 | 0 | 8 + 2000 | 0 | 10 + 2000 | 0 |
| Thiamethoxam | 5 | 15 | 15 | 78 | 30 | 92 |
| Cpd 1 + Thiamethoxam | 6 + 5 | 43* | 8 + 5 | 28* | 10 + 5 | 72* |
| Cpd 1 + Thiamethoxam | 6 + 15 | 93* | 8 + 15 | 80* | 10 + 15 | 60 |
| Cpd 1 + Thiamethoxam | 6 + 30 | 99* | 8 + 30 | 96* | 10 + 30 | 100* |
| Pyridaben | 20 | 21 | 30 | 55 | 50 | 73 |
| Cpd 1 + Pyridaben | 6 + 20 | 4 | 8 + 20 | 4 | 10 + 20 | 18 |
| Cpd 1 + Pyridaben | 6 + 30 | 18 | 8 + 30 | 38 | 10 + 30 | 47 |
| Cpd 1 + Pyridaben | 6 + 50 | 100* | 8 + 50 | 100* | 10 + 50 | 100* |
| Flonicamid | 0.1 | 2 | 0.2 | 2 | 0.5 | 2 |
| Cpd 1 + Flonicamid | 6 + 0.1 | 0 | 8 + 0.1 | 0 | 10 + 0.1 | 5 |
| Cpd 1 + Flonicamid | 6 + 0.2 | 0 | 8 + 0.2 | 0 | 10 + 0.2 | 0 |
| Cpd 1 + Flonicamid | 6 + 0.5 | 0 | 8 + 0.5 | 2 | 10 + 0.5 | 4 |
| Dieldrin | 10 | 0 | 100 | 0 | 1000 | 0 |
| Cpd 1 + Dieldrin | 6 + 10 | 1 | 8 + 10 | 0 | 10 + 10 | 0 |
| Cpd 1 + Dieldrin | 6 + 100 | 0 | 8 + 100 | 0 | 10 + 100 | 0 |
| Cpd 1 + Dieldrin | 6 + 1000 | 0 | 8 + 1000 | 0 | 10 + 1000 | 0 |
| Spinosad | 100 | 66 | 150 | 69 | 300 | 95 |
| Cpd 1 + Spinosad | 6 + 100 | 75* | 8 + 100 | 88* | 10 + 100 | 78* |
| Cpd 1 + Spinosad | 6 + 150 | 96* | 8 + 150 | 89* | 10 + 150 | 96* |
| Cpd 1 + Spinosad | 6 + 300 | 100* | 8 + 300 | 100* | 10 + 300 | 100* |
| Fipronil | 50 | 1 | 100 | 0 | 1000 | 13 |
| Cpd 1 + Fipronil | 6 + 50 | 5 | 8 + 50 | 2 | 10 + 50 | 13 |
| Cpd 1 + Fipronil | 6 + 100 | 2 | 8 + 100 | 26* | 10 + 100 | 19* |
| Cpd 1 + Fipronil | 6 + 1000 | 16 | 8 + 1000 | 16 | 10 + 1000 | 23 |
| Pyriproxyfen | 10 | 100 | 15 | 100 | 20 | 100 |
| Cpd 1 + Pyriproxyfen | 6 + 10 | 77 | 8 + 10 | 85 | 10 + 10 | 100 |
| Cpd 1 + Pyriproxyfen | 6 + 15 | 98 | 8 + 15 | 100 | 10 + 15 | 100 |
| Cpd 1 + Pyriproxyfen | 6 + 20 | 99 | 8 + 20 | 90 | 10 + 20 | 100 |

TABLE 2B-continued

| Silverleaf Whitefly | rate (ppm) | % mortality (obs) | rate (ppm) | % mortality (obs) | rate (ppm) | % mortality (obs) |
|---|---|---|---|---|---|---|
| Pymetrozine | 10 | 3 | 100 | 7 | 1000 | 52 |
| Cpd 1 + Pymetrozine | 6 + 10 | 0 | 8 + 10 | 0 | 10 + 10 | 0 |
| Cpd 1 + Pymetrozine | 6 + 100 | 3 | 8 + 100 | 0 | 10 + 100 | 0 |
| Cpd 1 + Pymetrozine | 6 + 1000 | 0 | 8 + 1000 | 0 | 10 + 1000 | 1 |
| Buprofezin | 300 | 75 | 500 | 65 | 1000 | 96 |
| Cpd 1 + Buprofezin | 6 + 300 | 57 | 8 + 300 | 99* | 10 + 300 | 98* |
| Cpd 1 + Buprofezin | 6 + 500 | 93* | 8 + 500 | 97* | 10 + 500 | 96* |
| Cpd 1 + Buprofezin | 6 + 1000 | 99* | 8 + 1000 | 100* | 10 + 1000 | 98* |
| Chlorfenapyr | 10 | 6 | 100 | 14 | 1000 | 18 |
| Cpd 1 + Chlorfenapyr | 6 + 10 | 8 | 8 + 10 | 10* | 10 + 10 | 1 |
| Cpd 1 + Chlorfenapyr | 6 + 100 | 2 | 8 + 100 | 1 | 10 + 100 | 3 |
| Cpd 1 + Chlorfenapyr | 6 + 1000 | 35* | 8 + 1000 | 49* | 10 + 1000 | 13 |
| Chlorpyrifos | 500 | 0 | 1000 | 0 | 2000 | 0 |
| Cpd 1 + Chlorpyrifos | 6 + 500 | 4 | 8 + 500 | 1 | 10 + 500 | 8 |
| Cpd 1 + Chlorpyrifos | 6 + 1000 | 1 | 8 + 1000 | 1 | 10 + 1000 | 7 |
| Cpd 1 + Chlorpyrifos | 6 + 2000 | 7 | 8 + 2000 | 2 | 10 + 2000 | 2 |
| Cyromazine | 10 | 1 | 100 | 2 | 1000 | 2 |
| Cpd 1 + Cyromazine | 6 + 10 | 41* | 8 + 10 | 84* | 10 + 10 | 79* |
| Cpd 1 + Cyromazine | 6 + 100 | 63* | 8 + 100 | 75* | 10 + 100 | 88* |
| Cpd 1 + Cyromazine | 6 + 1000 | 51* | 8 + 1000 | 66* | 10 + 1000 | 91* |
| Fenoxycarb | 2 | 0 | 10 | 0 | 20 | 21 |
| Cpd 1 + Fenoxycarb | 6 + 2 | 0 | 8 + 2 | 2 | 10 + 2 | 0 |
| Cpd 1 + Fenoxycarb | 6 + 10 | 4 | 8 + 10 | 11 | 10 + 10 | 14 |
| Cpd 1 + Fenoxycarb | 6 + 20 | 29* | 8 + 20 | 35* | 10 + 20 | 33* |
| Methoprene | 500 | 11 | 1000 | 22 | 2000 | 60 |
| Cpd 1 + Methoprene | 6 + 500 | 3 | 8 + 500 | 9 | 10 + 500 | 17* |
| Cpd 1 + Methoprene | 6 + 1000 | 52* | 8 + 1000 | 59* | 10 + 1000 | 90* |
| Cpd 1 + Methoprene | 6 + 2000 | 63* | 8 + 2000 | 78* | 10 + 2000 | 97* |
| Indoxacarb | 1 | 0 | 3 | 0 | 10 | 0 |
| Cpd 1 + Indoxacarb | 6 + 1 | 0 | 8 + 1 | 0 | 10 + 1 | 0 |
| Cpd 1 + Indoxacarb | 6 + 3 | 0 | 8 + 3 | 0 | 10 + 3 | 0 |
| Cpd 1 + Indoxacarb | 6 + 10 | 0 | 8 + 10 | 0 | 10 + 10 | 0 |
| Thiodicarb | 100 | 1 | 1000 | 0 | 3000 | 6 |
| Cpd 1 + Thiodicarb | 6 + 100 | 7 | 8 + 100 | 8 | 10 + 100 | 8 |
| Cpd 1 + Thiodicarb | 6 + 1000 | 5 | 8 + 1000 | 7 | 10 + 1000 | 17* |
| Cpd 1 + Thiodicarb | 6 + 3000 | 39* | 8 + 3000 | 18 | 10 + 3000 | 11 |
| Tebufenozide | 100 | 2 | 1000 | 6 | 3000 | 7 |
| Cpd 1 + Tebufenozide | 6 + 100 | 26* | 8 + 100 | 10 | 10 + 100 | 15* |
| Cpd 1 + Tebufenozide | 6 + 1000 | 5 | 8 + 1000 | 1 | 10 + 1000 | 8 |
| Cpd 1 + Tebufenozide | 6 + 3000 | 3 | 8 + 3000 | 4 | 10 + 3000 | 20* |
| Deltamethrin | 30 | 2 | 40 | 0 | 50 | 1 |
| Cpd 1 + Deltamethrin | 6 + 30 | 6 | 8 + 30 | 4 | 10 + 30 | 13 |
| Cpd 1 + Deltamethrin | 6 + 40 | 3 | 8 + 40 | 21* | 10 + 40 | 17* |
| Cpd 1 + Deltamethrin | 6 + 50 | 3 | 8 + 50 | 14* | 10 + 50 | 16* |
| Oxamyl | 0.1 | 2 | 0.3 | 0 | 1 | 1 |
| Cpd 1 + Oxamyl | 6 + 0.1 | 1 | 8 + 0.1 | 2 | 10 + 0.1 | 4 |
| Cpd 1 + Oxamyl | 6 + 0.3 | 1 | 8 + 0.3 | 0 | 10 + 0.3 | 10* |
| Cpd 1 + Oxamyl | 6 + 1 | 2 | 8 + 1 | 11* | 10 + 1 | 7 |
| Hexaflumuron | 10 | 1 | 60 | 0 | 360 | 0 |
| Cpd 1 + Hexaflumuron | 6 + 10 | 37* | 8 + 10 | 41* | 10 + 10 | 90* |
| Cpd 1 + Hexaflumuron | 6 + 60 | 51* | 8 + 60 | 71* | 10 + 60 | 75* |
| Cpd 1 + Hexaflumuron | 6 + 360 | 78* | 8 + 360 | 75* | 10 + 360 | 75* |
| Acetamiprid | 1 | 3 | 5 | 45 | 20 | 83 |
| Cpd 1 + Acetamiprid | 6 + 1 | 13* | 8 + 1 | 1 | 10 + 1 | 4 |
| Cpd 1 + Acetamiprid | 6 + 5 | 39 | 8 + 5 | 50* | 10 + 5 | 45 |
| Cpd 1 + Acetamiprid | 6 + 20 | 91* | 8 + 20 | 93* | 10 + 20 | 87* |
| Cartap | 0.1 | 0 | 0.2 | 0 | 0.5 | 0 |
| Cpd 1 + Cartap | 6 + 0.1 | 1 | 8 + 0.1 | 14* | 10 + 0.1 | 11* |
| Cpd 1 + Cartap | 6 + 0.2 | 0 | 8 + 0.2 | 2 | 10 + 0.2 | 16* |
| Cpd 1 + Cartap | 6 + 0.5 | 16* | 8 + 0.5 | 2 | 10 + 0.5 | 25* |
| Esfenvalerate | 50 | 1 | 100 | 0 | 200 | 0 |
| Cpd 1 + Esfenvalerate | 6 + 50 | 5 | 8 + 50 | 1 | 10 + 50 | 4 |
| Cpd 1 + Esfenvalerate | 6 + 100 | 3 | 8 + 100 | 6 | 10 + 100 | 2 |
| Cpd 1 + Esfenvalerate | 6 + 200 | 2 | 8 + 200 | 12* | 10 + 200 | 0 |
| Thiacloprid | 15 | 40 | 25 | 83 | 35 | 61 |
| Cpd 1 + Thiacloprid | 6 + 15 | 81* | 8 + 15 | 66* | 10 + 15 | 97* |
| Cpd 1 + Thiacloprid | 6 + 25 | 89* | 8 + 25 | 75 | 10 + 25 | 93* |
| Cpd 1 + Thiacloprid | 6 + 35 | 99* | 8 + 35 | 100* | 10 + 35 | 99* |
| Lambda-cyhalothrin | 10 | 0 | 50 | 1 | 250 | 100 |
| Cpd 1 + Lambda-cyhalothrin | 6 + 10 | 0 | 8 + 10 | 2 | 10 + 10 | 11* |
| Cpd 1 + Lambda-cyhalothrin | 6 + 50 | 0 | 8 + 50 | 23* | 10 + 50 | 10* |
| Cpd 1 + Lambda-cyhalothrin | 6 + 250 | 6 | 8 + 250 | 14 | 10 + 250 | 89 |
| Hydramethylnon | 10 | 2 | 100 | 1 | 1000 | 0 |
| Cpd 1 + Hydramethylnon | 6 + 10 | 0 | 8 + 10 | 5 | 10 + 10 | 0 |
| Cpd 1 + Hydramethylnon | 6 + 100 | 0 | 8 + 100 | 1 | 10 + 100 | 3 |
| Cpd 1 + Hydramethylnon | 6 + 1000 | 0 | 8 + 1000 | 0 | 10 + 1000 | 2 |
| Methoxyfenozide | 2 | 1 | 10 | 2 | 50 | 1 |

TABLE 2B-continued

| Silverleaf Whitefly | rate (ppm) | % mortality (obs) | rate (ppm) | % mortality (obs) | rate (ppm) | % mortality (obs) |
|---|---|---|---|---|---|---|
| Cpd 1 + Methoxyfenozide | 6 + 2 | 1 | 8 + 2 | 0 | 10 + 2 | 2 |
| Cpd 1 + Methoxyfenozide | 6 + 10 | 0 | 8 + 10 | 0 | 10 + 10 | 4 |
| Cpd 1 + Methoxyfenozide | 6 + 50 | 6 | 8 + 50 | 3 | 10 + 50 | 4 |
| Nitenpyram | 20 | 53 | 30 | 84 | 40 | 85 |
| Cpd 1 + Nitenpyram | 6 + 20 | 59* | 8 + 20 | 61* | 10 + 20 | 47 |
| Cpd 1 + Nitenpyram | 6 + 30 | 56 | 8 + 30 | 79 | 10 + 30 | 55 |
| Cpd 1 + Nitenpyram | 6 + 40 | 64 | 8 + 40 | 99* | 10 + 40 | 91* |
| Pyridalyl | 10 | 0 | 25 | 0 | 100 | 0 |
| Cpd 1 + Pyridalyl | 6 + 10 | 0 | 8 + 10 | 0 | 10 + 10 | 0 |
| Cpd 1 + Pyridalyl | 6 + 25 | 0 | 8 + 25 | 0 | 10 + 25 | 0 |
| Cpd 1 + Pyridalyl | 6 + 100 | 1 | 8 + 100 | 0 | 10 + 100 | 1 |
| Dinotefuran | 10 | 74 | 25 | 97 | 100 | 100 |
| Cpd 1 + Dinotefuran | 6 + 10 | 4 | 8 + 10 | 3 | 10 + 10 | 19 |
| Cpd 1 + Dinotefuran | 6 + 25 | 72 | 8 + 25 | 74 | 10 + 25 | 88 |
| Cpd 1 + Dinotefuran | 6 + 100 | 100 | 8 + 100 | 99 | 10 + 100 | 98 |
| Novaluron | 2 | 2 | 10 | 0 | 250 | 28 |
| Cpd 1 + Novaluron | 6 + 2 | 5 | 8 + 2 | 8* | 10 + 2 | 3 |
| Cpd 1 + Novaluron | 6 + 10 | 25* | 8 + 10 | 1 | 10 + 10 | 11* |
| Cpd 1 + Novaluron | 6 + 250 | 72* | 8 + 250 | 67* | 10 + 250 | 41* |

*indicates the observed % mortality is higher than the calculated % mortality by Colby equation.

Test B

For evaluating control of the western flower thrip (*Frankliniella occidentalis* Pergande) through contact and/or systemic means, each test unit consisted of a small open container with a 5- to 7-day-old bean (var. Soleil) plant inside.

Test solutions were formulated and sprayed with 3 replications as described for Test A. After spraying, the test units were allowed to dry for 1 hour, 22 to 27 adult *thrips* were added to each unit and then a black, screened cap was placed on top. The test units were held for 7 days at 25° C. and 45-55% relative humidity. Each test unit was then visually assessed for insect mortality; the results are listed in Tables 3A and 3B.

TABLE 3A

Western Flower Thrips

| Compound 1 (ppm) | Imidacloprid (ppm) | Ratio | % Mortality (observed) | % Mortality (calculated) |
|---|---|---|---|---|
| 8 | 0 | — | 3 | — |
| 25 | 0 | — | 17 | — |
| 81 | 0 | — | 30 | — |
| 0 | 11 | — | 20 | — |
| 0 | 77 | — | 37 | — |
| 0 | 561 | — | 90 | — |
| 8 | 11 | 1:1.4 | 23 | 22 |
| 8 | 77 | 1:9.6 | 60 | 39 |
| 8 | 561 | 1:70 | 90 | 90 |
| 25 | 11 | 2.3:1 | 17 | 34 |
| 25 | 77 | 1:3.1 | 63 | 48 |
| 25 | 561 | 1:22.4 | 90 | 92 |
| 81 | 11 | 7.4:1 | 37 | 44 |
| 81 | 77 | 1.1:1 | 70 | 56 |
| 81 | 561 | 1:6.9 | 93 | 93 |

TABLE 3B

| Western Flower Thrip | rate (ppm) | % mortality (obs) | rate (ppm) | % mortality (obs) | rate (ppm) | % mortality (obs) |
|---|---|---|---|---|---|---|
| Compound 1 | 10 | 44 | 50 | 49 | 100 | 46 |
| Methomyl | 30 | 60 | 100 | 60 | 300 | 100 |
| Cpd 1 + Methomyl | 10 + 30 | 80* | 50 + 30 | 60 | 100 + 30 | 60 |
| Cpd 1 + Methomyl | 10 + 100 | 80* | 50 + 100 | 80 | 100 + 100 | 80* |
| Cpd 1 + Methomyl | 10 + 300 | 100 | 50 + 300 | 90 | 100 + 300 | 90 |
| Amitraz | 10 | 40 | 100 | 30 | 1000 | 20 |
| Cpd 1 + Amitraz | 10 + 10 | 70* | 50 + 10 | 40 | 100 + 10 | 60 |
| Cpd 1 + Amitraz | 10 + 100 | 60 | 50 + 100 | 70* | 100 + 100 | 60 |
| Cpd 1 + Amitraz | 10 + 1000 | 50 | 50 + 1000 | 30 | 100 + 1000 | 60* |
| Thiamethoxam | 5 | 20 | 50 | 80 | 250 | 90 |
| Cpd 1 + Thiamethoxam | 10 + 5 | 20 | 50 + 5 | 30 | 100 + 5 | 50 |
| Cpd 1 + Thiamethoxam | 10 + 70 | 70 | 50 + 70 | 40 | 100 + 70 | 60 |
| Cpd 1 + Thiamethoxam | 10 + 250 | 90 | 50 + 250 | 90 | 100 + 250 | 90 |
| Pyridaben | 10 | 30 | 80 | 50 | 200 | 60 |
| Cpd 1 + Pyridaben | 10 + 10 | 50 | 50 + 10 | 20 | 100 + 10 | 30 |
| Cpd 1 + Pyridaben | 10 + 80 | 50 | 50 + 80 | 40 | 100 + 80 | 20 |
| Cpd 1 + Pyridaben | 10 + 200 | 80* | 50 + 200 | 60 | 100 + 200 | 70 |
| Flonicamid | 10 | 20 | 100 | 80 | 1000 | 70 |
| Cpd 1 + Flonicamid | 10 + 10 | 40 | 50 + 10 | 60 | 100 + 10 | 40 |

TABLE 3B-continued

| Western Flower Thrip | rate (ppm) | % mortality (obs) | rate (ppm) | % mortality (obs) | rate (ppm) | % mortality (obs) |
|---|---|---|---|---|---|---|
| Cpd 1 + Flonicamid | 10 + 100 | 60 | 50 + 100 | 70 | 100 + 100 | 50 |
| Cpd 1 + Flonicamid | 10 + 1000 | 70 | 50 + 1000 | 70 | 100 + 1000 | 80 |
| Dieldrin | 10 | 10 | 100 | 20 | 1000 | 30 |
| Cpd 1 + Dieldrin | 10 + 10 | 20 | 50 + 10 | 20 | 100 + 10 | 20 |
| Cpd 1 + Dieldrin | 10 + 100 | 10 | 50 + 100 | 40 | 100 + 100 | 30 |
| Cpd 1 + Dieldrin | 10 + 1000 | 20 | 50 + 1000 | 30 | 100 + 1000 | 30 |
| Spinosad | 0.1 | 20 | 0.5 | 60 | 3 | 90 |
| Cpd 1 + Spinosad | 10 + 0.1 | 30 | 50 + 0.1 | 10 | 100 + 0.1 | 10 |
| Cpd 1 + Spinosad | 10 + 0.5 | 30 | 50 + 0.5 | 50 | 100 + 0.5 | 50 |
| Cpd 1 + Spinosad | 10 + 3 | 90 | 50 + 3 | 70 | 100 + 3 | 60 |
| Fipronil | 0.5 | 100 | 2 | 100 | 10 | 100 |
| Cpd 1 + Fipronil | 10 + 0.5 | 100 | 50 + 0.5 | 100 | 100 + 0.5 | 100 |
| Cpd 1 + Fipronil | 10 + 2 | 100 | 50 + 2 | 100 | 100 + 2 | 100 |
| Cpd 1 + Fipronil | 10 + 10 | 100 | 50 + 10 | 100 | 100 + 10 | 100 |
| Pyriproxyfen | 10 | 100 | 100 | 100 | 1000 | 100 |
| Cpd 1 + Pyriproxyfen | 10 + 10 | 100 | 50 + 10 | 100 | 100 + 10 | 100 |
| Cpd 1 + Pyriproxyfen | 10 + 100 | 100 | 50 + 100 | 100 | 100 + 100 | 100 |
| Cpd 1 + Pyriproxyfen | 10 + 1000 | 100 | 50 + 1000 | 100 | 100 + 1000 | 100 |
| Pymetrozine | 10 | 100 | 100 | 100 | 1000 | 100 |
| Cpd 1 + Pymetrozine | 10 + 10 | 100 | 50 + 10 | 100 | 100 + 10 | 100 |
| Cpd 1 + Pymetrozine | 10 + 100 | 100 | 50 + 100 | 100 | 100 + 100 | 100 |
| Cpd 1 + Pymetrozine | 10 + 1000 | 100 | 50 + 1000 | 100 | 100 + 1000 | 100 |
| Buprofezin | 10 | 20 | 100 | 20 | 1000 | 30 |
| Cpd 1 + Buprofezin | 10 + 10 | 20 | 50 + 10 | 10 | 100 + 10 | 30 |
| Cpd 1 + Buprofezin | 10 + 100 | 0 | 50 + 100 | 10 | 100 + 100 | 20 |
| Cpd 1 + Buprofezin | 10 + 1000 | 20 | 50 + 1000 | 20 | 100 + 1000 | 30 |
| Chlorfenapyr | 5 | 40 | 20 | 70 | 150 | 90 |
| Cpd 1 + Chlorfenapyr | 10 + 5 | 20 | 50 + 5 | 30 | 100 + 5 | 40 |
| Cpd 1 + Chlorfenapyr | 10 + 20 | 40 | 50 + 20 | 30 | 100 + 20 | 40 |
| Cpd 1 + Chlorfenapyr | 10 + 150 | 90 | 50 + 150 | 90 | 100 + 150 | 90 |
| Chlorpyrifos | 10 | 20 | 100 | 10 | 1000 | 10 |
| Cpd 1 + Chlorpyrifos | 10 + 10 | 20 | 50 + 10 | 40 | 100 + 10 | 10 |
| Cpd 1 + Chlorpyrifos | 10 + 100 | 20 | 50 + 100 | 10 | 100 + 100 | 10 |
| Cpd 1 + Chlorpyrifos | 10 + 1000 | 30 | 50 + 1000 | 10 | 100 + 1000 | 20 |
| Cyromazine | 200 | 70 | 500 | 80 | 1000 | 70 |
| Cpd 1 + Cyromazine | 10 + 200 | 20 | 50 + 200 | 70 | 100 + 200 | 80 |
| Cpd 1 + Cyromazine | 10 + 500 | 80 | 50 + 500 | 40 | 100 + 500 | 40 |
| Cpd 1 + Cyromazine | 10 + 1000 | 50 | 50 + 1000 | 70 | 100 + 1000 | 40 |
| Fenoxycarb | 10 | 40 | 100 | 70 | 1000 | 60 |
| Cpd 1 + Fenoxycarb | 10 + 10 | 20 | 50 + 10 | 60 | 100 + 10 | 70* |
| Cpd 1 + Fenoxycarb | 10 + 100 | 60 | 50 + 100 | 70 | 100 + 100 | 70 |
| Cpd 1 + Fenoxycarb | 10 + 1000 | 20 | 50 + 1000 | 40 | 100 + 1000 | 80* |
| Methoprene | 10 | 80 | 100 | 60 | 1000 | 70 |
| Cpd 1 + Methoprene | 10 + 10 | 50 | 50 + 10 | 50 | 100 + 10 | 70 |
| Cpd 1 + Methoprene | 10 + 100 | 40 | 50 + 100 | 50 | 100 + 100 | 80* |
| Cpd 1 + Methoprene | 10 + 1000 | 60 | 50 + 1000 | 70 | 100 + 1000 | 40 |
| Indoxacarb | 1 | 50 | 500 | 50 | 3000 | 50 |
| Cpd 1 + Indoxacarb | 10 + 1 | 60 | 50 + 1 | 60 | 100 + 1 | 60 |
| Cpd 1 + Indoxacarb | 10 + 500 | 50 | 50 + 500 | 40 | 100 + 500 | 60 |
| Cpd 1 + Indoxacarb | 10 + 3000 | 50 | 50 + 3000 | 60 | 100 + 3000 | 80* |
| Triazamate | 10 | 70 | 1000 | 80 | 3000 | 90 |
| Cpd 1 + Triazamate | 10 + 10 | 60 | 50 + 10 | 70 | 100 + 10 | 90* |
| Cpd 1 + Triazamate | 10 + 1000 | 70 | 50 + 1000 | 60 | 100 + 1000 | 80 |
| Cpd 1 + Triazamate | 10 + 3000 | 70 | 50 + 3000 | 80 | 100 + 3000 | 80 |
| Thiodicarb | 20 | 60 | 200 | 80 | 2000 | 1000 |
| Cpd 1 + Thiodicarb | 10 + 20 | 60 | 50 + 20 | 50 | 100 + 20 | 40 |
| Cpd 1 + Thiodicarb | 10 + 200 | 80 | 50 + 200 | 60 | 100 + 200 | 70 |
| Cpd 1 + Thiodicarb | 10 + 2000 | 90 | 50 + 2000 | 100 | 100 + 2000 | 90 |
| Tebufenozide | 100 | 70 | 1000 | 60 | 3000 | 60 |
| Cpd 1 + Tebufenozide | 10 + 100 | 50 | 50 + 100 | 70 | 100 + 100 | 90* |
| Cpd 1 + Tebufenozide | 10 + 1000 | 80 | 50 + 1000 | 70 | 100 + 1000 | 50 |
| Cpd 1 + Tebufenozide | 10 + 3000 | 70 | 50 + 3000 | 90* | 100 + 3000 | 60 |
| Deltamethrin | 10 | 70 | 1000 | 70 | 3000 | 50 |
| Cpd 1 + Deltamethrin | 10 + 10 | 50 | 50 + 10 | 70 | 100 + 10 | 70 |
| Cpd 1 + Deltamethrin | 10 + 1000 | 70 | 50 + 1000 | 70 | 100 + 1000 | 70 |
| Cpd 1 + Deltamethrin | 10 + 3000 | 70 | 50 + 3000 | 80 | 100 + 3000 | 70 |
| Oxamyl | 1 | 30 | 50 | 40 | 500 | 100 |
| Cpd 1 + Oxamyl | 10 + 1 | 20 | 50 + 1 | 40 | 100 + 1 | 70* |
| Cpd 1 + Oxamyl | 10 + 50 | 30 | 50 + 50 | 60 | 100 + 50 | 60 |
| Cpd 1 + Oxamyl | 10 + 500 | 100 | 50 + 500 | 100 | 100 + 500 | 100 |
| Acetamiprid | 1 | 70 | 100 | 90 | 3000 | 100 |
| Cpd 1 + Acetamiprid | 10 + 1 | 70 | 50 + 1 | 60 | 100 + 1 | 60 |
| Cpd 1 + Acetamiprid | 10 + 100 | 80 | 50 + 100 | 80 | 100 + 100 | 80 |
| Cpd 1 + Acetamiprid | 10 + 3000 | 100 | 50 + 3000 | 100 | 100 + 3000 | 100 |

TABLE 3B-continued

| Western Flower Thrip | rate (ppm) | % mortality (obs) | rate (ppm) | % mortality (obs) | rate (ppm) | % mortality (obs) |
|---|---|---|---|---|---|---|
| Cartap | 1 | 40 | 1000 | 100 | 3000 | 100 |
| Cpd 1 + Cartap | 10 + 1 | 100* | 50 + 1 | 100* | 100 + 1 | 100* |
| Cpd 1 + Cartap | 10 + 1000 | 100 | 50 + 1000 | 100 | 100 + 1000 | 100 |
| Cpd 1 + Cartap | 10 + 3000 | 100 | 50 + 3000 | 100 | 100 + 3000 | 100 |
| Esfenvalerate | 10 | 20 | 20 | 40 | 30 | 30 |
| Cpd 1 + Esfenvalerate | 10 + 10 | 40 | 50 + 10 | 60 | 100 + 10 | 20 |
| Cpd 1 + Esfenvalerate | 10 + 20 | 50 | 50 + 20 | 50 | 100 + 20 | 40 |
| Cpd 1 + Esfenvalerate | 10 + 30 | 40 | 50 + 30 | 50 | 100 + 30 | 10 |
| Thiacloprid | 1 | 20 | 100 | 30 | 3000 | 40 |
| Cpd 1 + Thiacloprid | 10 + 1 | 30 | 50 + 1 | 30 | 100 + 1 | 30 |
| Cpd 1 + Thiacloprid | 10 + 100 | 30 | 50 + 100 | 30 | 100 + 100 | 60 |
| Cpd 1 + Thiacloprid | 10 + 3000 | 60 | 50 + 3000 | 50 | 100 + 3000 | 70 |
| Lambda-cyhalothrin | 10 | 40 | 50 | 40 | 250 | 40 |
| Cpd 1 + Lambda-cyhalothrin | 10 + 10 | 40 | 50 + 10 | 40 | 100 + 10 | 40 |
| Cpd 1 + Lambda-cyhalothrin | 10 + 50 | 40 | 50 + 50 | 50 | 100 + 50 | 50 |
| Cpd 1 + Lambda-cyhalothrin | 10 + 250 | 30 | 50 + 250 | 40 | 100 + 250 | 60 |
| Hydramethylnon | 10 | 60 | 500 | 50 | 1000 | 40 |
| Cpd 1 + Hydramethylnon | 10 + 10 | 40 | 50 + 10 | 60 | 100 + 10 | 50 |
| Cpd 1 + Hydramethylnon | 10 + 500 | 40 | 50 + 500 | 60 | 100 + 500 | 30 |
| Cpd 1 + Hydramethylnon | 10 + 1000 | 40 | 50 + 1000 | 30 | 100 + 1000 | 40 |
| Clothianidin | 100 | 90 | 500 | 100 | 1000 | 100 |
| Cpd 1 + Clothianidin | 10 + 100 | 60 | 50 + 100 | 90 | 100 + 100 | 70 |
| Cpd 1 + Clothianidin | 10 + 500 | 80 | 50 + 500 | 80 | 100 + 500 | 90 |
| Cpd 1 + Clothianidin | 10 + 1000 | 100 | 50 + 1000 | 100 | 100 + 1000 | 100 |
| Lufenuron | 10 | 90 | 100 | 80 | 500 | 80 |
| Cpd 1 + Lufenuron | 10 + 10 | 90 | 50 + 10 | 100* | 100 + 10 | 90 |
| Cpd 1 + Lufenuron | 10 + 100 | 90 | 50 + 100 | 90 | 100 + 100 | 90 |
| Cpd 1 + Lufenuron | 10 + 500 | 90 | 50 + 500 | 100* | 100 + 500 | 90 |
| Abamectin | 1 | 100 | 10 | 100 | 100 | 100 |
| Cpd 1 + Abamectin | 10 + 1 | 100 | 50 + 1 | 100 | 100 + 1 | 100 |
| Cpd 1 + Abamectin | 10 + 10 | 100 | 50 + 10 | 100 | 100 + 10 | 100 |
| Cpd 1 + Abamectin | 10 + 100 | 100 | 50 + 100 | 100 | 100 + 100 | 100 |
| Methoxyfenozide | 10 | 60 | 100 | 60 | 500 | 60 |
| Cpd 1 + Methoxyfenozide | 10 + 10 | 50 | 50 + 10 | 60 | 100 + 10 | 50 |
| Cpd 1 + Methoxyfenozide | 10 + 50 | 40 | 50 + 50 | 50 | 100 + 50 | 40 |
| Cpd 1 + Methoxyfenozide | 10 + 500 | 60 | 50 + 500 | 60 | 100 + 500 | 70 |
| Nitenpyram | 5 | 20 | 50 | 50 | 500 | 80 |
| Cpd 1 + Nitenpyram | 10 + 5 | 30 | 50 + 5 | 30 | 100 + 5 | 40 |
| Cpd 1 + Nitenpyram | 10 + 50 | 50 | 50 + 50 | 50 | 100 + 50 | 40 |
| Cpd 1 + Nitenpyram | 10 + 500 | 90 | 50 + 500 | 80 | 100 + 500 | 90 |
| Pyridalyl | 5 | 30 | 50 | 60 | 500 | 100 |
| Cpd 1 + Pyridalyl | 10 + 5 | 50 | 50 + 5 | 50 | 100 + 5 | 30 |
| Cpd 1 + Pyridalyl | 10 + 50 | 60 | 50 + 50 | 50 | 100 + 50 | 50 |
| Cpd 1 + Pyridalyl | 10 + 500 | 90 | 50 + 500 | 100 | 100 + 500 | 90 |
| Dinotefuran | 0.5 | 50 | 20 | 60 | 100 | 70 |
| Cpd 1 + Dinotefuran | 10 + 0.5 | 40 | 50 + 0.5 | 70 | 100 + 0.5 | 80* |
| Cpd 1 + Dinotefuran | 10 + 20 | 40 | 50 + 20 | 80 | 100 + 20 | 80* |
| Cpd 1 + Dinotefuran | 10 + 100 | 60 | 50 + 100 | 80 | 100 + 100 | 80 |
| Novaluron | 1 | 50 | 100 | 50 | 1000 | 80 |
| Cpd 1 + Novaluron | 10 + 1 | 40 | 50 + 1 | 70 | 100 + 1 | 50 |
| Cpd 1 + Novaluron | 10 + 100 | 60 | 50 + 100 | 80* | 100 + 100 | 80* |
| Cpd 1 + Novaluron | 10 + 1000 | 60 | 50 + 1000 | 50 | 100 + 1000 | 70 |

*indicates the observed % mortality is higher than the calculated % mortality by Colby equation.

Test C

For evaluating control of potato leafhopper (*Empoasca fabae* Harris) through contact and/or systemic means, each test unit consisted of a small open container with a 5- to 6-day-old Longio bean plant (primary leaves emerged) inside. White sand was added to the top of the soil, and one of the primary leaves was excised prior to application. Test compounds were formulated and sprayed with 3 replications as described for Test A. After spraying, the test units were allowed to dry for 1 hour before they were infested with 5 potato leafhoppers (18- to 21-day-old adults). A black, screened cap was placed on the top of each container. The test units were held for 6 days in a growth chamber at 19-21° C. and 50-70% relative humidity. Each test unit was then visually assessed for insect mortality; the results are listed in Tables 4A and 4B.

TABLE 4A

| Potato Leafhopper | | | | |
|---|---|---|---|---|
| Compound 1 (ppm) | Imidacloprid (ppm) | Ratio | % Mortality (observed) | % Mortality (calculated) |
| 0.4 | 0 | — | 0 | — |
| 1.4 | 0 | — | 0 | — |
| 4.6 | 0 | — | 0 | — |
| 0 | 0.2 | — | 20 | — |
| 0 | 0.4 | — | 0 | — |
| 0 | 1 | — | 20 | — |
| 0.4 | 0.2 | 2:1 | 7 | 20 |
| 0.4 | 0.4 | 1:1 | 0 | 0 |
| 0.4 | 1 | 1:2.5 | 60 | 20 |
| 1.4 | 0.2 | 7:1 | 27 | 20 |
| 1.4 | 0.4 | 3.5:1 | 27 | 0 |

TABLE 4A-continued

Potato Leafhopper

| Compound 1 (ppm) | Imidacloprid (ppm) | Ratio | % Mortality (observed) | % Mortality (calculated) |
|---|---|---|---|---|
| 1.4 | 1 | 1.4:1 | 40 | 20 |
| 4.6 | 0.2 | 23:1 | 13 | 20 |
| 4.6 | 0.4 | 11.5:1 | 33 | 0 |
| 4.6 | 1 | 4.6:1 | 73 | 20 |

TABLE 4B

| Potato Leaf Hopper | rate (ppm) | % mortality (obs) | rate (ppm) | % mortality (obs) | rate (ppm) | % mortality (obs) |
|---|---|---|---|---|---|---|
| Compound 1 | 4 | 23 | 14 | 37 | 50 | 54 |
| Methomyl | 1 | 0 | 2 | 53 | 5 | 100 |
| Cpd 1 + Methomyl | 4 + 1 | 53* | 14 + 1 | 40 | 50 + 1 | 53 |
| Cpd 1 + Methomyl | 4 + 2 | 67* | 14 + 2 | 93* | 50 + 2 | 87* |
| Cpd 1 + Methomyl | 4 + 5 | 100 | 14 + 5 | 100 | 50 + 5 | 93 |
| Amitraz | 10 | 0 | 100 | 7 | 1000 | 13 |
| Cpd 1 + Amitraz | 4 + 10 | 0 | 14 + 10 | 40 | 50 + 10 | 40 |
| Cpd 1 + Amitraz | 4 + 100 | 7 | 14 + 100 | 93* | 50 + 100 | 80* |
| Cpd 1 + Amitraz | 4 + 1000 | 53* | 14 + 1000 | 87* | 50 + 1000 | 93* |
| Thiamethoxam | 0.1 | 80 | 0.2 | 100 | 0.4 | 100 |
| Cpd 1 + Thiamethoxam | 4 + 0.1 | 60 | 14 + 0.1 | 67 | 50 + 0.1 | 67 |
| Cpd 1 + Thiamethoxam | 4 + 0.2 | 73 | 14 + 0.2 | 73 | 50 + 0.2 | 60 |
| Cpd 1 + Thiamethoxam | 4 + 0.4 | 93 | 14 + 0.4 | 100 | 50 + 0.4 | 100 |
| Pyridaben | 1 | 0 | 2.5 | 13 | 10 | 100 |
| Cpd 1 + Pyridaben | 4 + 1 | 7 | 14 + 1 | 40 | 50 + 1 | 33 |
| Cpd 1 + Pyridaben | 4 + 2.5 | 20 | 14 + 2.5 | 33 | 50 + 2.5 | 47 |
| Cpd 1 + Pyridaben | 4 + 10 | 47 | 14 + 10 | 33 | 50 + 10 | 100 |
| Flonicamid | 100 | 100 | 400 | 100 | 1000 | 40 |
| Cpd 1 + Flonicamid | 4 + 100 | 100 | 14 + 100 | 100 | 50 + 100 | 100 |
| Cpd 1 + Flonicamid | 4 + 400 | 100 | 14 + 400 | 93 | 50 + 400 | 100 |
| Cpd 1 + Flonicamid | 4 + 1000 | 100 | 14 + 1000 | 100 | 50 + 1000 | 100 |
| Dieldrin | 2.5 | 27 | 5 | 100 | 10 | 100 |
| Cpd 1 + Dieldrin | 4 + 2.5 | 33 | 14 + 2.5 | 93* | 50 + 2.5 | 33 |
| Cpd 1 + Dieldrin | 4 + 5 | 67 | 14 + 5 | 100 | 50 + 5 | 100 |
| Cpd 1 + Dieldrin | 4 + 10 | 100 | 14 + 10 | 100 | 50 + 10 | 73 |
| Spinosad | 110 | 47 | 30 | 73 | 100 | 80 |
| Cpd 1 + Spinosad | 4 + 10 | 87* | 14 + 10 | 73* | 50 + 10 | 100* |
| Cpd 1 + Spinosad | 4 + 30 | 100* | 14 + 30 | 100* | 50 + 30 | 100* |
| Cpd 1 + Spmosad | 4 + 100 | 100* | 14 + 100 | 100* | 50 + 100 | 100* |
| Fipronil | 0.5 | 7 | 1 | 20 | 1.5 | 27 |
| Cpd 1 + Fipronil | 4 + 0.5 | 20 | 14 + 0.5 | 40 | 50 + 0.5 | 60 |
| Cpd 1 + Fipronil | 4 + 1 | 40 | 14 + 1 | 53 | 50 + 1 | 93* |
| Cpd 1 + Fipronil | 4 + 1.5 | 53* | 14 + 1.5 | 33 | 50 + 1.5 | 73 |
| Pyriproxyfen | 10 | 13 | 100 | 0 | 1000 | 7 |
| Cpd 1 + Pyriproxyfen | 4 + 10 | 13 | 14 + 10 | 53* | 50 + 10 | 53 |
| Cpd 1 + Pyriproxyfen | 4 + 100 | 33* | 14 + 100 | 33 | 50 + 100 | 53 |
| Cpd 1 + Pyriproxyfen | 4 + 1000 | 33* | 14 + 1000 | 53 | 50 + 1000 | 40 |
| Pymetrozine | 2 | 0 | 15 | 13 | 200 | 60 |
| Cpd 1 + Pymetrozine | 4 + 2 | 20 | 14 + 2 | 60* | 50 + 2 | 73* |
| Cpd 1 + Pymetrozine | 4 + 15 | 53* | 14 + 15 | 60* | 50 + 15 | 73* |
| Cpd 1 + Pymetrozine | 4 + 200 | 53 | 14 + 200 | 87* | 50 + 200 | 73 |
| Buprofezin | 10 | 20 | 100 | 20 | 1000 | 0 |
| Cpd 1 + Buprofezin | 4 + 10 | 0 | 14 + 10 | 13 | 50 + 10 | 13 |
| Cpd 1 + Buprofezin | 4 + 100 | 20 | 14 + 100 | 0 | 50 + 100 | 0 |
| Cpd 1 + Buprofezin | 4 + 1000 | 13 | 14 + 1000 | 0 | 50 + 1000 | 7 |
| Chlorfenapyr | 1 | 73 | 5 | 100 | 20 | 100 |
| Cpd 1 + Chlorfenapyr | 4 + 1 | 87* | 14 + 1 | 80 | 50 + 1 | 100* |
| Cpd 1 + Chlorfenapyr | 4 + 5 | 100 | 14 + 5 | 100 | 50 + 5 | 100 |
| Cpd 1 + Chlorfenapyr | 4 + 20 | 87 | 14 + 20 | 100 | 50 + 20 | 100 |
| Chlorpyrifos | 10 | 13 | 100 | 0 | 1000 | 7 |
| Cpd 1 + Chlorpyrifos | 4 + 10 | 7 | 14 + 10 | 7 | 50 + 10 | 13 |
| Cpd 1 + Chlorpyrifos | 4 + 100 | 0 | 14 + 100 | 0 | 50 + 100 | 20 |
| Cpd 1 + Chlorpyrifos | 4 + 1000 | 0 | 14 + 1000 | 13 | 50 + 1000 | 20 |
| Cyromazine | 10 | 7 | 100 | 0 | 1000 | 0 |
| Cpd 1 + Cyromazine | 4 + 10 | 7 | 14 + 10 | 7 | 50 + 10 | 60* |
| Cpd 1 + Cyromazine | 4 + 100 | 0 | 14 + 100 | 27 | 50 + 100 | 100* |
| Cpd 1 + Cyromazine | 4 + 1000 | 13 | 14 + 1000 | 27 | 50 + 1000 | 33 |
| Fenoxycarb | 10 | 0 | 100 | 20 | 1000 | 0 |
| Cpd 1 + Fenoxycarb | 4 + 10 | 7 | 14 + 10 | 13 | 50 + 10 | 40 |
| Cpd 1 + Fenoxycarb | 4 + 100 | 0 | 14 + 100 | 13 | 50 + 100 | 20 |
| Cpd 1 + Fenoxycarb | 4 + 1000 | 13 | 14 + 1000 | 27 | 50 + 1000 | 13 |
| Methoprene | 10 | 0 | 100 | 0 | 1000 | 0 |
| Cpd 1 + Methoprene | 4 + 10 | 20 | 14 + 10 | 100* | 50 + 10 | 93* |
| Cpd 1 + Methoprene | 4 + 100 | 13 | 14 + 100 | 73* | 50 + 100 | 93* |

TABLE 4B-continued

| Potato Leaf Hopper | rate (ppm) | % mortality (obs) | rate (ppm) | % mortality (obs) | rate (ppm) | % mortality (obs) |
|---|---|---|---|---|---|---|
| Cpd 1 + Methoprene | 4 + 1000 | 87* | 14 + 1000 | 80* | 50 + 1000 | 100* |
| Indoxacarb | 0.5 | 33 | 1 | 20 | 2 | 27 |
| Cpd 1 + Indoxacarb | 4 + 0.5 | 7 | 14 + 0.5 | 20 | 50 + 0.5 | 67 |
| Cpd 1 + Indoxacarb | 4 + 1 | 0 | 14 + 1 | 47 | 50 + 1 | 33 |
| Cpd 1 + Indoxacarb | 4 + 2 | 0 | 14 + 2 | 27 | 50 + 2 | 87* |
| Triazamate | 0.5 | 13 | 1 | 0 | 2 | 7 |
| Cpd 1 + Triazamate | 4 + 0.5 | 13 | 14 + 0.5 | 33 | 50 + 0.5 | 80* |
| Cpd 1 + Triazamate | 4 + 1 | 13 | 14 + 1 | 33 | 50 + 1 | 20 |
| Cpd 1 + Triazamate | 4 + 2 | 0 | 14 + 2 | 80* | 50 + 2 | 7 |
| Thiodicarb | 0.08 | 0 | 0.16 | 20 | 0.4 | 20 |
| Cpd 1 + Thiodicarb | 4 + 0.08 | 7 | 14 + 0.08 | 47* | 50 + 0.08 | 27 |
| Cpd 1 + Thiodicarb | 4 + 0.16 | 13 | 14 + 0.16 | 13 | 50 + 0.16 | 60 |
| Cpd 1 + Thiodicarb | 4 + 0.4 | 20 | 14 + 0.4 | 0 | 50 + 0.4 | 93* |
| Tebufenozide | 3 | 40 | 4 | 27 | 5 | 20 |
| Cpd 1 + Tebufenozide | 4 + 3 | 27 | 14 + 3 | 27 | 50 + 3 | 93* |
| Cpd 1 + Tebufenozide | 4 + 4 | 40 | 14 + 4 | 67* | 50 + 4 | 47 |
| Cpd 1 + Tebufenozide | 4 + 5 | 20 | 14 + 5 | 100* | 50 + 5 | 47 |
| Deltamethrin | 0.1 | 7 | 0.2 | 7 | 1 | 60 |
| Cpd 1 + Deltamethrin | 4 + 0.1 | 13 | 14 + 0.1 | 53* | 50 + 0.1 | 73* |
| Cpd 1 + Deltamethrin | 4 + 0.2 | 40 | 14 + 0.2 | 33 | 50 + 0.2 | 100* |
| Cpd 1 + Deltamethrin | 4 + 1 | 60 | 14 + 1 | 100* | 50 + 1 | 100* |
| Oxamyl | 0.1 | 20 | 2 | 20 | 100 | 100 |
| Cpd 1 + Oxamyl | 4 + 0.1 | 7 | 14 + 0.1 | 73* | 50 + 0.1 | 87* |
| Cpd 1 + Oxamyl | 4 + 2 | 7 | 14 + 2 | 33 | 50 + 2 | 60 |
| Cpd 1 + Oxamyl | 4 + 100 | 93 | 14 + 100 | 100 | 50 + 100 | 100 |
| Hexaflumuron | 100 | 13 | 1000 | 13 | 3000 | 27 |
| Cpd 1 + Hexaflumuron | 4 + 100 | 7 | 14 + 100 | 33 | 50 + 100 | 80* |
| Cpd 1 + Hexaflumuron | 4 + 1000 | 13 | 14 + 1000 | 80* | 50 + 1000 | 87* |
| Cpd 1 + Hexaflumuron | 4 + 3000 | 33 | 14 + 3000 | 53 | 50 + 3000 | 80* |
| Acetamiprid | 1 | 27 | 4 | 60 | 12 | 87 |
| Cpd 1 + Acetamiprid | 4 + 1 | 7 | 14 + 1 | 20 | 50 + 1 | 53 |
| Cpd 1 + Acetamiprid | 4 + 4 | 60 | 14 + 4 | 60 | 50 + 4 | 60 |
| Cpd 1 + Acetamiprid | 4 + 12 | 87 | 14 + 12 | 100* | 50 + 12 | 93 |
| Cartap | 0.1 | 20 | 1 | 73 | 10 | 100 |
| Cpd 1 + Cartap | 4 + 0.1 | 33 | 14 + 0.1 | 47 | 50 + 0.1 | 67 |
| Cpd 1 + Cartap | 4 + 1 | 60 | 14 + 1 | 73 | 50 + 1 | 47 |
| Cpd 1 + Cartap | 4 + 10 | 100 | 14 + 10 | 100 | 50 + 10 | 100 |
| Esfenvalerate | 0.5 | 47 | 1 | 80 | 2 | 27 |
| Cpd 1 + Esfenvalerate | 4 + 0.5 | 20 | 14 + 0.5 | 67* | 50 + 0.5 | 73 |
| Cpd 1 + Esfenvalerate | 4 + 1 | 67 | 14 + 1 | 87 | 50 + 1 | 93 |
| Cpd 1 + Esfenvalerate | 4 + 2 | 87* | 14 + 2 | 53 | 50 + 2 | 93* |
| Thiacloprid | 0.2 | 73 | 0.5 | 93 | 1.5 | 80 |
| Cpd 1 + Thiacloprid | 4 + 0.2 | 27 | 14 + 0.2 | 53 | 50 + 0.2 | 100* |
| Cpd 1 + Thiacloprid | 4 + 0.5 | 53 | 14 + 0.5 | 80 | 50 + 0.5 | 80 |
| Cpd 1 + Thiacloprid | 4 + 1.5 | 100* | 14 + 1.5 | 100* | 50 + 1.5 | 100* |
| Lambda-cyhalothrin | 0.016 | 73 | 0.08 | 0 | 0.4 | 87 |
| Cpd 1 + Lambda-cyhalothrin | 4 + 0.016 | 47 | 14 + 0.016 | 100* | 50 + 0.016 | 100* |
| Cpd 1 + Lambda-cyhalothrin | 4 + 0.08 | 47* | 14 + 0.08 | 93* | 50 + 0.08 | 87* |
| Cpd 1 + Lambda-cyhalothrin | 4 + 0.4 | 100* | 14 + 0.4 | 100* | 50 + 0.4 | 100* |
| Hydramethylnon | 0.01 | 0 | 1 | 27 | 2 | 60 |
| Cpd 1 + Hydramethylnon | 4 + 0.01 | 27 | 14 + 0.01 | 53* | 50 + 0.01 | 87* |
| Cpd 1 + Hydramethylnon | 4 + 1 | 20 | 14 + 1 | 73* | 50 + 1 | 100* |
| Cpd 1 + Hydramethylnon | 4 + 2 | 40 | 14 + 2 | 87* | 50 + 2 | 100* |
| Clothianidin | 10 | 93 | 100 | 100 | 1000 | 100 |
| Cpd 1 + Clothianidin | 4 + 10 | 100 | 14 + 10 | 100 | 50 + 10 | 100 |
| Cpd 1 + Clothianidin | 4 + 100 | 100 | 14 + 100 | 100 | 50 + 100 | 100 |
| Cpd 1 + Clothianidin | 4 + 1000 | 100 | 14 + 1000 | 100 | 50 + 1000 | 100 |
| Lufenuron | 0.08 | 40 | 0.4 | 53 | 2 | 40 |
| Cpd 1 + Lufenuron | 4 + 0.08 | 60* | 14 + 0.08 | 87* | 50 + 0.08 | 87* |
| Cpd 1 + Lufenuron | 4 + 0.4 | 47 | 14 + 0.4 | 67 | 50 + 0.4 | 73 |
| Cpd 1 + Lufenuron | 4 + 2 | 47 | 14 + 2 | 27 | 50 + 2 | 100* |
| Abamectin | 10 | 47 | 100 | 100 | 1000 | 100 |
| Cpd 1 + Abamectin | 4 + 10 | 87* | 14 + 10 | 93* | 50 + 10 | 93* |
| Cpd 1 + Abamectin | 4 + 100 | 100 | 14 + 100 | 100 | 50 + 100 | 100 |
| Cpd 1 + Abamectin | 4 + 1000 | 100 | 14 + 1000 | 100 | 50 + 1000 | 100 |
| Methoxyfenozide | 0.08 | 13 | 0.4 | 13 | 2 | 20 |
| Cpd 1 + Methoxyfenozide | 4 + 0.08 | 13 | 14 + 0.08 | 73* | 50 + 0.08 | 100* |
| Cpd 1 + Methoxyfenozide | 4 + 0.4 | 13 | 14 + 0.4 | 7 | 50 + 0.4 | 100* |
| Cpd 1 + Methoxyfenozide | 4 + 2 | 27 | 14 + 2 | 100* | 50 + 2 | 100* |
| Nitenpyram | 0.3 | 7 | 0.4 | 73 | 0.5 | 33 |
| Cpd 1 + Nitenpyram | 4 + 0.3 | 7 | 14 + 0.3 | 100* | 50 + 0.3 | 100* |
| Cpd 1 + Nitenpyram | 4 + 0.4 | 7 | 14 + 0.4 | 100* | 50 + 0.4 | 13 |
| Cpd 1 + Nitenpyram | 4 + 0.5 | 7 | 14 + 0.5 | 100* | 50 + 0.5 | 13 |
| Pyridalyl | 0.5 | 13 | 5 | 13 | 50 | 7 |
| Cpd 1 + Pyridalyl | 4 + 0.5 | 7 | 14 + 0.5 | 7 | 50 + 0.5 | 20 |
| Cpd 1 + Pyridalyl | 4 + 5 | 0 | 14 + 5 | 13 | 50 + 5 | 7 |
| Cpd 1 + Pyridalyl | 4 + 50 | 13 | 14 + 50 | 13 | 50 + 50 | 7 |

TABLE 4B-continued

| Potato Leaf Hopper | rate (ppm) | % mortality (obs) | rate (ppm) | % mortality (obs) | rate (ppm) | % mortality (obs) |
|---|---|---|---|---|---|---|
| Dinotefuran | 0.02 | 7 | 0.08 | 7 | 0.4 | 47 |
| Cpd 1 + Dinotefuran | 4 + 0.02 | 7 | 14 + 0.02 | 53* | 50 + 0.02 | 100* |
| Cpd 1 + Dinotefuran | 4 + 0.08 | 7 | 14 + 0.08 | 67* | 50 + 0.08 | 100* |
| Cpd 1 + Dinotefuran | 4 + 0.4 | 100* | 14 + 0.4 | 100* | 50 + 0.4 | 100* |
| Novaluron | 250 | 7 | 500 | 7 | 1000 | 0 |
| Cpd 1 + Novaluron | 4 + 250 | 7 | 14 + 250 | 60* | 50 + 250 | 67* |
| Cpd 1 + Novaluron | 4 + 500 | 13 | 14 + 500 | 67* | 50 + 500 | 100* |
| Cpd 1 + Novaluron | 4 + 1000 | 47* | 14 + 1000 | 67* | 50 + 1000 | 93* |

*indicates the observed % mortality is higher than the calculated % mortality by Colby equation.

Test D

For evaluating control of corn planthopper (*Peregrines maidis*) through contact and/or systemic means, each test unit consisted of a small open cylindrical container with a 3- to 4-day-old corn (maize) plant (spike) inside. White sand was added to the top of the soil prior to application. Test compounds were formulated and sprayed with 3 replications as described for Test A. After spraying, the test units were allowed to dry for 1 hour before they were post-infested with 10 to 20 corn planthoppers (18- to 20-day-old nymphs) by sprinkling them onto the sand with a salt shaker. A black, screened cap was placed on the top of each container. The test units were held for 6 days in a growth chamber at 19-21° C. and 50-70% relative humidity. Each test unit was then visually assessed for insect mortality; the results are listed in Tables 5A and 5B.

TABLE 5A

Corn Planthopper

| Compound 1 (ppm) | Imidacloprid (ppm) | Ratio | % Mortality (observed) | % Mortality (calculated) |
|---|---|---|---|---|
| 5 | 0 | — | 6 | — |
| 50 | 0 | — | 9 | — |
| 150 | 0 | — | 28 | — |
| 0 | 0.1 | — | 27 | — |
| 0 | 0.3 | — | 37 | — |
| 0 | 1 | — | 60 | — |
| 5 | 0.1 | 50:1 | 7 | 31 |
| 5 | 0.3 | 16.7:1 | 8 | 41 |
| 5 | 1 | 5:1 | 15 | 62 |
| 50 | 0.1 | 500:1 | 9 | 34 |
| 50 | 0.3 | 167:1 | 5 | 43 |
| 50 | 1 | 50:1 | 13 | 64 |
| 150 | 0.1 | 1500:1 | 8 | 47 |
| 150 | 0.3 | 500:1 | 5 | 55 |
| 150 | 1 | 150:1 | 13 | 71 |

TABLE 5B

| Corn Plant Hopper | rate (ppm) | % mortality (obs) | rate (ppm) | % mortality (obs) | rate (ppm) | % mortality (obs) |
|---|---|---|---|---|---|---|
| Compound 1 | 20 | 15 | 100 | 19 | 500 | 28 |
| Methomyl | 0.5 | 5 | 1 | 21 | 2 | 19 |
| Cpd 1 + Methomyl | 20 + 0.5 | 5 | 100 + 0.5 | 23 | 500 + 0.5 | 6 |
| Cpd 1 + Methomyl | 20 + 1 | 7 | 100 + 1 | 36 | 500 + 1 | 2 |
| Cpd 1 + Methomyl | 20 + 2 | 2 | 100 + 2 | 34 | 500 + 2 | 8 |
| Amitraz | 5 | 6 | 10 | 3 | 50 | 5 |
| Cpd 1 + Amitraz | 20 + 5 | 2 | 100 + 5 | 6 | 500 + 5 | 9 |
| Cpd 1 + Amitraz | 20 + 10 | 7 | 100 + 10 | 3 | 500 + 10 | 9 |
| Cpd 1 + Amitraz | 20 + 50 | 11 | 100 + 50 | 8 | 500 + 50 | 10 |
| Thiamethoxam | 0.2 | 100 | 0.4 | 100 | 0.6 | 100 |
| Cpd 1 + Thiamethoxam | 20 + 0.2 | 100 | 100 + 0.2 | 73 | 500 + 0.2 | 98 |
| Cpd 1 + Thiamethoxam | 20 + 0.4 | 100 | 100 + 0.4 | 100 | 500 + 0.4 | 100 |
| Cpd 1 + Thiamethoxam | 20 + 0.6 | 100 | 100 + 0.6 | 100 | 500 + 0.6 | 100 |
| Pyridaben | 2 | 10 | 2.5 | 2 | 3 | 2 |
| Cpd 1 + Pyridaben | 20 + 2 | 57* | 100 + 2 | 14 | 500 + 2 | 2 |
| Cpd 1 + Pyridaben | 20 + 2.5 | 48* | 100 + 2.5 | 16 | 500 + 2.5 | 5 |
| Cpd 1 + Pyridaben | 20 + 3 | 19* | 100 + 3 | 17 | 500 + 3 | 4 |
| Flonicamid | 2 | 52 | 15 | 42 | 150 | 90 |
| Cpd 1 + Flonicamid | 20 + 2 | 100* | 100 + 2 | 31 | 500 + 2 | 68 |
| Cpd 1 + Flonicamid | 20 + 15 | 100* | 100 + 15 | 50 | 500 + 15 | 100* |
| Cpd 1 + Flonicamid | 20 + 150 | 59 | 100 + 150 | 42 | 500 + 150 | 100 |
| Dieldrin | 0.1 | 37 | 0.2 | 57 | 0.3 | 71 |
| Cpd 1 + Dieldrin | 20 + 0.1 | 32 | 100 + 0.1 | 92* | 500 + 0.1 | 98* |
| Cpd 1 + Dieldrin | 20 + 0.2 | 88* | 100 + 0.2 | 88* | 500 + 0.2 | 10 |
| Cpd 1 + Dieldrin | 20 + 0.3 | 36 | 100 + 0.3 | 100* | 500 + 0.3 | 92* |
| Spinosad | 5 | 100 | 10 | 100 | 20 | 100 |

TABLE 5B-continued

| Corn Plant Hopper | rate (ppm) | % mortality (obs) | rate (ppm) | % mortality (obs) | rate (ppm) | % mortality (obs) |
|---|---|---|---|---|---|---|
| Cpd 1 + Spinosad | 20 + 5 | 100 | 100 + 5 | 100 | 500 + 5 | 100 |
| Cpd 1 + Spinosad | 20 + 10 | 100 | 100 + 10 | 100 | 500 + 10 | 100 |
| Cpd 1 + Spinosad | 20 + 20 | 100 | 100 + 20 | 100 | 500 + 20 | 100 |
| Fipronil | 0.5 | 5 | 1 | 41 | 1.5 | 15 |
| Cpd 1 + Fipronil | 20 + 0.5 | 29* | 100 + 0.5 | 5 | 500 + 0.5 | 6 |
| Cpd 1 + Fipronil | 20 + 1 | 22 | 100 + 1 | 7 | 500 + 1 | 11 |
| Cpd 1 + Fipronil | 20 + 1.5 | 15 | 100 + 1.5 | 9 | 500 + 1.5 | 8 |
| Pyriproxyfen | 10 | 0 | 100 | 8 | 1000 | 12 |
| Cpd 1 + Pyriproxyfen | 20 + 10 | 9 | 100 + 10 | 17 | 500 + 10 | 14 |
| Cpd 1 + Pyriproxyfen | 20 + 100 | 28* | 100 + 100 | 10 | 500 + 100 | 6 |
| Cpd 1 + Pyriproxyfen | 20 + 1000 | 11 | 100 + 1000 | 5 | 500 + 1000 | 3 |
| Pymetrozine | 2 | 51 | 10 | 29 | 30 | 89 |
| Cpd 1 + Pymetrozine | 20 + 2 | 20 | 100 + 2 | 32 | 500 + 2 | 62 |
| Cpd 1 + Pymetrozine | 20 + 10 | 50* | 100 + 10 | 58* | 500 + 10 | 84* |
| Cpd 1 + Pymetrozine | 20 + 30 | 81 | 100 + 30 | 89 | 500 + 30 | 100* |
| Buprofezin | 10 | 96 | 100 | 97 | 1000 | 98 |
| Cpd 1 + Buprofezin | 20 + 10 | 92 | 100 + 10 | 86 | 500 + 10 | 89 |
| Cpd 1 + Buprofezin | 20 + 100 | 94 | 100 + 100 | 90 | 500 + 100 | 98 |
| Cpd 1 + Buprofezin | 20 + 1000 | 93 | 100 + 1000 | 80 | 500 + 1000 | 96 |
| Chlorfenapyr | 1.5 | 31 | 2.5 | 15 | 3.5 | 11 |
| Cpd 1 + Chlorfenapyr | 20 + 1.5 | 68* | 100 + 1.5 | 41 | 500 + 1.5 | 64* |
| Cpd 1 + Chlorfenapyr | 20 + 2.5 | 18 | 100 + 2.5 | 42* | 500 + 2.5 | 38 |
| Cpd 1 + Chlorfenapyr | 20 + 3.5 | 34* | 100 + 3.5 | 39* | 500 + 3.5 | 8 |
| Chlorpyrifos | 0.1 | 46 | 0.2 | 24 | 0.3 | 19 |
| Cpd 1 + Chlorpyrifos | 20 + 0.1 | 40 | 100 + 0.1 | 29 | 500 + 0.1 | 53 |
| Cpd 1 + Chlorpyrifos | 20 + 0.2 | 47* | 100 + 0.2 | 20 | 500 + 0.2 | 33 |
| Cpd 1 + Chlorpyrifos | 20 + 0.3 | 14 | 100 + 0.3 | 50* | 500 + 0.3 | 58* |
| Cyromazine | 200 | 4 | 500 | 8 | 1000 | 8 |
| Cpd 1 + Cyromazine | 20 + 200 | 8 | 100 + 200 | 4 | 500 + 200 | 30 |
| Cpd 1 + Cyromazine | 20 + 500 | 20 | 100 + 500 | 8 | 500 + 500 | 17 |
| Cpd 1 + Cyromazine | 20 + 1000 | 6 | 100 + 1000 | 40* | 500 + 1000 | 15 |
| Fenoxycarb | 10 | 8 | 100 | 2 | 1000 | 5 |
| Cpd 1 + Fenoxycarb | 20 + 10 | 24 | 100 + 10 | 86* | 500 + 10 | 96* |
| Cpd 1 + Fenoxycarb | 20 + 100 | 49* | 100 + 100 | 78* | 500 + 100 | 100* |
| Cpd 1 + Fenoxycarb | 20 + 1000 | 19 | 100 + 1000 | 74* | 500 + 1000 | 61* |
| Methoprene | 15 | 100 | 50 | 65 | 150 | 86 |
| Cpd 1 + Methoprene | 20 + 15 | 100 | 100 + 15 | 73 | 500 + 15 | 100 |
| Cpd 1 + Methoprene | 20 + 50 | 16 | 100 + 50 | 17 | 500 + 50 | 93* |
| Cpd 1 + Methoprene | 20 + 150 | 74 | 100 + 150 | 2 | 500 + 150 | 87 |
| Indoxacarb | 50 | 3 | 500 | 4 | 3000 | 18 |
| Cpd 1 + Indoxacarb | 20 + 50 | 10 | 100 + 50 | 4 | 500 + 50 | 100* |
| Cpd 1 + Indoxacarb | 20 + 500 | 2 | 100 + 500 | 30 | 500 + 500 | 100* |
| Cpd 1 + Indoxacarb | 20 + 3000 | 4 | 100 + 3000 | 6 | 500 + 3000 | 100* |
| Triazamate | 50 | 5 | 75 | 94 | 100 | 94 |
| Cpd 1 + Triazamate | 20 + 50 | 100* | 100 + 50 | 73* | 500 + 50 | 100* |
| Cpd 1 + Triazamate | 20 + 75 | 100* | 100 + 75 | 63 | 500 + 75 | 12 |
| Cpd 1 + Triazamate | 20 + 100 | 7 | 100 + 100 | 94 | 500 + 100 | 6 |
| Thiodicarb | 0.08 | 2 | 0.16 | 6 | 0.4 | 7 |
| Cpd 1 + Thiodicarb | 20 + 0.08 | 3 | 100 + 0.08 | 40* | 500 + 0.08 | 13 |
| Cpd 1 + Thiodicarb | 20 + 0.16 | 5 | 100 + 0.16 | 2 | 500 + 0.16 | 11 |
| Cpd 1 + Thiodicarb | 20 + 0.4 | 2 | 100 + 0.4 | 4 | 500 + 0.4 | 5 |
| Tebufenozide | 100 | 12 | 1000 | 16 | 3000 | 12 |
| Cpd 1 + Tebufenozide | 20 + 100 | 6 | 100 + 100 | 15 | 500 + 100 | 9 |
| Cpd 1 + Tebufenozide | 20 + 1000 | 8 | 100 + 1000 | 80* | 500 + 1000 | 38 |
| Cpd 1 + Tebufenozide | 20 + 3000 | 7 | 100 + 3000 | 7 | 500 + 3000 | 44* |
| Deltamethrin | 0.1 | 11 | 0.2 | 14 | 0.3 | 7 |
| Cpd 1 + Deltamethrin | 20 + 0.1 | 11 | 100 + 0.1 | 8 | 500 + 0.1 | 13 |
| Cpd 1 + Deltamethrin | 20 + 0.2 | 12 | 100 + 0.2 | 14 | 500 + 0.2 | 100* |
| Cpd 1 + Deltamethrin | 20 + 0.3 | 6 | 100 + 0.3 | 100* | 500 + 0.3 | 100* |
| Oxamyl | 0.08 | 2 | 0.16 | 5 | 0.2 | 6 |
| Cpd 1 + Oxamyl | 20 + 0.08 | 2 | 100 + 0.08 | 7 | 500 + 0.08 | 8 |
| Cpd 1 + Oxamyl | 20 + 0.16 | 8 | 100 + 0.16 | 2 | 500 + 0.16 | 3 |
| Cpd 1 + Oxamyl | 20 + 0.2 | 7 | 100 + 0.2 | 6 | 500 + 0.2 | 7 |
| Hexaflumuron | 100 | 6 | 1000 | 5 | 3000 | 4 |
| Cpd 1 + Hexaflumuron | 20 + 100 | 2 | 100 + 100 | 2 | 500 + 100 | 11 |
| Cpd 1 + Hexaflumuron | 20 + 1000 | 11 | 100 + 1000 | 13 | 500 + 1000 | 14 |
| Cpd 1 + Hexaflumuron | 20 + 3000 | 8 | 100 + 3000 | 11 | 500 + 3000 | 7 |
| Acetamiprid | 0.3 | 43 | 0.4 | 85 | 0.5 | 100 |
| Cpd 1 + Acetamiprid | 20 + 0.3 | 3 | 100 + 0.3 | 6 | 500 + 0.3 | 7 |
| Cpd 1 + Acetamiprid | 20 + 0.4 | 14 | 100 + 0.4 | 86 | 500 + 0.4 | 100* |
| Cpd 1 + Acetamiprid | 20 + 0.5 | 41 | 100 + 0.5 | 100 | 500 + 0.5 | 100* |
| Cartap | 0.3 | 100 | 3 | 100 | 30 | 100 |
| Cpd 1 + Cartap | 20 + 0.3 | 100 | 100 + 0.3 | 100 | 500 + 0.3 | 100 |
| Cpd 1 + Cartap | 20 + 3 | 100 | 100 + 3 | 100 | 500 + 3 | 100 |
| Cpd 1 + Cartap | 20 + 30 | 100 | 100 + 30 | 100 | 500 + 30 | 100 |

TABLE 5B-continued

| Corn Plant Hopper | rate (ppm) | % mortality (obs) | rate (ppm) | % mortality (obs) | rate (ppm) | % mortality (obs) |
|---|---|---|---|---|---|---|
| Esfenvalerate | 0.1 | 7 | 0.3 | 6 | 0.9 | 6 |
| Cpd 1 + Esfenvalerate | 20 + 0.1 | 9 | 100 + 0.1 | 3 | 500 + 0.1 | 6 |
| Cpd 1 + Esfenvalerate | 20 + 0.3 | 4 | 100 + 0.3 | 4 | 500 + 0.3 | 2 |
| Cpd 1 + Esfenvalerate | 20 + 0.9 | 5 | 100 + 0.9 | 7 | 500 + 0.9 | 10 |
| Thiacloprid | 0.3 | 6 | 3 | 100 | 30 | 100 |
| Cpd 1 + Thiacloprid | 20 + 0.3 | 81* | 100 + 0.3 | 100* | 500 + 0.3 | 100* |
| Cpd 1 + Thiacloprid | 20 + 3 | 100 | 100 + 3 | 100 | 500 + 3 | 100 |
| Cpd 1 + Thiacloprid | 20 + 30 | 100 | 100 + 30 | 100 | 500 + 30 | 100 |
| Lambda-cyhalothrin | 0.016 | 7 | 0.08 | 7 | 0.4 | 28 |
| Cpd 1 + Lambda-cyhalothrin | 20 + 0.016 | 9 | 100 + 0.016 | 12 | 500 + 0.016 | 51 |
| Cpd 1 + Lambda-cyhalothrin | 20 + 0.08 | 9 | 100 + 0.08 | 7 | 500 + 0.08 | 11 |
| Cpd 1 + Lambda-cyhalothrin | 20 + 0.4 | 34 | 100 + 0.4 | 57 | 500 + 0.4 | 16 |
| Hydramethylnon | 0.01 | 7 | 1 | 1 | 2 | 6 |
| Cpd 1 + Hydramethylnon | 20 + 0.01 | 19 | 100 + 0.01 | 7 | 500 + 0.01 | 5 |
| Cpd 1 + Hydramethylnon | 20 + 1 | 6 | 100 + 1 | 8 | 500 + 1 | 7 |
| Cpd 1 + Hydramethylnon | 20 + 2 | 14 | 100 + 2 | 13 | 500 + 2 | 11 |
| Clothianidin | 10 | 100 | 100 | 100 | 1000 | 100 |
| Cpd 1 + Clothianidin | 20 + 10 | 100 | 100 + 10 | 100 | 500 + 10 | 100 |
| Cpd 1 + Clothianidin | 20 + 100 | 100 | 100 + 100 | 100 | 500 + 100 | 100 |
| Cpd 1 + Clothianidin | 20 + 1000 | 100 | 100 + 1000 | 100 | 500 + 1000 | 100 |
| Lufenuron | 0.08 | 9 | 0.4 | 7 | 2 | 7 |
| Cpd 1 + Lufenuron | 20 + 0.08 | 5 | 100 + 0.08 | 7 | 500 + 0.08 | 2 |
| Cpd 1 + Lufenuron | 20 + 0.4 | 9 | 100 + 0.4 | 5 | 500 + 0.4 | 2 |
| Cpd 1 + Lufenuron | 20 + 2 | 20 | 100 + 2 | 6 | 500 + 2 | 11 |
| Abamectin | 1.6 | 7 | 8 | 93 | 40 | 100 |
| Cpd 1 + Abamectin | 20 + 1.6 | 17 | 100 + 1.6 | 10 | 500 + 1.6 | 6 |
| Cpd 1 + Abamectin | 20 + 8 | 19 | 100 + 8 | 100* | 500 + 8 | 56 |
| Cpd 1 + Abamectin | 20 + 40 | 100 | 100 + 40 | 100 | 500 + 40 | 100 |
| Methoxyfenozide | 10 | 7 | 100 | 2 | 1000 | 10 |
| Cpd 1 + Methoxyfenozide | 20 + 10 | 3 | 100 + 10 | 10 | 500 + 10 | 7 |
| Cpd 1 + Methoxyfenozide | 20 + 100 | 2 | 100 + 100 | 5 | 500 + 100 | 13 |
| Cpd 1 + Methoxyfenozide | 20 + 1000 | 10 | 100 + 1000 | 4 | 500 + 1000 | 11 |
| Nitenpyram | 0.1 | 27 | 0.2 | 100 | 0.3 | 100 |
| Cpd 1 + Nitenpyram | 20 + 0.1 | 16 | 100 + 0.1 | 100* | 500 + 0.1 | 15 |
| Cpd 1 + Nitenpyram | 20 + 0.2 | 100 | 100 + 0.2 | 100 | 500 + 0.2 | 100 |
| Cpd 1 + Nitenpyram | 20 + 0.3 | 100 | 100 + 0.3 | 100 | 500 + 0.3 | 100 |
| Pyridalyl | 10 | 2 | 100 | 6 | 1000 | 11 |
| Cpd 1 + Pyridalyl | 20 + 10 | 7 | 100 + 10 | 13 | 500 + 10 | 66* |
| Cpd 1 + Pyridalyl | 20 + 100 | 4 | 100 + 100 | 10 | 500 + 100 | 48* |
| Cpd 1 + Pyridalyl | 20 + 1000 | 9 | 100 + 1000 | 61* | 500 + 1000 | 38 |
| Dinotefuran | 0.02 | 5 | 0.08 | 5 | 0.4 | 86 |
| Cpd 1 + Dinotefuran | 20 + 0.02 | 6 | 100 + 0.02 | 4 | 500 + 0.02 | 100* |
| Cpd 1 + Dinotefuran | 20 + 0.08 | 8 | 100 + 0.08 | 68 | 500 + 0.08 | 100* |
| Cpd 1 + Dinotefuran | 20 + 0.4 | 89 | 100 + 0.4 | 100* | 500 + 0.4 | 100* |
| Novaluron | 250 | 7 | 500 | 5 | 1000 | 100 |
| Cpd 1 + Novaluron | 20 + 250 | 7 | 100 + 250 | 6 | 500 + 250 | 6 |
| Cpd 1 + Novaluron | 20 + 500 | 7 | 100 + 500 | 2 | 500 + 500 | 6 |
| Cpd 1 + Novaluron | 20 + 1000 | 4 | 100 + 1000 | 9 | 500 + 1000 | 16 |

*indicates the observed % mortality is higher than the calculated % mortality by Colby equation.

Test E

For evaluating control of cotton melon aphid (*Aphis gossypii* Glover) through contact and/or systemic means, each test unit consisted of a small open container with a 6- to 7-day-old cotton plant inside. This was pre-infested by placing on a leaf of the test plant 30 to 40 aphids on a piece of leaf excised from a culture plant (cut-leaf method). The larvae moved onto the test plant as the leaf piece desiccated. After pre-infestation, the soil of the test unit was covered with a layer of sand.

Test compounds were formulated and sprayed as described for Test A. The applications were replicated three times. After spraying of the formulated test compounds, each test unit was allowed to dry for 1 hour and then a black, screened cap was placed on top. The test units were held for 6 days in a growth chamber at 19-21° C. and 50-70% relative humidity. Each test unit was then visually assessed for insect mortality; the results are listed in Tables 6A and 6B.

TABLE 6A

Cotton/Melon Aphid

| Compound 1 (ppm) | Imidacloprid (ppm) | Ratio | % Mortality (observed) | % Mortality (calculated) |
|---|---|---|---|---|
| 0.8 | 0 | — | 12 | — |
| 4.5 | 0 | — | 32 | — |
| 25 | 0 | — | 23 | — |
| 0 | 0.05 | — | 12 | — |
| 0 | 0.3 | — | 10 | — |
| 0 | 2.1 | — | 40 | — |
| 0.8 | 0.05 | 16:1 | 14 | 23 |
| 0.8 | 0.3 | 2.7:1 | 26 | 21 |
| 0.8 | 2.1 | 1:2.6 | 97 | 47 |
| 4.5 | 0.05 | 90:1 | 38 | 40 |
| 4.5 | 0.3 | 15:1 | 67 | 39 |
| 4.5 | 2.1 | 2.1:1 | 100 | 59 |
| 25 | 0.05 | 500:1 | 81 | 32 |
| 25 | 0.3 | 83:1 | 82 | 31 |
| 25 | 2.1 | 11.9:1 | 97 | 54 |

TABLE 6B

| Cotton/Melon Aphid | rate (ppm) | % mortality (obs) | rate (ppm) | % mortality (obs) | rate (ppm) | % mortality (obs) |
|---|---|---|---|---|---|---|
| Compound 1 | 4 | 25 | 20 | 41 | 100 | 49 |
| Methomyl | 2 | 11 | 5 | 35 | 15 | 64 |
| Cpd 1 + Methomyl | 4 + 2 | 13 | 20 + 2 | 51 | 100 + 2 | 29 |
| Cpd 1 + Methomyl | 4 + 5 | 23 | 20 + 5 | 47 | 100 + 5 | 68 |
| Cpd 1 + Methomyl | 4 + 15 | 75 | 20 + 15 | 81 | 100 + 15 | 98* |
| Amitraz | 10 | 20 | 100 | 35 | 1000 | 29 |
| Cpd 1 + Amitraz | 4 + 10 | 54* | 20 + 10 | 54 | 100 + 10 | 73* |
| Cpd 1 + Amitraz | 4 + 100 | 48 | 20 + 100 | 85* | 100 + 100 | 90* |
| Cpd 1 + Amitraz | 4 + 1000 | 50 | 20 + 1000 | 77* | 100 + 1000 | 89* |
| Thiamethoxam | 0.2 | 24 | 0.4 | 48 | 0.6 | 66 |
| Cpd 1 + Thiamethoxam | 4 + 0.2 | 46 | 20 + 0.2 | 33 | 100 + 0.2 | 100* |
| Cpd 1 + Thiamethoxam | 4 + 0.4 | 61 | 20 + 0.4 | 65* | 100 + 0.4 | 100* |
| Cpd 1 + Thiamethoxam | 4 + 0.6 | 98* | 20 + 0.6 | 92* | 100 + 0.6 | 100* |
| Pyridaben | 1 | 11 | 2 | 15 | 10 | 71 |
| Cpd 1 + Pyridaben | 4 + 1 | 33 | 20 + 1 | 41 | 100 + 1 | 95* |
| Cpd 1 + Pyridaben | 4 + 2 | 21 | 20 + 2 | 53 | 100 + 2 | 89* |
| Cpd 1 + Pyridaben | 4 + 10 | 47 | 20 + 10 | 73 | 100 + 10 | 100* |
| Flonicamid | 0.2 | 9 | 1 | 46 | 5 | 92 |
| Cpd 1 + Flonicamid | 4 + 0.2 | 96* | 20 + 0.2 | 69* | 100 + 0.2 | 64* |
| Cpd 1 + Flonicamid | 4 + 1 | 71* | 20 + 1 | 72* | 100 + 1 | 94* |
| Cpd 1 + Flonicamid | 4 + 5 | 100* | 20 + 5 | 86 | 100 + 5 | 100* |
| Dieldrin | 1 | 13 | 5 | 26 | 50 | 66 |
| Cpd 1 + Dieldrin | 4 + 1 | 49* | 20 + 1 | 83* | 100 + 1 | 70* |
| Cpd 1 + Dieldrin | 4 + 5 | 58* | 20 + 5 | 92* | 100 + 5 | 74* |
| Cpd 1 + Dieldrin | 4 + 50 | 98* | 20 + 50 | 100* | 100 + 50 | 100* |
| Spinosad | 10 | 16 | 100 | 35 | 1000 | 30 |
| Cpd 1 + Spinosad | 4 + 10 | 51* | 20 + 10 | 39 | 100 + 10 | 46 |
| Cpd 1 + Spinosad | 4 + 100 | 40 | 20 + 100 | 62 | 100 + 100 | 54 |
| Cpd 1 + Spinosad | 4 + 1000 | 77* | 20 + 1000 | 54 | 100 + 1000 | 65 |
| Fipronil | 2 | 27 | 4 | 44 | 8 | 85 |
| Cpd 1 + Fipronil | 4 + 2 | 27 | 20 + 2 | 64* | 100 + 2 | 81* |
| Cpd 1 + Fipronil | 4 + 4 | 44 | 20 + 4 | 89* | 100 + 4 | 83* |
| Cpd 1 + Fipronil | 4 + 8 | 85* | 20 + 8 | 81 | 100 + 8 | 98* |
| Pyriproxyfen | 10 | 14 | 100 | 28 | 1000 | 33 |
| Cpd 1 + Pyriproxyfen | 4 + 10 | 38 | 20 + 10 | 25 | 100 + 10 | 69* |
| Cpd 1 + Pyriproxyfen | 4 + 100 | 22 | 20 + 100 | 53 | 100 + 100 | 56 |
| Cpd 1 + Pyriproxyfen | 4 + 1000 | 25 | 20 + 1000 | 59 | 100 + 1000 | 95* |
| Pymetrozine | 0.1 | 22 | 0.5 | 38 | 2 | 62 |
| Cpd 1 + Pymetrozine | 4 + 0.1 | 29 | 20 + 0.1 | 82* | 100 + 0.1 | 57 |
| Cpd 1 + Pymetrozine | 4 + 0.5 | 35 | 20 + 0.5 | 38 | 100 + 0.5 | 93* |
| Cpd 1 + Pymetrozine | 4 + 2 | 73 | 20 + 2 | 88* | 100 + 2 | 100* |
| Buprofezin | 10 | 34 | 100 | 30 | 1000 | 36 |
| Cpd 1 + Buprofezin | 4 + 10 | 34 | 20 + 10 | 24 | 100 + 10 | 56 |
| Cpd 1 + Buprofezin | 4 + 100 | 41 | 20 + 100 | 31 | 100 + 100 | 76* |
| Cpd 1 + Buprofezin | 4 + 1000 | 31 | 20 + 1000 | 32 | 100 + 1000 | 78* |
| Chlorfenapyr | 1 | 27 | 10 | 57 | 150 | 67 |
| Cpd 1 + Chlorfenapyr | 4 + 1 | 29 | 20 + 1 | 52 | 100 + 1 | 38 |
| Cpd 1 + Chlorfenapyr | 4 + 10 | 43 | 20 + 10 | 51 | 100 + 10 | 75 |
| Cpd 1 + Chlorfenapyr | 4 + 150 | 100* | 20 + 150 | 96* | 100 + 150 | 100* |
| Chlorpyrifos | 1 | 26 | 5 | 14 | 50 | 13 |
| Cpd 1 + Chlorpyrifos | 4 + 1 | 19 | 20 + 1 | 46 | 100 + 1 | 74* |
| Cpd 1 + Chlorpyrifos | 4 + 5 | 34 | 20 + 5 | 49 | 100 + 5 | 65* |
| Cpd 1 + Chlorpyrifos | 4 + 50 | 25 | 20 + 50 | 32 | 100 + 50 | 64* |
| Cyromazine | 10 | 23 | 100 | 34 | 1000 | 28 |
| Cpd 1 + Cyromazine | 4 + 10 | 25 | 20 + 10 | 60 | 100 + 10 | 49 |
| Cpd 1 + Cyromazine | 4 + 100 | 29 | 20 + 100 | 34 | 100 + 100 | 79 |
| Cpd 1 + Cyromazine | 4 + 1000 | 23 | 20 + 1000 | 41 | 100 + 1000 | 60 |
| Fenoxycarb | 10 | 16 | 100 | 23 | 1000 | 34 |
| Cpd 1 + Fenoxycarb | 4 + 10 | 29 | 20 + 10 | 72* | 100 + 10 | 78* |
| Cpd 1 + Fenoxycarb | 4 + 100 | 25 | 20 + 100 | 50 | 100 + 100 | 87* |
| Cpd 1 + Fenoxycarb | 4 + 1000 | 60* | 20 + 1000 | 72* | 100 + 1000 | 75* |
| Methoprene | 10 | 43 | 100 | 53 | 1000 | 50 |
| Cpd 1 + Methoprene | 4 + 10 | 44 | 20 + 10 | 91* | 100 + 10 | 100* |
| Cpd 1 + Methoprene | 4 + 100 | 50 | 20 + 100 | 73 | 100 + 100 | 100* |
| Cpd 1 + Methoprene | 4 + 1000 | 45 | 20 + 1000 | 96* | 100 + 1000 | 100* |
| Indoxacarb | 10 | 16 | 20 | 28 | 30 | 34 |
| Cpd 1 + Indoxacarb | 4 + 10 | 32 | 20 + 10 | 51 | 100 + 10 | 48 |
| Cpd 1 + Indoxacarb | 4 + 20 | 35 | 20 + 20 | 47 | 100 + 20 | 67 |
| Cpd 1 + Indoxacarb | 4 + 30 | 35 | 20 + 30 | 47 | 100 + 30 | 75* |
| Triazamate | 2 | 17 | 20 | 59 | 100 | 100 |
| Cpd 1 + Triazamate | 4 + 2 | 20 | 20 + 2 | 18 | 100 + 2 | 33 |
| Cpd 1 + Triazamate | 4 + 20 | 53 | 20 + 20 | 43 | 100 + 20 | 58 |
| Cpd 1 + Triazamate | 4 + 100 | 96 | 20 + 100 | 100 | 100 + 100 | 100 |
| Thiodicarb | 3 | 49 | 10 | 32 | 30 | 69 |
| Cpd 1 + Thiodicarb | 4 + 3 | 33 | 20 + 3 | 37 | 100 + 3 | 51 |
| Cpd 1 + Thiodicarb | 4 + 10 | 36 | 20 + 10 | 43 | 100 + 10 | 54 |
| Cpd 1 + Thiodicarb | 4 + 30 | 35 | 20 + 30 | 80 | 100 + 30 | 96* |

TABLE 6B-continued

| Cotton/Melon Aphid | rate (ppm) | % mortality (obs) | rate (ppm) | % mortality (obs) | rate (ppm) | % mortality (obs) |
|---|---|---|---|---|---|---|
| Tebufenozide | 0.5 | 21 | 1.5 | 37 | 3 | 22 |
| Cpd 1 + Tebufenozide | 4 + 0.5 | 36 | 20 + 0.5 | 49 | 100 + 0.5 | 61 |
| Cpd 1 + Tebufenozide | 4 + 1.5 | 39 | 20 + 1.5 | 57 | 100 + 1.5 | 85* |
| Cpd 1 + Tebufenozide | 4 + 3 | 42 | 20 + 3 | 45 | 100 + 3 | 83* |
| Deltamethrin | 0.1 | 52 | 0.2 | 39 | 0.3 | 88 |
| Cpd 1 + Deltamethrin | 4 + 0.1 | 28 | 20 + 0.1 | 29 | 100 + 0.1 | 58 |
| Cpd 1 + Deltamethrin | 4 + 0.2 | 28 | 20 + 0.2 | 31 | 100 + 0.2 | 46 |
| Cpd 1 + Deltamethrin | 4 + 0.3 | 47 | 20 + 0.3 | 52 | 100 + 0.3 | 45 |
| Oxamyl | 1 | 29 | 10 | 37 | 1000 | 100 |
| Cpd 1 + Oxamyl | 4 + 1 | 35 | 20 + 1 | 61* | 100 + 1 | 75* |
| Cpd 1 + Oxamyl | 4 + 10 | 47 | 20 + 10 | 71* | 100 + 10 | 77* |
| Cpd 1 + Oxamyl | 4 + 1000 | 100 | 20 + 1000 | 100 | 100 + 1000 | 100 |
| Hexaflumuron | 30 | 32 | 1000 | 30 | 3000 | 29 |
| Cpd 1 + Hexaflumuron | 4 + 30 | 40 | 20 + 30 | 60 | 100 + 30 | 47 |
| Cpd 1 + Hexaflumuron | 4 + 1000 | 74* | 20 + 1000 | 65* | 100 + 1000 | 70* |
| Cpd 1 + Hexaflumuron | 4 + 3000 | 42 | 20 + 3000 | 60* | 100 + 3000 | 69* |
| Acetamiprid | 0.02 | 42 | 0.08 | 67 | 0.4 | 100 |
| Cpd 1 + Acetamiprid | 4 + 0.02 | 41 | 20 + 0.02 | 49 | 100 + 0.02 | 62 |
| Cpd 1 + Acetamiprid | 4 + 0.08 | 55 | 20 + 0.08 | 85* | 100 + 0.08 | 86* |
| Cpd 1 + Acetamiprid | 4 + 0.4 | 94 | 20 + 0.4 | 85 | 100 + 0.4 | 100 |
| Cartap | 0.2 | 29 | 2 | 34 | 200 | 83 |
| Cpd 1 + Cartap | 4 + 0.2 | 79* | 20 + 0.2 | 86* | 100 + 0.2 | 83* |
| Cpd 1 + Cartap | 4 + 2 | 64* | 20 + 2 | 56 | 100 + 2 | 55 |
| Cpd 1 + Cartap | 4 + 200 | 91* | 20 + 200 | 86 | 100 + 200 | 100* |
| Esfenvalerate | 0.1 | 95 | 0.3 | 94 | 1 | 100 |
| Cpd 1 + Esfenvalerate | 4 + 0.1 | 75 | 20 + 0.1 | 88 | 100 + 0.1 | 96 |
| Cpd 1 + Esfenvalerate | 4 + 0.3 | 82 | 20 + 0.3 | 81 | 100 + 0.3 | 87 |
| Cpd 1 + Esfenvalerate | 4 + 1 | 75 | 20 + 1 | 91 | 100 + 1 | 100 |
| Thiacloprid | 0.3 | 50 | 1.5 | 100 | 6 | 100 |
| Cpd 1 + Thiacloprid | 4 + 0.3 | 64 | 20 + 0.3 | 84* | 100 + 0.3 | 94* |
| Cpd 1 + Thiacloprid | 4 + 1.5 | 96 | 20 + 1.5 | 100 | 100 + 1.5 | 96 |
| Cpd 1 + Thiacloprid | 4 + 6 | 100 | 20 + 6 | 100 | 100 + 6 | 100 |
| Lambda-cyhalothrin | 0.08 | 22 | 0.4 | 81 | 2 | 100 |
| Cpd 1 + Lambda-cyhalothrin | 4 + 0.08 | 39 | 20 + 0.08 | 66* | 100 + 0.08 | 63 |
| Cpd 1 + Lambda-cyhalothrin | 4 + 0.4 | 100* | 20 + 0.4 | 84 | 100 + 0.4 | 100* |
| Cpd 1 + Lambda-cyhalothrin | 4 + 2 | 100 | 20 + 2 | 100 | 100 + 2 | 100 |
| Hydramethylnon | 500 | 21 | 1000 | 40 | 1500 | 39 |
| Cpd 1 + Hydramethylnon | 4 + 500 | 39 | 20 + 500 | 75* | 100 + 500 | 67* |
| Cpd 1 + Hydramethylnon | 4 + 1000 | 53 | 20 + 1000 | 66 | 100 + 1000 | 69 |
| Cpd 1 + Hydramethylnon | 4 + 1500 | 54 | 20 + 1500 | 66 | 100 + 1500 | 77* |
| Clothianidin | 0.08 | 75 | 0.4 | 91 | 2 | 99 |
| Cpd 1 + Clothianidin | 4 + 0.08 | 94* | 20 + 0.08 | 84 | 100 + 0.08 | 92 |
| Cpd 1 + Clothianidin | 4 + 0.4 | 92 | 20 + 0.4 | 88 | 100 + 0.4 | 100 |
| Cpd 1 + Clothianidin | 4 + 2 | 100 | 20 + 2 | 100 | 100 + 2 | 100 |
| Lufenuron | 0.08 | 28 | 0.4 | 39 | 2 | 58 |
| Cpd 1 + Lufenuron | 4 + 0.08 | 37 | 20 + 0.08 | 55 | 100 + 0.08 | 51 |
| Cpd 1 + Lufenuron | 4 + 0.4 | 34 | 20 + 0.4 | 66 | 100 + 0.4 | 53 |
| Cpd 1 + Lufenuron | 4 + 2 | 40 | 20 + 2 | 65 | 100 + 2 | 54 |
| Abamectin | 0.08 | 35 | 0.4 | 58 | 2 | 100 |
| Cpd 1 + Abamectin | 4 + 0.08 | 43 | 20 + 0.08 | 59 | 100 + 0.08 | 82* |
| Cpd 1 + Abamectin | 4 + 0.4 | 100* | 20 + 0.4 | 100* | 100 + 0.4 | 93* |
| Cpd 1 + Abamectin | 4 + 2 | 100 | 20 + 2 | 100 | 100 + 2 | 94 |
| Methoxyfenozide | 5 | 32 | 50 | 54 | 500 | 38 |
| Cpd 1 + Methoxyfenozide | 4 + 5 | 32 | 20 + 5 | 62* | 100 + 5 | 57 |
| Cpd 1 + Methoxyfenozide | 4 + 50 | 54* | 20 + 50 | 46 | 100 + 50 | 62 |
| Cpd 1 + Methoxyfenozide | 4 + 500 | 38 | 20 + 500 | 50 | 100 + 500 | 54 |
| Nitenpyram | 0.2 | 29 | 0.4 | 49 | 0.6 | 71 |
| Cpd 1 + Nitenpyram | 4 + 0.2 | 27 | 20 + 0.2 | 71* | 100 + 0.2 | 26 |
| Cpd 1 + Nitenpyram | 4 + 0.4 | 55 | 20 + 0.4 | 94* | 100 + 0.4 | 72 |
| Cpd 1 + Nitenpyram | 4 + 0.6 | 62 | 20 + 0.6 | 100* | 100 + 0.6 | 95* |
| Pyridalyl | 1 | 22 | 1.5 | 34 | 2 | 32 |
| Cpd 1 + Pyridalyl | 4 + 1 | 30 | 20 + 1 | 43 | 100 + 1 | 51 |
| Cpd 1 + Pyridalyl | 4 + 1.5 | 42 | 20 + 1.5 | 55 | 100 + 1.5 | 66 |
| Cpd 1 + Pyridalyl | 4 + 2 | 33 | 20 + 2 | 59 | 100 + 2 | 64 |
| Dinotefuran | 1 | 31 | 2 | 64 | 5 | 92 |
| Cpd 1 + Dinotefuran | 4 + 1 | 20 | 20 + 1 | 62 | 100 + 1 | 76* |
| Cpd 1 + Dinotefuran | 4 + 2 | 45 | 20 + 2 | 82 | 100 + 2 | 89 |
| Cpd 1 + Dinotefuran | 4 + 5 | 100 | 20 + 5 | 96 | 100 + 5 | 96 |
| Novaluron | 50 | 28 | 250 | 30 | 1000 | 29 |
| Cpd 1 + Novaluron | 4 + 50 | 34 | 20 + 50 | 70* | 100 + 50 | 78* |
| Cpd 1 + Novaluron | 4 + 250 | 52* | 20 + 250 | 89* | 100 + 250 | 84* |
| Cpd 1 + Novaluron | 4 + 1000 | 48* | 20 + 1000 | 89* | 100 + 1000 | 86* |

*indicates the observed % mortality is higher than the calculated % mortality by Colby equation.

Test F

For evaluating control of green peach aphid (*Myzus persicae* Sulzer) through contact and/or systemic means, each test unit consisted of a small open container with a 12- to 15-day-old radish plant inside. This was pre-infested by placing on a leaf of the test plant 30 to 40 aphids on a piece of leaf excised from a culture plant (cut-leaf method). The larvae moved onto the test plant as the leaf piece desiccated. After pre-infestation, the soil of the test unit was covered with a layer of sand.

Test compounds were formulated and sprayed as described in Test A, replicated three times. After spraying of the formulated test compound, each test unit was allowed to dry for 1 hour and then a black, screened cap was placed on top. The test units were held for 6 days in a growth chamber at 19-21° C. and 50-70% relative humidity. Each test unit was then visually assessed for insect mortality; the results are listed in Tables 7A and 7B.

TABLE 7A

Green Peach Aphid

| Compound 1 (ppm) | Imidacloprid (ppm) | Ratio | % Mortality (observed) | % Mortality (calculated) |
|---|---|---|---|---|
| 2.1 | 0 | — | 5 | — |
| 3.9 | 0 | — | 2 | — |
| 7.5 | 0 | — | 6 | — |
| 0 | 0.08 | — | 4 | — |
| 0 | 0.15 | — | 12 | — |
| 0 | 0.26 | — | 50 | — |
| 2.1 | 0.08 | 26:1 | 49 | 9 |
| 2.1 | 0.15 | 14:1 | 32 | 16 |
| 2.1 | 0.26 | 8.1:1 | 92 | 53 |
| 3.9 | 0.08 | 49:1 | 46 | 6 |
| 3.9 | 0.15 | 26:1 | 59 | 14 |
| 3.9 | 0.26 | 15:1 | 84 | 51 |
| 7.5 | 0.08 | 94:1 | 51 | 10 |
| 7.5 | 0.15 | 50:1 | 52 | 17 |
| 7.5 | 0.26 | 29:1 | 64 | 53 |

TABLE 7B

| Green Peach Aphid | rate (ppm) | % mortality (obs) | rate (ppm) | % mortality (obs) | rate (ppm) | % mortality (obs) |
|---|---|---|---|---|---|---|
| Compound 1 | 10 | 24 | 20 | 35 | 40 | 36 |
| Methomyl | 50 | 20 | 100 | 61 | 200 | 100 |
| Cpd 1 + Methomyl | 10 + 50 | 40 | 20 + 50 | 32 | 40 + 50 | 35 |
| Cpd 1 + Methomyl | 10 + 100 | 67 | 20 + 100 | 80* | 40 + 100 | 79* |
| Cpd 1 + Methomyl | 10 + 200 | 94 | 20 + 200 | 100 | 40 + 200 | 100 |
| Amitraz | 10 | 16 | 100 | 12 | 1000 | 34 |
| Cpd 1 + Amitraz | 10 + 10 | 29 | 20 + 10 | 21 | 40 + 10 | 56* |
| Cpd 1 + Amitraz | 10 + 100 | 13 | 20 + 100 | 11 | 40 + 100 | 28 |
| Cpd 1 + Amitraz | 10 + 1000 | 72* | 20 + 1000 | 63* | 40 + 1000 | 69* |
| Thiamethoxam | 0.2 | 35 | 0.4 | 94 | 0.6 | 100 |
| Cpd 1 + Thiamethoxam | 10 + 0.2 | 24 | 20 + 0.2 | 17 | 40 + 0.2 | 35 |
| Cpd 1 + Thiamethoxam | 10 + 0.4 | 81 | 20 + 0.4 | 98* | 40 + 0.4 | 87 |
| Cpd 1 + Thiamethoxam | 10 + 0.6 | 100 | 20 + 0.6 | 92 | 40 + 0.6 | 100 |
| Pyridaben | 1 | 100 | 10 | 14 | 60 | 60 |
| Cpd 1 + Pyridaben | 10 + 1 | 11 | 20 + 1 | 8 | 40 + 1 | 6 |
| Cpd 1 + Pyridaben | 10 + 10 | 29 | 20 + 10 | 18 | 40 + 10 | 19 |
| Cpd 1 + Pyridaben | 10 + 60 | 42 | 20 + 60 | 70 | 40 + 60 | 49 |
| Flonicamid | 0.1 | 16 | 0.2 | 10 | 2 | 33 |
| Cpd 1 + Flonicamid | 10 + 0.1 | 36 | 20 + 0.1 | 22 | 40 + 0.1 | 43 |
| Cpd 1 + Flonicamid | 10 + 0.2 | 34 | 20 + 0.2 | 50* | 40 + 0.2 | 32 |
| Cpd 1 + Flonicamid | 10 + 2 | 66* | 20 + 2 | 81* | 40 + 2 | 79* |
| Dieldrin | 10 | 59 | 100 | 43 | 1000 | 41 |
| Cpd 1 + Dieldrin | 10 + 10 | 41 | 20 + 10 | 43 | 40 + 10 | 28 |
| Cpd 1 + Dieldrin | 10 + 100 | 51 | 20 + 100 | 75* | 40 + 100 | 37 |
| Cpd 1 + Dieldrin | 10 + 1000 | 82* | 20 + 1000 | 77* | 40 + 1000 | 86* |
| Spinosad | 10 | 25 | 100 | 46 | 1000 | 59 |
| Cpd 1 + Spinosad | 10 + 10 | 37 | 20 + 10 | 18 | 40 + 10 | 92* |
| Cpd 1 + Spinosad | 10 + 100 | 48 | 20 + 100 | 31 | 40 + 100 | 69* |
| Cpd 1 + Spinosad | 10 + 1000 | 72* | 20 + 1000 | 100* | 40 + 1000 | 16 |
| Fipronil | 2 | 17 | 4 | 31 | 8 | 50 |
| Cpd 1 + Fipronil | 10 + 2 | 22 | 20 + 2 | 34 | 40 + 2 | 57* |
| Cpd 1 + Fipronil | 10 + 4 | 44 | 20 + 4 | 31 | 40 + 4 | 46 |
| Cpd 1 + Fipronil | 10 + 8 | 28 | 20 + 8 | 60 | 40 + 8 | 99 |
| Pyriproxyfen | 10 | 23 | 100 | 12 | 1000 | 26 |
| Cpd 1 + Pyriproxyfen | 10 + 10 | 35 | 20 + 10 | 27 | 40 + 10 | 40 |
| Cpd 1 + Pyriproxyfen | 10 + 100 | 46* | 20 + 100 | 24 | 40 + 100 | 50* |
| Cpd 1 + Pyriproxyfen | 10 + 1000 | 28 | 20 + 1000 | 49 | 40 + 1000 | 64* |
| Pymetrozine | 0.1 | 13 | 0.5 | 41 | 2 | 79 |
| Cpd 1 + Pymetrozine | 10 + 0.1 | 17 | 20 + 0.1 | 57* | 40 + 0.1 | 64* |
| Cpd 1 + Pymetrozine | 10 + 0.5 | 38 | 20 + 0.5 | 79* | 40 + 0.5 | 89* |
| Cpd 1 + Pymetrozine | 10 + 2 | 94* | 20 + 2 | 100* | 40 + 2 | 85 |
| Buprofezin | 10 | 63 | 100 | 63 | 1000 | 54 |
| Cpd 1 + Buprofezin | 10 + 10 | 28 | 20 + 10 | 41 | 40 + 10 | 35 |

TABLE 7B-continued

| Green Peach Aphid | rate (ppm) | % mortality (obs) | rate (ppm) | % mortality (obs) | rate (ppm) | % mortality (obs) |
|---|---|---|---|---|---|---|
| Cpd 1 + Buprofezin | 10 + 100 | 51 | 20 + 100 | 53 | 40 + 100 | 61 |
| Cpd 1 + Buprofezin | 10 + 1000 | 41 | 20 + 1000 | 50 | 40 + 1000 | 56 |
| Chlorfenapyr | 1.5 | 22 | 7 | 36 | 35 | 100 |
| Cpd 1 + Chlorfenapyr | 10 + 1.5 | 39 | 20 + 1.5 | 29 | 40 + 1.5 | 42 |
| Cpd 1 + Chlorfenapyr | 10 + 7 | 59* | 20 + 7 | 54 | 40 + 7 | 54 |
| Cpd 1 + Chlorfenapyr | 10 + 35 | 100 | 20 + 35 | 100 | 40 + 35 | 100 |
| Chlorpyrifos | 10 | 5 | 100 | 18 | 1000 | 9 |
| Cpd 1 + Chlorpyrifos | 10 + 10 | 11 | 20 + 10 | 12 | 40 + 10 | 28 |
| Cpd 1 + Chlorpyrifos | 10 + 100 | 17 | 20 + 100 | 20 | 40 + 100 | 10 |
| Cpd 1 + Chlorpyrifos | 10 + 1000 | 14 | 20 + 1000 | 20 | 40 + 1000 | 27 |
| Cyromazine | 10 | 24 | 100 | 33 | 1000 | 65 |
| Cpd 1 + Cyromazine | 10 + 10 | 18 | 20 + 10 | 10 | 40 + 10 | 32 |
| Cpd 1 + Cyromazine | 10 + 100 | 18 | 20 + 100 | 6 | 40 + 100 | 19 |
| Cpd 1 + Cyromazine | 10 + 1000 | 46 | 20 + 1000 | 24 | 40 + 1000 | 65 |
| Fenoxycarb | 10 | 17 | 100 | 16 | 1000 | 18 |
| Cpd 1 + Fenoxycarb | 10 + 10 | 13 | 20 + 10 | 29 | 40 + 10 | 27 |
| Cpd 1 + Fenoxycarb | 10 + 100 | 31 | 20 + 100 | 23 | 40 + 100 | 64* |
| Cpd 1 + Fenoxycarb | 10 + 1000 | 19 | 20 + 1000 | 39 | 40 + 1000 | 54* |
| Methoprene | 10 | 27 | 100 | 23 | 1000 | 45 |
| Cpd 1 + Methoprene | 10 + 10 | 15 | 20 + 10 | 95* | 40 + 10 | 82* |
| Cpd 1 + Methoprene | 10 + 100 | 28 | 20 + 100 | 44 | 40 + 100 | 11 |
| Cpd 1 + Methoprene | 10 + 1000 | 15 | 20 + 1000 | 59 | 40 + 1000 | 62 |
| Indoxacarb | 10 | 9 | 20 | 7 | 30 | 8 |
| Cpd 1 + Indoxacarb | 10 + 10 | 10 | 20 + 10 | 13 | 40 + 10 | 15 |
| Cpd 1 + Indoxacarb | 10 + 20 | 12 | 20 + 20 | 20 | 40 + 20 | 22 |
| Cpd 1 + Indoxacarb | 10 + 30 | 8 | 20 + 30 | 23 | 40 + 30 | 26 |
| Triazamate | 0.1 | 1 | 1 | 2 | 100 | 100 |
| Cpd 1 + Triazamate | 10 + 0.1 | 4 | 20 + 0.1 | 5 | 40 + 0.1 | 11 |
| Cpd 1 + Triazamate | 10 + 1 | 7 | 20 + 1 | 5 | 40 + 1 | 10 |
| Cpd 1 + Triazamate | 10 + 100 | 100 | 20 + 100 | 100 | 40 + 100 | 100 |
| Thiodicarb | 20 | 10 | 150 | 17 | 900 | 98 |
| Cpd 1 + Thiodicarb | 10 + 20 | 7 | 20 + 20 | 18 | 40 + 20 | 21 |
| Cpd 1 + Thiodicarb | 10 + 150 | 19 | 20 + 150 | 47* | 40 + 150 | 29 |
| Cpd 1 + Thiodicarb | 10 + 900 | 100* | 20 + 900 | 88 | 40 + 900 | 100* |
| Tebufenozide | 100 | 8 | 1000 | 7 | 3000 | 9 |
| Cpd 1 + Tebufenozide | 10 + 100 | 23 | 20 + 100 | 9 | 40 + 100 | 13 |
| Cpd 1 + Tebufenozide | 10 + 1000 | 22 | 20 + 1000 | 20 | 40 + 1000 | 22 |
| Cpd 1 + Tebufenozide | 10 + 3000 | 12 | 20 + 3000 | 33 | 40 + 3000 | 15 |
| Deltamethrin | 250 | 9 | 300 | 3 | 1000 | 9 |
| Cpd 1 + Deltamethrin | 10 + 250 | 5 | 20 + 250 | 2 | 40 + 250 | 10 |
| Cpd 1 + Deltamethrin | 10 + 300 | 6 | 20 + 300 | 5 | 40 + 300 | 6 |
| Cpd 1 + Deltamethrin | 10 + 1000 | 11 | 20 + 1000 | 5 | 40 + 1000 | 13 |
| Oxamyl | 40 | 8 | 70 | 18 | 100 | 35 |
| Cpd 1 + Oxamyl | 10 + 40 | 29 | 20 + 40 | 31 | 40 + 40 | 28 |
| Cpd 1 + Oxamyl | 10 + 70 | 42* | 20 + 70 | 57* | 40 + 70 | 72* |
| Cpd 1 + Oxamyl | 10 + 100 | 63* | 20 + 100 | 85* | 40 + 100 | 70* |
| Hexaflumuron | 100 | 8 | 1000 | 6 | 3000 | 13 |
| Cpd 1 + Hexaflumuron | 10 + 100 | 19 | 20 + 100 | 21 | 40 + 100 | 46* |
| Cpd 1 + Hexaflumuron | 10 + 1000 | 41* | 20 + 1000 | 30 | 40 + 1000 | 19 |
| Cpd 1 + Hexaflumuron | 10 + 3000 | 20 | 20 + 3000 | 20 | 40 + 3000 | 39 |
| Acetamiprid | 0.2 | 27 | 0.4 | 52 | 0.6 | 46 |
| Cpd 1 + Acetamiprid | 10 + 0.2 | 26 | 20 + 0.2 | 31 | 40 + 0.2 | 38 |
| Cpd 1 + Acetamiprid | 10 + 0.4 | 59 | 20 + 0.4 | 75* | 40 + 0.4 | 66 |
| Cpd 1 + Acetamiprid | 10 + 0.6 | 73* | 20 + 0.6 | 98* | 40 + 0.6 | 98* |
| Cartap | 0.2 | 11 | 0.4 | 26 | 0.6 | 17 |
| Cpd 1 + Cartap | 10 + 0.2 | 28 | 20 + 0.2 | 13 | 40 + 0.2 | 20 |
| Cpd 1 + Cartap | 10 + 0.4 | 21 | 20 + 0.4 | 19 | 40 + 0.4 | 14 |
| Cpd 1 + Cartap | 10 + 0.6 | 13 | 20 + 0.6 | 11 | 40 + 0.6 | 26 |
| Esfenvalerate | 50 | 100 | 1000 | 41 | 3000 | 23 |
| Cpd 1 + Esfenvalerate | 10 + 50 | 10 | 20 + 50 | 26 | 40 + 50 | 21 |
| Cpd 1 + Esfenvalerate | 10 + 1000 | 47 | 20 + 1000 | 24 | 40 + 1000 | 32 |
| Cpd 1 + Esfenvalerate | 10 + 3000 | 30 | 20 + 3000 | 24 | 40 + 3000 | 23 |
| Thiacloprid | 0.2 | 13 | 0.3 | 68 | 0.4 | 42 |
| Cpd 1 + Thiacloprid | 10 + 0.2 | 30 | 20 + 0.2 | 42 | 40 + 0.2 | 64* |
| Cpd 1 + Thiacloprid | 10 + 0.3 | 13 | 20 + 0.3 | 41 | 40 + 0.3 | 70* |
| Cpd 1 + Thiacloprid | 10 + 0.4 | 36 | 20 + 0.4 | 69* | 40 + 0.4 | 72* |
| Lambda-cyhalothrin | 0.016 | 14 | 0.08 | 15 | 0.4 | 30 |
| Cpd 1 + Lambda-cyhalothrin | 10 + 0.016 | 30 | 20 + 0.016 | 16 | 40 + 0.016 | 15 |
| Cpd 1 + Lambda-cyhalothrin | 10 + 0.08 | 25 | 20 + 0.08 | 39 | 40 + 0.08 | 9 |
| Cpd 1 + Lambda-cyhalothrin | 10 + 0.4 | 36 | 20 + 0.4 | 36 | 40 + 0.4 | 16 |
| Hydramethylnon | 500 | 18 | 1000 | 8 | 1500 | 7 |
| Cpd 1 + Hydramethylnon | 10 + 500 | 23 | 20 + 500 | 21 | 40 + 500 | 18 |
| Cpd 1 + Hydramethylnon | 10 + 1000 | 25 | 20 + 1000 | 24 | 40 + 1000 | 59* |
| Cpd 1 + Hydramethylnon | 10 + 1500 | 18 | 20 + 1500 | 28 | 40 + 1500 | 27 |
| Clothianidin | 0.08 | 100 | 0.4 | 100 | 2 | 100 |
| Cpd 1 + Clothianidin | 10 + 0.08 | 100 | 20 + 0.08 | 100 | 40 + 0.08 | 100 |

TABLE 7B-continued

| Green Peach Aphid | rate (ppm) | % mortality (obs) | rate (ppm) | % mortality (obs) | rate (ppm) | % mortality (obs) |
|---|---|---|---|---|---|---|
| Cpd 1 + Clothianidin | 10 + 0.4 | 100 | 20 + 0.4 | 100 | 40 + 0.4 | 100 |
| Cpd 1 + Clothianidin | 10 + 2 | 100 | 20 + 2 | 100 | 40 + 2 | 100 |
| Lufenuron | 50 | 34 | 250 | 15 | 1000 | 28 |
| Cpd 1 + Lufenuron | 10 + 50 | 29 | 20 + 50 | 58* | 40 + 50 | 49 |
| Cpd 1 + Lufenuron | 10 + 250 | 35 | 20 + 250 | 48* | 40 + 250 | 75* |
| Cpd 1 + Lufenuron | 10 + 1000 | 49* | 20 + 1000 | 18 | 40 + 1000 | 51 |
| Abamectin | 0.08 | 47 | 0.4 | 100 | 2 | 100 |
| Cpd 1 + Abamectin | 10 + 0.08 | 59 | 20 + 0.08 | 100* | 40 + 0.08 | 42 |
| Cpd 1 + Abamectin | 10 + 0.4 | 100 | 20 + 0.4 | 97 | 40 + 0.4 | 100 |
| Cpd 1 + Abamectin | 10 + 2 | 100 | 20 + 2 | 100 | 40 + 2 | 100 |
| Methoxyfenozide | 10 | 7 | 100 | 17 | 1000 | 6 |
| Cpd 1 + Methoxyfenozide | 10 + 10 | 9 | 20 + 10 | 17 | 40 + 10 | 16 |
| Cpd 1 + Methoxyfenozide | 10 + 100 | 8 | 20 + 100 | 17 | 40 + 100 | 19 |
| Cpd 1 + Methoxyfenozide | 10 + 1000 | 21 | 20 + 1000 | 19 | 40 + 1000 | 29 |
| Nitenpyram | 0.2 | 7 | 0.4 | 17 | 0.6 | 40 |
| Cpd 1 + Nitenpyram | 10 + 0.2 | 25 | 20 + 0.2 | 16 | 40 + 0.2 | 10 |
| Cpd 1 + Nitenpyram | 10 + 0.4 | 24 | 20 + 0.4 | 60* | 40 + 0.4 | 7 |
| Cpd 1 + Nitenpyram | 10 + 0.6 | 75* | 20 + 0.6 | 52 | 40 + 0.6 | 58 |
| Pyridalyl | 1 | 18 | 10 | 8 | 20 | 3 |
| Cpd 1 + Pyridalyl | 10 + 1 | 7 | 20 + 1 | 19 | 40 + 1 | 18 |
| Cpd 1 + Pyridalyl | 10 + 10 | 11 | 20 + 10 | 17 | 40 + 10 | 15 |
| Cpd 1 + Pyridalyl | 10 + 20 | 24 | 20 + 20 | 27 | 40 + 20 | 27 |
| Dinotefuran | 1 | 24 | 2 | 32 | 5 | 61 |
| Cpd 1 + Dinotefuran | 10 + 1 | 9 | 20 + 1 | 12 | 40 + 1 | 61* |
| Cpd 1 + Dinotefuran | 10 + 2 | 30 | 20 + 2 | 27 | 40 + 2 | 48 |
| Cpd 1 + Dinotefuran | 10 + 5 | 82* | 20 + 5 | 87* | 40 + 5 | 89* |
| Novaluron | 250 | 14 | 500 | 24 | 1000 | 25 |
| Cpd 1 + Novaluron | 10 + 250 | 31 | 20 + 250 | 47 | 40 + 250 | 25 |
| Cpd 1 + Novaluron | 10 + 500 | 34 | 20 + 500 | 29 | 40 + 500 | 47 |
| Cpd 1 + Novaluron | 10 + 1000 | 28 | 20 + 1000 | 49 | 40 + 1000 | 74* |

*indicates the observed % mortality is higher than the calculated % mortality by Colby equation.

Test G

For evaluating systemic control of silverleaf whitefly (*Bemisia argentifolii*), each test unit consisted of a 10-inch (25.4 cm) pot with sand, and a tomato plant (var. Tiny Tim) at the 5 to 10 true leaf stage. Oxamyl was in the liquid formulation as Vydate® L and compound 1 was in a wettable powder formulation with 50% active ingredient. Test compounds in approximately 200 mL of water per pot were applied by drip irrigation in the greenhouse. Whitefly activity was evaluated on a naturally occurring population by removing 5 old leaves with clearly visible nymphs. When there were no leaves with clearly visible nymphs, 5 old leaves were removed at random. Leaves were evaluated for dead and live nymphs. For all tests, analysis was conducted by using Fisher's LSD test for means separation, at p=0.05 (see. K. A. Gomez and A. A. Gomez, "Statistical Procedures for Agricultural Research", $2^{nd}$ edition, John Wiley & Sons, New York, 680 pp). Mean comparisons were made within each evaluation date only. The results are listed in Table 8.

Test H

For evaluating systemic control of beet armyworm (*Spodoptera exigua*), each test unit consisted of a 10-inch (25.4 cm) pot filled with sand and containing a tomato plant (var. Tiny Tim) at the 5 to 10 true leaf stage. Oxamyl was in the liquid formulation as Vydate® L and compound 1 was in a wettable powder formulation with 50% active ingredient. Test compounds in approximately 200 mL of water per pot were applied by drip irrigation in the greenhouse. The plants were sampled at indicated date by cutting discs of the leaf material and placing each disc on a layer of agar gel in a 16-well, 1.5 oz. cup tray (B-150-S 0.028 Natural, Clear Pack Co., Franklin Park, Ill. 60131). One beet armyworm larva was added to each cell and the cells were covered. Trays were held in the growth chamber at 25° C., 16-hour light:8-hour dark, 60% relative humidity for 4 days. The percentage of mortality (abbreviated as % Morta.) and percentage of feeding (abbreviated as % feed), were visually assessed; the results are listed in Table 9. For all tests, analysis was conducted by using the LSD test. Mean comparisons were made within each evaluation date only.

TABLE 8

| | | Silverleaf Whitefly | | | | | |
|---|---|---|---|---|---|---|---|
| | | Day 6 | | Day 13 | | Day 20 | |
| Compound/mixture | mg ai/pot | Nymphs number | % Mortality | Nymphs number | % Mortality | Nymphs number | % Mortality |
| Oxamyl | 100 | 380 | 6 | 506 | 34 | 404 | 28 |
| Compound 1 | 20 | 316 | 44 | 194 | 99 | 300 | 100 |
| Oxamyl + Compound 1 | 100 + 20 | 228 | 20 | 431 | 70 | 162 | 83 |
| Untreated | 0 | 512 | 1 | 534 | 7 | 53 | 47 |

TABLE 9

Beet Armyworm

| Compound/mixture | mg ai/pot | Day 6 new & old | | Day 13 - old growth | | Day 13 - old growth | |
|---|---|---|---|---|---|---|---|
| | | % Morta. | % feed | % Morta. | % feed | % Morta. | % feed |
| Oxamyl | 100 | 26 | 49 | 35 | 43 | 40 | 40 |
| Compound 1 | 20 | 99 | 0 | 100 | 0 | 97 | 0 |
| Oxamyl + Compound 1 | 100 + 20 | 100 | 0 | 100 | 0 | 100 | 0 |
| Untreated | 0 | 1 | 77 | 0 | 92 | 0 | 61 |

| Compound/mixture | mg ai/pot | Day 20 - new growth | | Day 20 - old growth | |
|---|---|---|---|---|---|
| | | % Morta. | % feed | % Morta. | % feed |
| Oxamyl | 100 | 25 | 92 | 31 | 65 |
| Compound 1 | 20 | 100 | 0 | 100 | 0 |
| Oxamyl + Compound 1 | 100 + 20 | 100 | 0 | 96 | 1 |
| Untreated | 0 | 13 | 93 | 61 | 60 |

Test I

For evaluating control of beet armyworm (*Spodoptera exigua*), methomyl was in the liquid formulation as Lannate® LV (29% of active ingredient). Compound 1 was in a water dispersible granules (WDG) formulation with 35% active ingredient. The test compounds were dissolved in water. Enough water was added to make 100 ppm of active ingredient for each compound. Serial dilutions were made to obtain the appropriate concentrations. To obtain the desired mixture concentrations of each compound, twice the desired concentration of each of the two mixture partner compounds were mixed together in equal volumes.

The diluted solutions of the test compounds were sprayed to run-off on three-week-old tomato plants. The plants were placed on a rotating turntable sprayer (10 rpm). Test solutions were applied using a flat fan air-assisted nozzle (Spraying Systems 122440) at 10 psi (69 kPa). After each treated plant had dried, leaves were excised from the treated plant. The leaves were cut into pieces, which were placed singly into 5.5 cm-by-3.5 cm cells of a sixteen-cell plastic tray. Each cell contained a 2.5-cm square of moistened chromatography paper to prevent desiccation. One insect was placed in each cell. There two trays per treatment. Trays were held in the growth chamber at 25° C., 16-hour light:8-hour dark, 60% relative humidity for 4 days. The test was evaluated visually at 72 hours for % of mortality and % feeding; the results are listed in Table 10.

TABLE 10

Beet Armyworm

| Compound 1 (ppm) | Methomyl (ppm) | ratio | % mortality (observed) | % feeding |
|---|---|---|---|---|
| 0.60 | 0 | — | 75 | 1 |
| 0.30 | 0 | — | 59 | 1 |
| 0.209 | 0 | — | 47 | 2 |
| 0.163 | 0 | — | 35 | 2 |
| 0.076 | 0 | — | 25 | 7 |
| 0.041 | 0 | — | 44 | 6 |
| 0.022 | 0 | — | 13 | 9 |
| 0 | 100 | — | 84 | 0 |
| 0 | 37.8 | — | 44 | 3 |
| 0 | 20.6 | — | 16 | 10 |
| 0 | 16.3 | — | 44 | 9 |
| 0 | 10.9 | — | 10 | 29 |
| 0 | 5.22 | — | 6 | 17 |
| 0.209 | 5.22 | 1:25 | 13 | 4 |
| 0.163 | 16.3 | 1:100 | 41 | 3 |
| 0.076 | 37.8 | 1:500 | 59 | 1 |
| 0.041 | 20.6 | 1:500 | 22 | 5 |
| 0.022 | 10.9 | 1:500 | 16 | 8 |
| 0 | 0 | — | 0 | 14 |

Test J

For evaluating foliar control of cabbage looper (*Trichoplusia ni*), cabbage (var. Stonehead) plants were grown in Metromix potting soil in 10-cm pots in aluminum trays to test size (28 days, 3-4 full leaves). Test compounds were formulated and sprayed on test plants as described for Test I. After drying for 2 hours, the treated leaves were excised and infested with one cabbage looper per cell and covered. The test units were placed on trays and put in a growth chamber at 25° C. and 60% relative humidity for 4 days. Each test unit was then visually assessed for % mortality and % feeding; the results are listed in Table 11.

TABLE 11

Cabbage Looper

| Compound 1 (ppm) | Indoxacarb (ppm) | ratio | % mortality (observed) | % feeding |
|---|---|---|---|---|
| 0.057 | 0 | — | 22 | 24 |
| 0.032 | 0 | — | 9 | 82 |
| 0 | 0.27 | — | 56 | 38 |
| 0 | 0.146 | — | 31 | 68 |
| 0.057 | 0.27 | 1:4.7 | 63 | 9 |
| 0.032 | 0.146 | 1:4.7 | 38 | 13 |
| 0.017 | 0.082 | 1:4.7 | 6 | 86 |
| 0 | 0 | — | 3 | 97 |

Test K

For evaluating control of diamondback moth (*Plutella xylostella*), cabbage (var. Stonehead) plants were grown in Metromix potting soil in 10-cm pots in aluminum trays to test size (28 days, 3-4 full leaves) the plants were sprayed to the point of runoff using the turntable sprayer as described in Test I. Test compounds were formulated and sprayed on test plants as described for Test I. After drying for 2 hours, the treated leaves were excised and infested with one cabbage looper per cell and covered. The test units were placed on trays and put in a growth chamber at 25° C. and 60% relative humidity for 4 days. Each test unit was then visually assessed; Table 12A lists both the % mortality and % feeding results; and Tables 12B and 12C list only the % mortality results.

TABLE 12A

Diamondback Moth

| Compound 1 (ppm) | Indoxacarb (ppm) | ratio | % mortality (observed) | % feeding |
|---|---|---|---|---|
| 0.030 | 0 | — | 78 | 0 |
| 0.013 | 0 | — | 34 | 2.1 |
| 0.007 | 0 | — | 13 | 10.0 |
| 0 | 1 | — | 50 | 0.1 |
| 0 | 0.340 | — | 47 | 0.5 |
| 0 | 0.226 | — | 25 | 3.5 |
| 0 | 0.147 | — | 33 | 13.8 |
| 0.030 | 0.340 | 1:11 | 56 | 0.4 |
| 0.013 | 0.147 | 1:11 | 32 | 4.0 |
| 0.007 | 0.226 | 1:34 | 30 | 3.8 |
| 0 | 0 | — | 24 | 51.9 |

TABLE 12B

| Diamondback Moth | rate (ppm) | % mortality (obs) | rate (ppm) | % mortality (obs) | rate (ppm) | % mortality (obs) |
|---|---|---|---|---|---|---|
| Compound 1 | 0.01 | 87 | 0.02 | 77 | 0.04 | 93 |
| Methomyl | 30 | 80 | 40 | 90 | 50 | 80 |
| Cpd 1 + Methomyl | 0.01 + 30 | 90 | 0.02 + 30 | 60 | 0.04 + 30 | 70 |
| Cpd 1 + Methomyl | 0.01 + 40 | 90 | 0.02 + 40 | 70 | 0.04 + 40 | 90 |
| Cpd 1 + Methomyl | 0.01 + 50 | 70 | 0.02 + 50 | 70 | 0.04 + 50 | 80 |
| Amitraz | 10 | 70 | 100 | 20 | 1000 | 50 |
| Cpd 1 + Amitraz | 0.01 + 10 | 80 | 0.02 + 10 | 20 | 0.04 + 10 | 50 |
| Cpd 1 + Amitraz | 0.01 + 100 | 70 | 0.02 + 100 | 50 | 0.04 + 100 | 10 |
| Cpd 1 + Amitraz | 0.01 + 1000 | 80 | 0.02 + 1000 | 60 | 0.04 + 1000 | 60 |
| Thiamethoxam | 30 | 90 | 40 | 100 | 50 | 100 |
| Cpd 1 + Thiamethoxam | 0.01 + 30 | 80 | 0.02 + 30 | 60 | 0.04 + 30 | 90 |
| Cpd 1 + Thiamethoxam | 0.01 + 40 | 50 | 0.02 + 40 | 50 | 0.04 + 40 | 100 |
| Cpd 1 + Thiamethoxam | 0.01 + 50 | 80 | 0.02 + 50 | 80 | 0.04 + 50 | 100 |
| Pyridaben | 100 | 100 | 150 | 80 | 200 | 100 |
| Cpd 1 + Pyridaben | 0.01 + 100 | 80 | 0.02 + 100 | 60 | 0.04 + 100 | 90 |
| Cpd 1 + Pyridaben | 0.01 + 150 | 90 | 0.02 + 150 | 80 | 0.04 + 150 | 100 |
| Cpd 1 + Pyridaben | 0.01 + 200 | 90 | 0.02 + 200 | 90 | 0.04 + 200 | 90 |
| Flonicamid | 1 | 0 | 15 | 60 | 1000 | 30 |
| Cpd 1 + Flonicamid | 0.01 + 1 | 90 | 0.02 + 1 | 100* | 0.04 + 1 | 90 |
| Cpd 1 + Flonicamid | 0.01 + 15 | 100 | 0.02 + 15 | 90 | 0.04 + 15 | 100* |
| Cpd 1 + Flonicamid | 0.01 + 1000 | 100* | 0.02 + 1000 | 100* | 0.04 + 1000 | 90 |
| Dieldrin | 2 | 90 | 2.5 | 100 | 3 | 100 |
| Cpd 1 + Dieldrin | 0.01 + 2 | 80 | 0.02 + 2 | 90 | 0.04 + 2 | 100 |
| Cpd 1 + Dieldrin | 0.01 + 2.5 | 90 | 0.02 + 2.5 | 90 | 0.04 + 2.5 | 90 |
| Cpd 1 + Dieldrin | 0.01 + 3 | 80 | 0.02 + 3 | 90 | 0.04 + 3 | 100 |
| Spinosad | 10 | 100 | 100 | 90 | 1000 | 100 |
| Cpd 1 + Spinosad | 0.01 + 10 | 90 | 0.02 + 10 | 100 | 0.04 + 10 | 100 |
| Cpd 1 + Spinosad | 0.01 + 100 | 100 | 0.02 + 100 | 100 | 0.04 + 100 | 90 |
| Cpd 1 + Spinosad | 0.01 + 1000 | 100 | 0.02 + 1000 | 100 | 0.04 + 1000 | 100 |

*indicates the observed % mortality is higher than the calculated % mortality by Colby equation.

TABLE 12C

| Diamondback Moth | rate (ppm) | % mortality (obs) | rate (ppm) | % mortality (obs) | rate (ppm) | % mortality (obs) |
|---|---|---|---|---|---|---|
| Compound 1 | 0.0025 | 79 | 0.02 | 77 | 0.04 | 75 |
| Fipronil | 10 | 100 | 100 | 100 | 1000 | 100 |
| Cpd 1 + Fipronil | 0.0025 + 10 | 100 | 0.02 + 10 | 100 | 0.04 + 10 | 100 |
| Cpd 1 + Fipronil | 0.0025 + 100 | 100 | 0.02 + 100 | 100 | 0.04 + 100 | 100 |
| Cpd 1 + Fipronil | 0.0025 + 1000 | 100 | 0.02 + 1000 | 100 | 0.04 + 1000 | 100 |
| Pyriproxyfen | 40 | 100 | 20 | 100 | 200 | 100 |
| Cpd 1 + Pyriproxyfen | 0.0025 + 2 | 100 | 0.02 + 2 | 100 | 0.04 + 2 | 100 |
| Cpd 1 + Pyriproxyfen | 0.0025 + 20 | 100 | 0.02 + 20 | 100 | 0.04 + 20 | 100 |
| Cpd 1 + Pyriproxyfen | 0.0025 + 200 | 100 | 0.02 + 200 | 100 | 0.04 + 200 | 100 |
| Pymetrozine | 250 | 100 | 1000 | 100 | 2000 | 100 |
| Cpd 1 + Pymetrozine | 0.0025 + 250 | 100 | 0.02 + 250 | 100 | 0.04 + 250 | 100 |
| Cpd 1 + Pymetrozine | 0.0025 + 1000 | 100 | 0.02 + 1000 | 100 | 0.04 + 1000 | 100 |
| Cpd 1 + Pymetrozine | 0.0025 + 2000 | 100 | 0.02 + 2000 | 100 | 0.04 + 2000 | 100 |

TABLE 12C-continued

| Diamondback Moth | rate (ppm) | % mortality (obs) | rate (ppm) | % mortality (obs) | rate (ppm) | % mortality (obs) |
|---|---|---|---|---|---|---|
| Buprofezin | 10 | 30 | 100 | 20 | 1000 | 60 |
| Cpd 1 + Buprofezin | 0.0025 + 10 | 60 | 0.02 + 10 | 40 | 0.04 + 10 | 60 |
| Cpd 1 + Buprofezin | 0.0025 + 100 | 20 | 0.02 + 100 | 10 | 0.04 + 100 | 60 |
| Cpd 1 + Buprofezin | 0.0025 + 1000 | 0 | 0.02 + 1000 | 20 | 0.04 + 1000 | 40 |
| Chlorfenapyr | 1.5 | 90 | 2.5 | 100 | 7 | 70 |
| Cpd 1 + Chlorfenapyr | 0.0025 + 1.5 | 100 | 0.02 + 1.5 | 70 | 0.04 + 1.5 | 90 |
| Cpd 1 + Chlorfenapyr | 0.0025 + 3.5 | 90 | 0.02 + 3.5 | 70 | 0.04 + 3.5 | 90 |
| Cpd 1 + Chlorfenapyr | 0.0025 + 7 | 90 | 0.02 + 7 | 90 | 0.04 + 7 | 90 |
| Chlorpyrifos | 10 | 80 | 100 | 40 | 1000 | 50 |
| Cpd 1 + Chlorpyrifos | 0.0025 + 10 | 20 | 0.02 + 10 | 20 | 0.04 + 10 | 30 |
| Cpd 1 + Chlorpyrifos | 0.0025 + 100 | 0 | 0.02 + 100 | 10 | 0.04 + 100 | 50 |
| Cpd 1 + Chlorpyrifos | 0.0025 + 1000 | 30 | 0.02 + 1000 | 20 | 0.04 + 1000 | 90 |
| Cyromazine | 20 | 60 | 40 | 90 | 60 | 80 |
| Cpd 1 + Cyromazine | 0.0025 + 20 | 20 | 0.02 + 20 | 30 | 0.04 + 20 | 90 |
| Cpd 1 + Cyromazine | 0.0025 + 40 | 80 | 0.02 + 40 | 80 | 0.04 + 40 | 90 |
| Cpd 1 + Cyromazine | 0.0025 + 60 | 90 | 0.02 + 60 | 90 | 0.04 + 60 | 80 |
| Fenoxycarb | 10 | 90 | 100 | 90 | 1000 | 90 |
| Cpd 1 + Fenoxycarb | 0.0025 + 10 | 80 | 0.02 + 10 | 70 | 0.04 + 10 | 90 |
| Cpd 1 + Fenoxycarb | 0.0025 + 100 | 60 | 0.02 + 100 | 80 | 0.04 + 100 | 90 |
| Cpd 1 + Fenoxycarb | 0.0025 + 1000 | 90 | 0.02 + 1000 | 60 | 0.04 + 1000 | 80 |
| Methoprene | 10 | 90 | 100 | 100 | 1000 | 90 |
| Cpd 1 + Methoprene | 0.0025 + 10 | 90 | 0.02 + 10 | 90 | 0.04 + 10 | 90 |
| Cpd 1 + Methoprene | 0.0025 + 100 | 90 | 0.02 + 100 | 90 | 0.04 + 100 | 90 |
| Cpd 1 + Methoprene | 0.0025 + 1000 | 90 | 0.02 + 1000 | 90 | 0.04 + 1000 | 90 |
| Indoxacarb | 0.02 | 80 | 0.05 | 40 | 0.4 | 0 |
| Cpd 1 + Indoxacarb | 0.0025 + 0.02 | 70 | 0.02 + 0.02 | 80 | 0.04 + 0.02 | 90 |
| Cpd 1 + Indoxacarb | 0.0025 + 0.05 | 60 | 0.02 + 0.05 | 90 | 0.04 + 0.05 | 90 |
| Cpd 1 + Indoxacarb | 0.0025 + 0.4 | 10 | 0.02 + 0.4 | 60 | 0.04 + 0.4 | 90* |
| Triazamate | 250 | 90 | 350 | 60 | 500 | 50 |
| Cpd 1 + Triazamate | 0.0025 + 250 | 60 | 0.02 + 250 | 50 | 0.04 + 250 | 50 |
| Cpd 1 + Triazamate | 0.0025 + 350 | 30 | 0.02 + 350 | 60 | 0.04 + 350 | 80 |
| Cpd 1 + Triazamate | 0.0025 + 500 | 30 | 0.02 + 500 | 40 | 0.04 + 500 | 80 |
| Thiodicarb | 100 | 90 | 1000 | 90 | 3000 | 90 |
| Cpd 1 + Thiodicarb | 0.0025 + 100 | 90 | 0.02 + 100 | 90 | 0.04 + 100 | 90 |
| Cpd 1 + Thiodicarb | 0.0025 + 1000 | 90 | 0.02 + 1000 | 90 | 0.04 + 1000 | 90 |
| Cpd 1 + Thiodicarb | 0.0025 + 3000 | 90 | 0.02 + 3000 | 90 | 0.04 + 3000 | 90 |
| Tebufenozide | 150 | 90 | 200 | 90 | 300 | 90 |
| Cpd 1 + Tebufenozide | 0.0025 + 150 | 70 | 0.02 + 150 | 90 | 0.04 + 150 | 90 |
| Cpd 1 + Tebufenozide | 0.0025 + 200 | 40 | 0.02 + 200 | 90 | 0.04 + 200 | 90 |
| Cpd 1 + Tebufenozide | 0.0025 + 300 | 80 | 0.02 + 300 | 80 | 0.04 + 300 | 90 |
| Deltamethrin | 0.1 | 90 | 0.3 | 90 | 1 | 90 |
| Cpd 1 + Deltamethrin | 0.0025 + 0.1 | 80 | 0.02 + 0.1 | 90 | 0.04 + 0.1 | 90 |
| Cpd 1 + Deltamethrin | 0.0025 + 0.3 | 60 | 0.02 + 0.3 | 70 | 0.04 + 0.3 | 90 |
| Cpd 1 + Deltamethrin | 0.0025 + 1 | 90 | 0.02 + 1 | 90 | 0.04 + 1 | 80 |
| Oxamyl | 1 | 60 | 10 | 20 | 100 | 30 |
| Cpd 1 + Oxamyl | 0.0025 + 1 | 30 | 0.02 + 1 | 30 | 0.04 + 1 | 70 |
| Cpd 1 + Oxamyl | 0.0025 + 10 | 10 | 0.02 + 10 | 20 | 0.04 + 10 | 70 |
| Cpd 1 + Oxamyl | 0.0025 + 100 | 20 | 0.02 + 100 | 20 | 0.04 + 100 | 80 |
| Hexaflumuron | 0.5 | 70 | 1 | 30 | 2 | 70 |
| Cpd 1 + Hexaflumuron | 0.0025 + 0.5 | 20 | 0.02 + 0.5 | 70 | 0.04 + 0.5 | 90 |
| Cpd 1 + Hexaflumuron | 0.0025 + 1 | 80 | 0.02 + 1 | 90* | 0.04 + 1 | 90* |
| Cpd 1 + Hexaflumuron | 0.0025 + 2 | 70 | 0.02 + 2 | 80 | 0.04 + 2 | 90 |
| Acetamiprid | 0.3 | 90 | 1 | 80 | 3 | 70 |
| Cpd 1 + Acetamiprid | 0.0025 + 0.3 | 0 | 0.02 + 0.3 | 10 | 0.04 + 0.3 | 30 |
| Cpd 1 + Acetamiprid | 0.0025 + 1 | 20 | 0.02 + 1 | 20 | 0.04 + 1 | 70 |
| Cpd 1 + Acetamiprid | 0.0025 + 3 | 20 | 0.02 + 3 | 40 | 0.04 + 3 | 70 |
| Cartap | 100 | 60 | 1000 | 90 | 3000 | 90 |
| Cpd 1 + Cartap | 0.0025 + 100 | 90 | 0.02 + 100 | 90 | 0.04 + 100 | 90 |
| Cpd 1 + Cartap | 0.0025 + 1000 | 90* | 0.02 + 1000 | 100* | 0.04 + 1000 | 90 |
| Cpd 1 + Cartap | 0.0025 + 3000 | 100 | 0.02 + 3000 | 100* | 0.04 + 3000 | 100* |
| Esfenvalerate | 0.01 | 90 | 0.05 | 80 | 0.2 | 80 |
| Cpd 1 + Esfenvalerate | 0.0025 + 0.01 | 60 | 0.02 + 0.01 | 70 | 0.04 + 0.01 | 90 |
| Cpd 1 + Esfenvalerate | 0.0025 + 0.05 | 70 | 0.02 + 0.05 | 60 | 0.04 + 0.05 | 90 |
| Cpd 1 + Esfenvalerate | 0.0025 + 0.2 | 50 | 0.02 + 0.2 | 80 | 0.04 + 0.2 | 80 |
| Thiacloprid | 0.1 | 80 | 0.3 | 40 | 15 | 90 |
| Cpd 1 + Thiacloprid | 0.0025 + 0.1 | 30 | 0.02 + 0.1 | 20 | 0.04 + 0.1 | 80 |
| Cpd 1 + Thiacloprid | 0.0025 + 0.3 | 10 | 0.02 + 0.3 | 30 | 0.04 + 0.3 | 70 |
| Cpd 1 + Thiacloprid | 0.0025 + 15 | 90 | 0.02 + 15 | 90 | 0.04 + 15 | 90 |
| Lambda-cyhalothrin | 0.016 | 90 | 0.08 | 70 | 0.4 | 90 |
| Cpd 1 + Lambda-cyhalothrin | 0.0025 + 0.016 | 50 | 0.02 + 0.016 | 90 | 0.04 + 0.016 | 90 |
| Cpd 1 + Lambda-cyhalothrin | 0.0025 + 0.08 | 80 | 0.02 + 0.08 | 60 | 0.04 + 0.08 | 90 |
| Cpd 1 + Lambda-cyhalothrin | 0.0025 + 0.4 | 90 | 0.02 + 0.4 | 90 | 0.04 + 0.4 | 100* |
| Hydramethylnon | 0.01 | 70 | 0.05 | 50 | 0.2 | 60 |
| Cpd 1 + Hydramethylnon | 0.0025 + 0.01 | 50 | 0.02 + 0.01 | 60 | 0.04 + 0.01 | 70 |
| Cpd 1 + Hydramethylnon | 0.0025 + 0.05 | 0 | 0.02 + 0.05 | 60 | 0.04 + 0.05 | 70 |
| Cpd 1 + Hydramethylnon | 0.0025 + 0.2 | 20 | 0.02 + 0.2 | 10 | 0.04 + 0.2 | 80 |
| Clothianidin | 0.016 | 40 | 0.08 | 10 | 0.4 | 20 |

TABLE 12C-continued

| Diamondback Moth | rate (ppm) | % mortality (obs) | rate (ppm) | % mortality (obs) | rate (ppm) | % mortality (obs) |
|---|---|---|---|---|---|---|
| Cpd 1 + Clothianidin | 0.0025 + 0.016 | 70 | 0.02 + 0.016 | 40 | 0.04 + 0.016 | 70 |
| Cpd 1 + Clothianidin | 0.0025 + 0.08 | 30 | 0.02 + 0.08 | 50 | 0.04 + 0.08 | 90* |
| Cpd 1 + Clothianidin | 0.0025 + 0.4 | 20 | 0.02 + 0.4 | 50 | 0.04 + 0.4 | 100* |
| Lufenuron | 0.08 | 80 | 0.4 | 80 | 2 | 90 |
| Cpd 1 + Lufenuron | 0.0025 + 0.08 | 50 | 0.02 + 0.08 | 30 | 0.04 + 0.08 | 80 |
| Cpd 1 + Lufenuron | 0.0025 + 0.4 | 60 | 0.02 + 0.4 | 60 | 0.04 + 0.4 | 100 |
| Cpd 1 + Lufenuron | 0.0025 + 2 | 70 | 0.02 + 2 | 70 | 0.04 + 2 | 100 |
| Abamectin | 0.02 | 90 | 0.08 | 90 | 0.4 | 100 |
| Cpd 1 + Abamectin | 0.0025 + 0.02 | 90 | 0.02 + 0.02 | 90 | 0.04 + 0.02 | 100* |
| Cpd 1 + Abamectin | 0.0025 + 0.08 | 100* | 0.02 + 0.08 | 100* | 0.04 + 0.08 | 90 |
| Cpd 1 + Abamectin | 0.0025 + 0.4 | 90 | 0.02 + 0.4 | 100 | 0.04 + 0.4 | 100* |
| Methoxyfenozide | 0.08 | 90 | 0.4 | 90 | 2 | 90 |
| Cpd 1 + Methoxyfenozide | 0.0025 + 0.08 | 80 | 0.02 + 0.08 | 100* | 0.04 + 0.08 | 100* |
| Cpd 1 + Methoxyfenozide | 0.0025 + 0.4 | 90 | 0.02 + 0.4 | 80 | 0.04 + 0.4 | 100* |
| Cpd 1 + Methoxyfenozide | 0.0025 + 2 | 100* | 0.02 + 2 | 90 | 0.04 + 2 | 90 |
| Nitenpyram | 30 | 90 | 75 | 80 | 150 | 90 |
| Cpd 1 + Nitenpyram | 0.0025 + 30 | 90 | 0.02 + 30 | 100* | 0.04 + 30 | 90 |
| Cpd 1 + Nitenpyram | 0.0025 + 75 | 100* | 0.02 + 75 | 90 | 0.04 + 75 | 100* |
| Cpd 1 + Nitenpyram | 0.0025 + 150 | 100* | 0.02 + 150 | 100* | 0.04 + 150 | 100* |
| Pyridalyl | 0.5 | 90 | 0.6 | 100 | 0.7 | 100 |
| Cpd 1 + Pyridalyl | 0.0025 + 0.5 | 90 | 0.02 + 0.5 | 90 | 0.04 + 0.5 | 90 |
| Cpd 1 + Pyridalyl | 0.0025 + 0.6 | 80 | 0.02 + 0.6 | 100 | 0.04 + 0.6 | 90 |
| Cpd 1 + Pyridalyl | 0.0025 + 0.7 | 90 | 0.02 + 0.7 | 90 | 0.04 + 0.7 | 90 |
| Dinotefuran | 1 | 80 | 2.5 | 60 | 7.5 | 70 |
| Cpd 1 + Dinotefuran | 0.0025 + 1 | 100* | 0.02 + 1 | 90 | 0.04 + 1 | 90 |
| Cpd 1 + Dinotefuran | 0.0025 + 2.5 | 90 | 0.02 + 2.5 | 90 | 0.04 + 2.5 | 100* |
| Cpd 1 + Dinotefuran | 0.0025 + 7.5 | 100* | 0.02 + 7.5 | 90 | 0.04 + 7.5 | 100* |

Tables 2 to 12 show mixtures and compositions of the present invention demonstrating control on a wide range of invertebrate pests, some with notable synergistic effect. As the % of mortality cannot exceed 100%, the unexpected increase in insecticidal activity can be greatest only when the separate active ingredient components alone are at application rates providing considerably less than 100% control. Synergy may not be evident at low application rates where the individual active ingredient components alone have little activity. However, in some instances high activity was observed for combinations wherein individual active ingredient alone at the same application rate had essentially no activity. The synergism is indeed highly remarkable. Noteworthy are mixtures of the compound of Formula 1 and wherein the pest control agent of component (b1) is imidacloprid. Especially noteworthy are weight ratios of component (b) to the compound of Formula 1 in the mixtures and compositions of the present invention which are typically from 200:1 to 1:150, with one embodiment being from 150:1 to 1:50, another embodiment being from 50:1 to 1:10 and another embodiment being from 5:1 to 1:5.

Accordingly, this invention provides not only improved compositions but also methods of their use for control of invertebrate pests such as arthropods in both agronomic and non-agronomic environments. The compositions of this invention demonstrate high controlling effect of invertebrate pests; consequently, their use as arthropodicides can reduce crop production cost and environmental load.

What is claimed is:

1. A method for controlling silverleaf whitefly (*Bemisia argentifolii*) comprising contacting silverleaf whitefly or its environment with a synergistically effective amount of a mixture comprising:

(a) a compound of Formula 1, 3-bromo-N-[4-chloro-2-methyl-6-[(methylamino)carbonyl]phenyl]-1-(3-chloro-2-pyridinyl)-1H-pyrazole-5-carboxamide, an N-oxide, or a salt thereof,

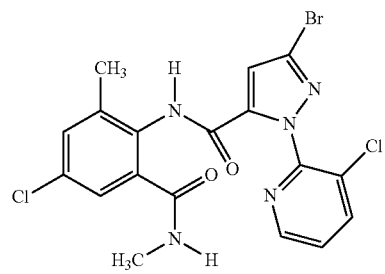

and
a component (b) wherein the component (b) is imidacloprid and the weight ratio of the component (b) to the compound of Formula 1, an N-oxide, or salt thereof, is from 8:1 to 1:1.

2. The method of claim 1 wherein the environment is soil and a liquid composition comprising the mixture is applied to the soil as a soil drench.

3. The method of claim 1 wherein the weight ratio of imidacloprid to the compound of Formula 1 is 1:1.

4. The method of claim 1 wherein the mixture further comprises at least one additional component selected from the group consisting of a surfactant, a solid diluent and a liquid diluent.

5. The method of claim 1 wherein the mixture further comprises an effective amount of at least one additional biologically active compound or agent.

* * * * *